(12) United States Patent
Chaikof et al.

(10) Patent No.: US 6,936,298 B2
(45) Date of Patent: Aug. 30, 2005

(54) ANTITHROMBOGENIC MEMBRANE MIMETIC COMPOSITIONS AND METHODS

(75) Inventors: Elliot L. Chaikof, Atlanta, GA (US); June Feng, Duluth, GA (US); Janine M. Orban, Warsaw, IN (US); Hongbo Liu, Willimantic, CT (US); Xue-Long Sun, Atlanta, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 10/257,805

(22) PCT Filed: Apr. 13, 2001

(86) PCT No.: PCT/US01/12094

§ 371 (c)(1),
(2), (4) Date: Apr. 15, 2003

(87) PCT Pub. No.: WO01/78800

PCT Pub. Date: Oct. 25, 2001

(65) Prior Publication Data

US 2004/0073295 A1 Apr. 15, 2004

Related U.S. Application Data

(60) Provisional application No. 60/197,072, filed on Apr. 13, 2000, and provisional application No. 60/221,618, filed on Jul. 28, 2000.

(51) Int. Cl.$^7$ ............................................. A61L 27/00
(52) U.S. Cl. ...................... 427/2.24; 427/2.25; 427/2.3; 623/1.49; 623/2.42; 623/11.11
(58) Field of Search .............................. 427/2.24, 2.25, 427/2.28, 2.3, 2.31; 623/1.1–3.3, 11.11, 23.64–23.76

(56) References Cited

U.S. PATENT DOCUMENTS

| | | | |
|---|---|---|---|
| 4,485,045 A | 11/1984 | Regen | 260/403 |
| 4,522,803 A | 6/1985 | Lenk et al. | 424/1.1 |
| 4,560,599 A | 12/1985 | Regen | 428/36 |
| 4,880,883 A | 11/1989 | Grasel et al. | 535/454 |
| 4,906,465 A | 3/1990 | Chaikof et al. | 424/78 |
| 5,071,532 A | 12/1991 | Taillet et al. | 204/228 |
| 5,288,517 A | 2/1994 | Kanno et al. | 427/244 |
| 5,399,331 A | 3/1995 | Loughrey et al. | 424/450 |
| 5,417,969 A | 5/1995 | Hsu et al. | 424/78 |
| 5,429,618 A | 7/1995 | Keogh | 604/266 |
| 5,741,325 A | 4/1998 | Chaikof et al. | 623/1 |
| 5,755,788 A | 5/1998 | Strauss | 623/11 |
| 5,911,942 A | 6/1999 | Fofonoff et al. | 264/444 |
| 6,071,532 A | 6/2000 | Chaikof et al. | 424/450 |
| 6,171,614 B1 | 1/2001 | Chaikof et al. | 424/450 |
| 6,583,251 B1 * | 6/2003 | Chaikof et al. | 526/277 |
| 2004/0063200 A1 * | 4/2004 | Chaikof et al. | 435/317.1 |

FOREIGN PATENT DOCUMENTS

| | | | | |
|---|---|---|---|---|
| WO | WO 96/21469 | 7/1996 | ........... | A61K/47/48 |
| WO | WO 98/16198 | 4/1998 | ........... | A61K/9/127 |
| WO | WO 00/00239 | 1/2000 | ........... | A61L/33/00 |
| WO | WO 01/78800 | 4/2001 | ........... | A61L/33/00 |
| WO | WO 01/80921 | 4/2001 | ........... | A61L/31/00 |
| WO | WO 02/09647 | 7/2001 | | |
| WO | WO 02/055021 | 1/2002 | | |

OTHER PUBLICATIONS

US 5,556,632, 9/1996, Kohler et al. (withdrawn)

Akagawa, M. and Suyama, K., "Mechanism of formation of elastin crosslinks," (2000) *Connect. Tissue Res.* 41(2):131–141.

Akita, K. et al., Effect of FK506 and anti–CD4 therapy on fetal pig pancreas xenografts and host lymphoid cells in NOD/Lt, CBA, and BALB/c mice, (1994) *Cell Transplantation* 3(1):61–73.

Anderson et al., "Bioactive silk–like protein polymer films on silicon devices," Alper, M., Bayby, H., Kaplan, D. and Navia, M., ed.; *Materials Research Society Symp Proc.:* Pittsburgh, PA; 1994, 330:171–177.

Andree, H.A.M. et al., "Transport rate limited catalysis on macroscopic surfaces: the activation of factor X in a continuous flow enzyme reactor," (1994) *Biochemistry* 33(14):4368–4374.

Aoi, K. et al., "Glycopeptide synthesis by an α–amino acid N–carboxyanhydride (NCA) method: ring–opening polymerization of a sugar–substituted NCA," (1994) *Macromolecules* 27:875–877.

Aoi, K. et al., "Architectural control of sugar–containing polymers by living polymerization: ring–opening polymerization of 2–oxazolines initiated with carbohydrate derivatives," (1992) *Macromolecules* 25:7073–7075.

Arnander, C. and Olsson, P., "Influence of blood flow and the effect of protamine on the thromboresistant properties of a covalently bonded heparin surface," (1988) *J. Biomed. Mater. Res.* 22(10):859–868.

Balachander, N. and Sukenik, C.N., "Monolayer transformation by nucleophilic substitution: applications to the creation of new monolayer assemblies," (1990) *Langmuir* 6(11):1621–1627.

Basmadjian, D, et al., "Coagulation on biomaterials in flowing blood: some theoretical considerations," (1997) *Biomaterials* 17(23):1511–1522.

(Continued)

*Primary Examiner*—Shrive P. Beck
*Assistant Examiner*—William Phillip Fletcher, III
(74) *Attorney, Agent, or Firm*—Donna M. Ferber; Steven J. Penner; Greenlee, Winner and Sullivan, P.C.

(57) ABSTRACT

The present Specification describes materials and methods which provide for improved performance of medical prostheses, including vascular graft material, artificial heart valves, and other implanted materials. The materials comprising bound thrombomodulin or a functionally equivalent derivative protein, provide for fewer undesirable side effects including inflammation, thromboses and neointimal hyperplasia.

21 Claims, 5 Drawing Sheets

OTHER PUBLICATIONS

Basmadjian, D. and Sefton, M.V., "Relationship between release rate and surface concentration for heparinized materials," (1983) *Journal of Biomedical Materials Research* 17(3):509–518.

Beyer, D. et al., "Covalently attached polymer mono– and multilayers on silanized glass substrates," (1996) *Thin Solid Films* 285:825–828.

Bierbaum, K. et al., "A near edge X–ray absorption fine structure spectroscopy and X–ray photoelectron spectroscopy study of the film properties of self–assembled monolayers of organosilanes on oxidized Si(100)," (1995) *Langmuir* 11:512–518.

Biessen, E.A.L. et al., "Synthesis of cluster galactosides with high affinity for the hepatic asialoglycoprotein receptor" (1995) *J. Med. Chem.* 38:1538–1546.

Billy, D. et Al., "Prothrombin activation by prothrombinase in a tubular flow reactor," (1995) *J. Biol. Chem.* 270(3):1029–1034.

Biro, S. et al., "Expression and subcellular distribution of basic fibroblast growth factor are regulated during migration of endothelial cells," (1994) *Circ. Res.* 74:485–494.

Bitomsky, W. and Wade, R.C., "Docking of glycosaminoglycans to heparin–binding proteins: validation for aFGF, bFGF, and antithrombin and application to IL–8," (1999) *J. Am. Chem. Soc.* 121:3004–3103.

Björquist, P. et al., "Determination of the inetic constants of tissue factor/factor VII/factor VIIA and antithrombin/heparin using surface plasmon resonance," (1997) *Thromb. Res.* 85(3):225–236.

Blezer, R. et al., "Initiation and propagation of blood coagulation at artificial surfaces studied in a capillary flow reactor," (1998) *Thromb. Haemostasis* 79(2):296–301.

Blezer, R. et al., "Activation of blood coagulation at heparin–coated surfaces," (1997) *J. Biomedical Materials Research* 37(1):108–113.

Bon, S.A.F. and Haddleton, D.M., "Amphiphilic copolymers by atom transfer polymerization with carbohydrate–based initiators and monomers," (1999) *Polym. Prepr.* (Am. Chem. Soc., Div. Polym. Chem.) 40(2):248–249.

Bourin, M.C. and Lindahl, U., "Glycosaminoglycans and the regulation of blood coagulation," (1993) *Biochemical J.* 289(Pt2):313–330.

Brittain, H.A. et al., "Sickle erythrocyte adherence to large vessel and microvascular endothelium under physiologic flow is qualitatively different," (1992) *J. Lab. Clin. Med.* 112:538–545.

Broch, H. et al., "Quantum molecular modeling of the elastinic tetrapeptide Val–Pro–Gly–Gly," (1998) *J. Biomol. Struct. & Dyn.* 15: 1073–1091.

Brown, D.F.M., "Treatment options for deep venous thrombosis," (Nov. 2001) *Emergency Medicine Clinics of North America* 19(4):913–923.

Brummel, .E. et al., "An integrated study of fibrinogen during blood coagulation," (1999) *J. Biol. Chem.* 274(32):22862–22870.

Buller, C.E. et al., "Primary stenting versus balloon angioplasty in occluded coronary arteries," (1999) *Circulation* 100(3):236–242.

Byun, Y. et al., "Binding of antithrombin III and thrombin to immobilized heparin under flow conditions," (1996) *Biotechnology Progress* 12(2):217–225.

Byun, Y. et al., "Mechanism of thrombin inactivation by immobilized heparin," (1996) *J. Biomed. Mater. Res.* 30:423–427.

Cai, W.Z. et al., "A solid–state n.m.r. study of microphase structure and segmental dynamics of poly(styrene–b–methylphenysiloxane) diblock copolymers," (1993) *Polymer* 34:267–276.

Campbell, E.J. et al., "Biocompatible surfaces using methacryloylphosphorylcholine laurylmethacrylate copolymer," (1994) *ASAIO J.* 40(3):M853–M857.

Callstri–Yeh, M. et al., "Thermal stability of self–assembled monolayers from alkytchlorosilanes," (1996) *Langmuir* 12:2747.

Cao, Q. et al., "Sequence of abductin, the molluscan 'rubber' protein," (1997) *Curr. Biol.* 7:R677–678.

Chaikof, E.L., "Biomaterials that imitate cell microenvironments," (1996) *Chemtech.* 26:17–24.

Chaikof, E.L. et al., "PEO enhancement of platelet deposition, fibrinogen deposition, and complement C3 activation," (1992) *J. Biomed. Mater. Res.* 26:1163–1168.

Chang, D.K. et al., "Nuclear overhauser effect and computational characterization of the β–spiral of the polypentapeptide of elastin," (1989) *J. Biomol. Struct. Dyn.* 6(5):851–858.

Chang, D.K. and Urry, D.W., "Molecular dynamics calculations on relaxed and extended states of the polypentapeptide of elastin," (1988) *Chem. Phys. Lett.* 147:395–400.

Chapman, D., "Biomembranes and new hemocompatible materials," (1993) *Langmuir* 9:39–45.

Chen, C. et al., "Phosphorylcholine coating of ePTFE grafts reduces neointimal hyperplasia in canine model," (1997) *Ann. Vasc. Surg.* 11(1):74–79.

Chen, T–M et al., "Studies on the synthesis and properties of novel phospholipid analogous polymers," (1996) *J. Appl. Polym. Sci.* 60:455–464.

Cheung, J. H. et al., "Molecular self–assembly of conducting polymers," (1994) *Thin Solid Films* 244:985–989.

Chon, J.H. et al., "Cytomimetic biomaterials. 3. Preparation and transport studies of an alginate/amphiphilic copolymer/polymerized phospholipid film," (1999) *J. Biomater. Sci. Polymer. Ed.* 10:95–107.

Chon, J.H. et al., "α4β1 and α5β1 control cell migration on fibronectin by differentially regulating cell speed and motile cell phenotype," (1998) *Ann. Biomed. Eng.* 26:1091–1101.

Chon, J.H. et al., "Role of fibronectin and sulfated proteoglycans in endothelial cell migration on a cultured smooth muscle layer," (1997) *J. Surg. Res.* 72:53–59.

Christianson, S. et al., "Adoptive transfer of diabetes into immunodeficient NOD–scid/scid mice: relative contributions of CD4$^+$ and CD8$^+$ T–cells from diabetic versus prediabetic NOD.NON–Thy–1$^a$ donors," (1993) *Diabetes* 42:44–55.

Cima, L.G. and Lopina, S.T., "Network structures of radiation–cross–linked star polymer gels," (1995) *Macromolecules* 28:6787–6794.

Clowes, AW et al., "Mechanisms of arterial graft failure. II. Chronic endothelial and smooth muscle cell proliferation in healing polytetrafluoroethylene prostheses," (1986) *J. Vasc. Surg.* 3:877–884.

Clowes, A.W. et al., "Mechanisms of arterial graft failure. 1. Role of cellular proliferation in early healing of PTFE prostheses," (1985)*Am. J. Pathol.* 118(1]:43–54.

Clowes, A.W. and Karnovsky, M.J., "Suppression by heparin of smooth muscle cell proliferation in injured arteries," (1977) *Nature* 625–626.

Colton, C.K., "The engineering of xenogeneic islet transplantation by immunoisolation," (1992) *Diab. Nutr. Metabol.* 5:145–149.

Colton, C. and Avgoustiniatos, E. "Bioengineering in the development of the hybrid artificial pancreas I" (1991) *Biochem. Eng.* 113:152–70.

Contino, P.B. et al., "Use of an oriented transmembrane protein to probe the assembly of a supported phospholipid bilayer," (1994) *Biophys. J.* 67:1113–1116.

Crooks, C.A., et al., "Microencapsulation of mammalian cells in a HEMA–MMA copolymer: effects on capsule morphology and permeability," (1990) *J. Biomed. Mater. Res.* 24: 1241–1262.

Cruise, G.M. et al., "A sensitivity study of the key parameters in the interfacial photopolymerization of poly(ethylene glycol) diacrylate upon porcine islets," (1998) *Biotechnol. Bioeng.* 57: 655–65.

Daugherty, D. L. and Gellman, S. H., "A fluorescence assay for leucine zipper dimerization: avoiding unintended consequences of fluorophore attachment," (1999) *J. Am. Chem. Soc.* 121:4325–4333.

Dautzenberg, H. et al., "Polyelectrolyte complex formation at the interface of solutions," (1996), *Polym. Sci.* 101:149–156.

Debelle, L. and Tamburro, A.M., "Elastin: molecular description and function," (1999) *Internat. J. Biochem. & Cell Biol.* 31:261–272.

Decher, G., "Fuzzy nanoassemblies: toward layered polymeric multicomposites," (1997) *Science* 277:1232–1237.

Defrees, S.A. et al., "Sialyl lewis x liposomes as a multivalent ligand and inhibitor of E-selectin mediated cellular adhesion," (1996) *J. Am. Chem. Soc.* 118:6101–6104.

Deming, T. J., "*Mussel byssus* and biomolecular materials," (1999) *Curr. Opin. Chem. Biol.* 3: 100–5.

Dixon, W. T., "Spinning–sideband–free and spinning–sideband–only NMR spectra in spinning samples," (1982) *J. Chem. Phys.* 77:1800–1809.

Dixon, W.T., "Total suppression of sidebands in CPMAS C–13 NMR," (1982) *J. Magn. Reson.* 49:341–345.

Dluhy, R.A., "Quantitative external reflection infrared spectroscopic analysis of insoluble monolayers spread at the air–water interface," (1986) *J. Phys. Chem.* 90:1373–1379.

Dodson, G.G. et al., "molecular recognition in insulin assembly," (1993) *Biochem. Soc. Trans.* 21:609–614.

Doshi, J. and Reneker, D.H., "Electrospinning process and applications of electrospun fibers," (1995) *J. Electrostatics* 35: 151–160.

Eaton, D. F., "Dye sensitized photo polymerization," (1986) *Advances in Photochemistry* 13:427–487.

Egger, N. et al., "Solid state NM investigation of cationic polymerized epoxy resins," (1992) *J. Appl. Poly. Sci.* 44:289–295.

Einaga, Y. et al., "Photofunctional vesicles containing Prussian blue and azobenzene" (1999) *J. Am. Chem. Soc.* 121:3745–3750.

Eitzman, D.T. et al., "Heparin neutralization by platelet–rich thrombi," (1994) *Circulation* 89(4):1523–1529.

Ejaz, M. et al., (2000) *Macromolecules* 33:2870.

Elbert, D. L. et al., "Thin polymer layers formed by polyelectrolyte multilayer techniques on biological surfaces," (1999) *Langmuir* 15:5355–5362.

Elender, G. et al., "Functionalisation of Si/SiO$_2$ and glass surfaces with ultrathin dextran films and deposition of lipid bilayers," (1996) *E. Biosensors Bioelectronics* 11:565–577.

Elliott, J. T. and Prestwich, G. D., "Maleimide–functionalized lipids that anchor polypeptides to lipid bilayers and membranes," (2000) *Bioconjugate Chem.* 11:832–841.

Esmon, C.T. et al., "Regulation and functions of the protein C anticoagulant pathway," (1999) *Haematologica* 84(4):363–368.

Esmon, C.T. et al., "The protein C pathway: new insights," (1997) *Thromb. Haemostasis* 78(1):70–74.

Esmon, C.T., "Thrombomodulin as a model of molecular mechanisms that modulate protease specificity and function at the vessel surface," (1995) *FASEB Journal* 9(10):946–955.

Esmon, C.T. and Owen, W.G., "Identification of an endothelial cell cofactor for thrombin–catalyzed activation of protein C," (1981) *Proc. Natl. Acad. Sci. USA* 78(4):2249–2252.

Esmon, N.L. et al., "Proteolytic formation and properties of y–carboxyglutamic acid–domainless protein C," (1983) *J. Biol. Chem.* 258:(9):5548–5553.

Esmon, N.L. et al., "Thrombomodutin blocks the ability of thrombin to activate platelets," (1983) *J. Biol. Chem.* 258(20):12238–12242.

Esmon, N.L. et al., "Isolation of a membrane–bound cofactor for thrombin–catalyzed activation of protein C," (1982) *J. Biol. Chem.* 257(2):859–864.

España, F. et al., "In vivo and in vitro complexes of activated protein C with two inhibitors in baboons," (1991) *Blood* 77(8):1754–1760.

Faham, S. et al., "Heparin structure and interactions with basic fibroblast growth factor," (1996) *Science* 271:1116–1120.

Feingold, H.M. et al., "Coagulation assays and platelet aggregation patterns in human, baboon, and canine blood," (1986) *Am. J. Vet. Res.* 47:2197–2199.

Feng, J. and Chaikof, E.L., "Reconstitution of thrombomodulin into polymerizable phospholipid vesicles," (2000) *Polymer Preprints* 41(2):1653–1654.

Flitsch, S.L., "Chemical and enzymatic synthesis of glycopolymers," (Dec. 2000) *Current Opinion in Chem. Biol.* 4(6):619–625.

Florin, E.L. and Gaub, H.E., "Painted supported lipid membranes," (1993) *Biophys J.* 64:375–383.

Fong, J. et al., "Beaded nanofibers formed during electrospinning," (1999) *Polymer* 40: 4585–4592.

Foster, J.A. et al., "Isolation and amino acid sequences of tropoelastin peptides," (1973) *J. Biol. Chem.* 24:2876–2879.

Frank, M. and Ries, L.F., "The role of complement in the inflammation and phagocytosis," (1991) *Immunol. Today* 12:322–326.

Franzblau, C. et al., "Role of crosslinking in fiber formation," (1977) *Adv. Exp. Med. Biol.* 79:313–327.

Galvin, J.B. et al., "Reconstitution of rabbit thrombomodulin into phospholipid vesicles," (1987) *J. Biol. Chem.* 262(5):2199–2205.

Gemmell, C.H. et al., "The effects of shear rate on the enzymatic activity of the tissue factor—factor VIIa complex," (1990) *Microvasc. Res.* 40(30):327–340.

Gemmell, C.H. et al., "Utilization of a continuous flow reactor to study the lipoprotein–associated coagulation inhibitor (LACI) that inhibits tissue factor," (1990) *Blood* 76(11):2266–2271.

Gentry, R. et al., "Surface–mediated enzymatic reactions: simulations of tissue factor activation of factor X on a lipid surface," (1995) *Biophys. J.* 69(2):362–371.

Gerling, I. et al., "Multiple low–dose streptozocin–induced diabetes in NOD–scid/scid mice in the absence of functional lymphocytes," (1994) *Diabetes* 43:433–440.

Gill, R.G. et al., "CD4$^+$ T cells are both necessary and sufficient for islet xenograft rejection," (1994) *Transplantation Proceedings* 26:1203.

Gir, S. et al., "A numerical analysis of factor X activation in the presence of tissue factor—factor VIIa complex in a flow reactor," (1996) *Ann. Biomed. Eng.* 24(3):394–399.

Gnanou, Y. et al., "Synthesis of star–shaped poly(ethylene oxide)," (1998) *Makromol. Chem.* 189:2885–2892.

Goeden–Wood, N.L. et al., "Improved assembly of multimeric genes for the biosynthetic production of protein polymers," (Jul.–Aug. 2002) *Biomacromolecules*. 3(4):874–879.

Golden, M.A., "Healing of polytetrafluoroethylene arterial grafts is influenced by graft porosity," (1990) *J. Vascular Surgery* 11(6):838–844.

Goldsmith, H.L. and Turitto, V.T., "Rheological aspects of thrombosis and haemostasis: basic principles and applications," (1986) *Thromb. Haemostasis* 55(3):415–435.

Goosen, M.F.A. (1985), Optimization of microencapsulation parameters: semipermeable microcapsules as a bioartificial pancreas, *Biotech. Bioeng.* 27:146–150.

Goosen, M.F.A. et al., "Inactivation of thrombin by antithrombin III on a heparinized biomaterial," (1980) *Thrombosis Research* 20(5/6):543–554.

Grande, D. et al., "Glycosaminoglycan mimetic biomaterials. 2. Alkene– and acrylate–derivatized glycopolymers via cyanoxyl–mediated free–radical polymerization," (2001) *Macromolecules* 34:1640–1646 (tentatively published on Web Feb. 13, 2001).

Grande, D. et al., "Glycoaminoglycan mimetic biomaterials. 1. Nonsulfated and sulfated glycopolymers by cyanoxyl–mediated free–radical polymerization," (2000) *Macromolecules* 33:1123–1125.

Grande, D. et al., "Synthesis of non–sulfated and sulfated glycopolymers," (2000) *Polymer Preprints* 41(1):1000–1001.

Gray, W.R. et al., "Molecular model for elastin structure and function," (1973) *Nature* 246:461–466.

Gruber, A. et al., "Antithrombotic effects of combining activated protein C and urokinase in nonhuman primates," (1991) *Circulation* 84(6):2454–2462.

Gruber, A et al., "Inhibition of thrombus formation by activated recombinant protein C in a primate model of arterial thrombosis," (1990) *Circulation* 82(2):578–585.

Gruber, A. et al., "Inhibition of platelet–dependent thrombus formation by human activated protein C in a primate model," (1989) *Blood* 73(3):639–742.

Hall et al., "Factor Xa generation at the surface of cultured rat vascular smooth muscle cells in an in vitro flow system," (1998) *J. Biomech. Eng.* 120(4):484–490.

Hall, B. et al., "Biomembranes as models for polymer surfaces," (1989) *Biomaterials* 10(4):219–224.

Halle I., et al. (1993) "Protection of islets of Langerhans from antibodies by microencapsulation with alginate––poly–L–lysine membranes," *Transplantation*, 44:350–4.

Hanson, S.R. et al., "Blood flow and antithrombotic drug effects," (1998) *Am. Heart Journal* 135(5 Pt 2 Su):S132–145.

Hanson, S.R. et al., "Antithrombotic effects of thrombin–induced activation of endogenous protein C in primates," (1993) *J. Clin. Invest.* 92(4):2003–2012.

Hanson, S.R. et al., "Effects of angiotensin converting enzyme inhibition with cilazapril in intimal hyperplasia in injured arteries and vascular grafts in the baboon," (1991) *Hypertension* 18(4Suppl):II–70—II–76.

Hanson, S.R. et al., "Platelet interactions with Dacron vascular grafts; a model of acute thrombosis in baboons," (1985) *Arteriosclerosis* 5(6):595–603.

Harker, L.A. et al., "Effects of megakaryocyte growth and development factor on platelet production, platelet life span, and platelet function in healthy human volunteers," (Apr. 2000) *Blood* 95(8):2514–2522.

Hasegawa, T. et al., "Quantitative analysis of uniaxial molecular orientation in Langmuir–Blodgett films by infrared relection spectroscopy," (1995) *Langmuir* 11:1236–1243.

Haskins, K. and McDuffe, M. (1990), "Acceleration of diabetes in young NOD mice with CD4$^+$ islet–specific T cell clone," *Science* 249:1433–1436.

Hayashi, C.Y. et al., "Hypotheses that correlate the sequence, structure, and mechanical properties of spider silk proteins," (1999) *Int. J. Biol. Macromol.* 24:271–275.

Hayashi, C. Y. and Lewis, R. V., "Evidence from flagelliform silk cDNA for the structural basis of elasticity and modular nature of spider silks," (1998) *J. Mol. Biol.* 275: 773–84.

Hayward, J.A. et al., "Biomembranes as models for polymer surfaces," (1986) *Biomaterials* 7:252–258.

Hayward, J.A. and Chapman, D., "Biomembrane surfaces as models for polymer design: the potential for haemocompatibility," (1984) *Biomaterials* 5:135–142.

Hayzer, D.J et al., "cDNAs encoding the baboon thrombin receptor indicate a primate transcription start site upstream of putative sites reported for the human gene," (1999) *Throm. Res.* 98:195–201.

Hayzer, D.J. et al., "Characterization of a cDNA encoding the β–chain of baboon receptor glycoprotein BPIb," (1993) *Gene* 127:271–272.

Hérbert, N. et al., "A new reagent for the removal of the 4–methozybenzyl ether: application to the synthesis of unusual macrocyclic and bolaform phosphatidytcholines," (1992) *J. Org. Chem.* 57:1777–1783.

Helm, C.A. et al., "Measurement of ligand–receptor interactions," (1991) *Proc. Natl. Acad. Sci. USA* 88:8169–8173.

Hergenrother, P.J. et al., "Small–molecule microarrays: covalent attachment and screening of alcohol–containing small molecules on glass slides," (2000) *J. Am. Chem. Soc.* 122:7849–7850.

Heroguez, V. et al., "Novel amphiphilic architectures by ring–opening metathesis polymerization of macromonomers," (1997) *Macromolecules* 30:4791–4798.

Huang, L. et al., "Generation of synthetic elastin–mimetic small diameter fibers and fiber networks," (2000) *Macromolecules* 33: 2989–2997 (published on Web Mar. 24, 2000).

Hubbell, J.A. et al., "Endothelial cell–selective materials for tissue engineering in the vascular graft via a new receptor," (1991) *Bio/Technology* 9:568–572.

Hudson, S.M., "The spinning of silk–like proteins into fibers," *Protein–Based Materials*, McGrath, K. and Kaplan, D., Ed.: Birkhauser: Boston, 1997, pp. 313–337.

Ishihara, K., "Novel polymeric materials for obtaining blood–compatible surfaces," (1997) *TRIP* 5(12):401–407.

Ishihara, K. et al., "Synthesis of phospholipid polymers having a urethane bond in the side chain as coating material on segmented polyurethane and their platelet adhesion–resistant properties," (1995) *Biomaterials* 16:873–879.

Ishihara, K. et al., "Hemocompatibility on graft copolymers composed of poly(2–methacryloyloxyethyl phosphorylcholine) side chain and poly(n–butyl methacrylate) backbone," (1994) *J. Biomed. Mater. Res.* 28:225–232.

Ishihara, K. et al., "Hemocompatibility of human whole blood on polymers with a phospholipid polar group and its mechanism," (1992) *J. Biomed Mat. Res.* 26:1543–1552.

Ishihara, K. et al., "Reduced thrombogenicity of polymers having phospholipid polar groups," (1990) *J. Biomed Mat. Res.* 24:1069–1077.

Ito Y., Section/Chapter 5.2, "Cell growth factor immobilized materials," p. 285–310; in Imanishi, Y. 1992. Synthesis of Biocomposite Materials: Chemical and Biological Modified Natural Polymers. Boca Raton, FL, CRC Press, 314 p. ISBN 0849367719.

Jackson, R.L. et al., "Glycosaminoglycans: molecular properties, protein interactions, and role in physiological processes," (1991) *Physiol. Rev.* 71(2):481–539.

Janeway, C. and Bottomly, K., "Signals and signs for lymphocyte responses," (1994) *Cell* 76:275–285.

Jarpe, A.J. et al., "Flow cytometric enumeration of mononuclear cell populations infiltrating the islets of Langerhans in prediabetic NOD mice: Development of model of autoimmune insulinitis for Type I diabetes," (1990) *Regional Immunology* 3:305–317.

Kagan, H.M. et al., "Repeat polypeptide models of elastin as substrates for lysyl oxidase," (1980) *J. Biol. Chem.* 255:3656–3659.

Kalafatis, M. et al., "Regulation and regulatory role of γ–carboxyglutamic acid containing clotting factors," (1996) *Critical Reviews in Eukaryotic Gene Expression* 6(1):87–101.

Kalafatis, M. et al., "The regulation of clotting factors," (1997) *Crit. Rev. Eukaryotic Gene Expression* 7(3):241–280.

Kawamoto et al., "Reconstituted collagen is not capable of activating factor XII but causes intrinsic coagulation by activating platelets," (1992) *Blood Coagulation & Fibrinolysis* 3(4):371–379.

Ke, Y. et al., "Ovalbumin injected with complete Freund's adjuvant stimulates cytolytic responses," (1995) *Eur. J. Immunol.* 1995:549–553.

Khaled, Md. A. et al., "Proton magnetic resonance and conformational energy calculations of repeat peptides of tropoelastin: the tetrapeptide," (1976) *J. Am. Chem. Soc.* 98:7547–7553.

Kim, D.H. et al., "The influence of tiered layers of surface–grafted poly(ethylene glycol) on receptor–ligand–mediated adhesion between phospholipid monolayer–stabilized microbubbles and coated glass beads," (2000) *Langmuir* 16:2808–2817.

Kim, H.S. et al., "Characterizing structural changes in point–bonded nonwoven fabrics during load–deformation experiments," (Feb. 2001) *Textile Res. J.* 71(2):157–164.

Kimura, T. et al., "High–resolution solid–state $^{13}C$ nuclear magnetic resonance study of the combined process of $^1H$ spin diffusion and $^1H$ spin–lattice relaxation in semicrystalline polymers," (1992) *Polymer* 33(3):493–497.

King, G.A. et al (1987), "Alginate–polylysine microcapsules of controlled membrane molecular weight cutoff for mammalian cell culture engineering," *Biotech Progress* 3:231–240.

Kishida, A. et al., "In vivo and ex vivo evaluation of the antithrombogenecity of human thrombomodulin immobilized biomaterials," (1995) *ASAIO Journal* 41:M369–374.

Kishida, A. et al., "Immobilization of human thrombomodulin onto biomaterials," (1994) *ASAIO Journal* 40(3):M840–845.

Kishida, A. et al., "Immobilization of human thrombomodulin on biomaterials: evaluation of the activity of immobilized human thrombomodulin," (1994) *Biomaterials* 15(14):1170–1174.

Kishida, A. et al., "Immobilization of human thrombomodulin onto poly(ether urethane urea) for developing antithrombogenic blood–contacting materials," (1994) *Biomaterials* 15(10):848–852.

Kobayashi, T. et al., "Theory of the kinetics of reactions catalyzed by enzymes attached to membranes," (1974) *Biotech. Bioeng.* 16(1):77–97.

Kobayashi, T. et al., "Theory of the kinetics of reactions catalyzed by enzymes attached to the interior surfaces of tubes," (1974) *Biotech. Bioeng.* 16(1):99–118.

Köhler, A.S. et al., "Platelet adhesion to novel phospholipid materials: modified phosphatidylcholine covalently immobilized to silica, polypropylene, and PTFE materials," (1996) *J. Biomed. Mat. Res.* 32:237–242.

Kojima, M. et al., "Interaction between phospholipids and biocompatible polymers containing a phosphorylcholine moiety," (1991) *Biomaterials* 12:121–124.

Korbutt, G.S. et al., "Large scale isolation, growth, and function of porcine neonatal islet cells," (1996) *J. Clin. Invest.* 97(9):2119–2129.

Korbutt, G.S. et al., "Porcine islet cell antigens are recognized by xenoreactive natural human antibodies of both IgG and IgM subtypes," (1995) *Transplantation Proceedings* 28:821–823.

Korbutt, G.S. et al., "Successful reversal of diabetes in nude mice by transplantation of microencapsulated porcine neonatal islet cell aggregates," (1995) *Transplantation Proceedings* 27:3212.

Krejchi, M.T. et al., "Chemical sequence control of β–sheet assembly in macromolecular crystals of periodic polypeptides," (1994) *Science* 265:1427–1432.

Krych, M. et al., "Complement receptors," (1992) *Curr. Opin. Immunol.* 4:8–13.

Kuhlenschmidt, T.B. and Lee, T.C., "Specificity of chicken liver carbohydrate binding protein," (1983) *Biochem.* 23(16):3569–3575.

Kühner, M. et al., "Lipid mono– and bilayer supported on polymer films: composite polymer–lipid films on solid substrates," (1994) *E. Biophys. J.* 67:217–226.

Lamparski et al. (1983) *J. Am. Chem. Soc.* 11:8096–8102.

Lamparski, J. et al., "Photoinduced destabilization of liposomes," (1992) *Biochemistry* 31:685–694.

Laster, J. and Silver, D., "Heparin–coated catheters and heparin–induced thrombocytopenia," (1988) *J. Vasc. Surg.* 7(5):667–672.

Lee, T.A.T. et al., "Thermo–reversible self–assembly of nanoparticles derived from elastin–mimetic polypeptides," (Aug. 2000) *Advanced Materials* 12(15):1105–1110.

Lenschow, D. et al. (1992), "Long–term survival of xenogenic pancreatic islet grafts induced by CTLA4Ig," *Science* 257:789–795.

Lim, F. and Sun, A.M. (1980), Microencapsulated islets as a bioartificial endocrine pancreas, *Science* 210:908–910.

Lindhout, T. et al., "Antithrombin activity of surface–bound heparin studied under flow conditions," (1995) *J. Biomed. Mater. Res.* 29(10):1255–1266.

Lindner, V. et al., "Basic fibroblast growth factor stimulates endothelial regrowth and proliferation in denuded arteries," (1990) *J. Clin. Invest.* 85:2004–2008.

Loudovaris, T. et al. (1992), "The role of T cells in the destruction of xenografts within cell impermeable membranes" *Transplantation Proceedings* 24:2938.

Loykulnant, S. and Hirao, A., "Protection and polymerization of functional monomers. 30. Anionic living polymerization of 4–alkylstyrenes containing acetal–protected monosaccharide residues," (2000), *Macromolecules* 33:4757–4764.

Loykulnant, S. et al., "Protection and polymerization of functional monomers. 28. Anionic living polymerization of styrene derivatives containing acetal–protected monosaccharide residues," (1998) *Macromolecules* 31:9121–9126.

Lu, D. et al., "Comparison of activated protein C/protein S–mediated inactivation of human factor VIII and facor V," (1996) *Blood* 87(11):4708–4717.

Lvov, Y. et al., "Assembly, structural characterization, and thermal behavior of layer–by–layer deposited ultrathin films of poly(vinyl sulfate) and poly(allylamine)," (1993) *Langmuir* 9:481–486.

MacDonald, R.C. et al., "Small–volume extrusion apparatus for preparation of large, unilamellar vesicles," (1991) *Biochim. Biophys. Acta* 1061:297–303.

Mann, K.G. et al., "Cofactor proteins in the assembly and expression of blood clotting enzyme complexes," (1988) *Ann. Rev. Biochemistry* 57:915–956.

Mao, G., et al., "Interactions, structure, and stability of photoreactive bolaform amphiphile multilayers," (1995) *Langmuir* 11:942–952.

Maoz et al. (1984) "On the formation and structure of self–assembling monolayers," *J. Colloid Interface Sci.* 100(2):456.

Markovich, R.J. et al., "Silica subsurface amine effect on the chemical stability and chromatographic properties of end–capped immobilized artificial membrane surfaces," (1991) *Anal. Chem.* 63:1851–1860.

Marra, K.G. et al., "Cytomimetic biomaterials. 1. In–Situ polymerization of phospholipids on an alkylated surface," (1997) *Macromolecules* 30:6483–6488.

Marra, K.G. et al., "Cytomimetic biomaterials. 2. In–Situ polymerization of phospholipids on a polymer surface," (1997) *Langmuir* 13:5697–5701.

Marra, K.G. et al., "Stabilized phosphatidylcholine surfaces via in–situ polymerization at a solid–liquid interface," (1997) *Polymer Preprints* 38(2):682–683.

Marsh, A. et al., "Atom transfer polymerization: use of uridine and adenosine derivatized monomers and initiators," (1999) *J. Macromolecules* 32:8725–8731.

Martin, D.C. et al., "Processing and Characterization of Protein Polymers," *Protein–Based Materials*, McGrath, K. and Kaplan, D., Eds.; Birkhauser: Boston, 1997, pp. 339–370.

Martin, S.F. et al., "General method for the synthesis of phospholipid derivatives of 1,2–O–diacyl–sn–glycerols," (1994) *J. Org. Chem.* 59:4805–4820.

Massia, S.P. and Hubbell, J.A., "Vascular endothelial cell adhesion and spreading promoted by the peptide REDV of the IIICS region of plasma fibronectin is mediated by integrin $\alpha_2\beta_1$," (1992) *J. Biol. Chem.* 267:14019–14026.

Matthew, H.W. et al (1993) "Complex coacervate microcapsules for mammalian cell culture and artificial organ development," *Biotechnol. Prog.* 9:510–519.

Mauk, A.W. et al., "Structural characterization of self–assembled lipid monolayers by N$\pi$T simulation," (1998) *Langmuir* 14:5255–5266.

Mauk, M.R. et al., "Vesicle targeting: timed release and specificity for leukocytes in mice by subcutaneous injection," (1980) *Science* 207:309–311.

McLean, L.R. et al., "Preparation of stable polar surfaces using polymerizable long–chain diacetylene molecules," (1983) *Thin Solid Films* 99:127–131.

McMillan R.A. and Conticello, R. P., "Synthesis and characterization of elastin–mimetic protein gels derived from a well–defined polypeptide precursor," (2000) *Macromolecules* 33:4809–4821.

McMillan, R.A. et al., "High–resolution topographic imaging of environmentally responsive, elastin–mimetic hydrogels," (1999) *Macromolecules* 32:9067–9070.

McMillan, R.A. et al., "Rapid assembly of synthetic genes encoding protein polymers," (1999) *Macromolecules* 32:3643–3648.

McPherson, D.T. et al., "Product purification by reversible phase transition following *Eschericia coli* expression of genes encoding up to 251 repeats of the elastomeric pentapeptide GVGVP," (1996) *Protein Expression Purification* 7:51–57.

McPherson, D.T. et al., "Production and purification of a recombinant elastomeric polypeptide, G–(VPGVG)$_{19}$–VPGV, from *Escherichia coli*, " (1992) *Biotechnology Progress* 8:347–352.

Merrill, E.W. et al., "Polyvinyl alcohol–heparin hydrogel 'G'," (1970) *J. Applied Physiology* 29(5):723–730.

Meuse, C. W. et al., "Hybrid bilayer membranes in air and water: infrared spectroscopy and neutron reflectivity studies," (1998) *Biophys J.* 74:1388–1398.

Mielczarski, J.A. and Yoon, R.H., "Fourier transform infrared external reflection study of molecular orientation in spontaneously adsorbed layers on low–absorption substrates," (1989) *J. Phys. Chem.* 93:2034–2038.

Miller, B. et al., "Both the Lyt–$2^+$ and L3T$4^+$ T cell subsets are required for the transfer of diabetes in nonobase diabetic mice" (1988) *J. Immunol.* 140:52–8.

Minoda, M. et al., "Synthesis of functional polymers bearing pendant mono– and oligo– saccharide residues," *Macromol. Symp.* 99:169–177 (1995).

Miyata, T. and Nakamae, K., "Polymers with pendent saccharides—'glycopolymers'," (1997) *Trends Polym. Sci.* 5:198–206.

Miyoshi, M. et al., "A rapid formation of lysine–derived crosslinks by chick embryo aorta," (1976) *J. Biochem. (Tokyo)* 79:235–1243.

Monshipouri, M. and Rudolph, A.S., "Liposome–encapsulated alginate: controlled hydrogel particle formation and release," (1995) *J. Microencapsulation* 12(2):117–127.

Moore et al., (1983) *Macromolecules* 16:335–338.

Moses, R. et al., (1990), "Xenogeneic proliferation and lymphokine production are dependent upon CD4+ helper T cells and self antigen–presenting cells in the mouse. I," *Exp. Med.* 172:567–75.

Moya, S. et al., "Lipid coating on polyelectrolyte surface modified colloidal particles and polyelectrolyte capsules," (2000) *Macromolecules* 33:4538–4544.

Müller–Eberhard, H.I., "Molecular organization and function of the complement system," (1988) *Ann. Rev. Biochem.* 57:321–347.

Nagahori, N. and Nishimura, S–I., "Tailored glycopolymers: controlling the carbohydrate–protein interaction based on template effect," (2001) *Biomacromolecules* 2:22–24 (published on Web Dec. 28, 2000).

Nagle, J.F. et al., "X–ray structure determination of fully hydrated $L_\alpha$ phase dipalmitoylphosphatidylcholine bilayers," (1996) *Biophys. J.* 70:1419–1431.

Nah, J–W et al., "Polymeric micelle formation of multiblock copolymer composed of poly($\gamma$–benzyl L–glutamate) and poly(ethylene oxide)," (2000) *Bull. Korean Chem. Soc.* 21(4):383–388.

Nah, J–W et al., Drug–delivery system based on core–shell–type nanoparticles composed of poly($\gamma$–benzyl L–glutamate) and poly(ethylene oxide), (2000) *J. App. Polymer Sci.* 75:115–1126.

Nemerson, Y. and Turitto, V.T., "The effect of flow on hemostasis and thrombosis," (1991) *Thromb. Haemostasis* 66(3):272–276.

Nickerson, P. et al., "Analysis of cytokine transcripts in pancreatic islet cell allografts during rejection and tolerance induction," (1993) *Transplantation Proceedings* 25:984–985.

Nojiri, C. et al., "Can heparin immobilized surfaces maintain nonthrombogenic activity during In Vivo long–term implantation?" (1996) *ASAIO Journal* 42(5):M468–475.

Nojiri, C. et al., "In vivo nonthrombogenicity of heparin immobilized polymer surfaces," (1990) *ASAIO Transactions* 36(3):M168–172.

Nomura, K. and Schrock, R.R., "Preparation of 'sugar–coated' homopolymers and multiblock ROMP copolymers," (1996) *Macromolecules* 29:540.

O'Brien, D.F. et al., "Polymerization of preformed self–organized assemblies," (1998) *Acc. Chem. Res.* 31:861–868.

O'Connell, P.J. et al., "Unmodified pancreatic islet allograft rejection results in the preferential expression of certain T cell activation transcripts," (1993) *J. Immunol.* 150:1093–1104.

O'Donnell, J. H. and Whittaker, A. K., "Radiation degradation of linear low density polyethylene: determination of lamellae thickness, crystallinity and crosslinking by solid–state $^{13}$C NMR and DSC," (1992) *Radiat. Phys. Chem.* 36(20:209–214.

O'Donnell, J. H. and Whittaker, A. K., "A solid–state $^{13}$C–NMR study of crosslinking in polybutadiene by $\gamma$ radiation: effect of microstructure and dose," (1992) *J. Polym. Chem. Ed.* 30:185–195.

Ohno, K. et al., "Nitroxide–controlled free radical polymerization of a sugar–carrying acrytoyl monomer," (1999) *Macromol. Chem. Phys.* 200:1619–1625.

Ohno, K. et al., "Synthesis of a well–defined glycopolymer by nitroxide–controlled free radical polymerization," (1998) *Macromolecules* 31:1064.

Ohno, K. et al., "Synthesis of a well–defined glycopolymer by atom transfer radical polymerization," (1998) *J. Polym. Sci., Part A: Polym. Chem.* 36:2473–2481.

Ohno, K. et al., "Free radical polymerization of a sugar residue–carrying styryl monomer with a lipophilic alkoxyamine initiator: synthesis of a well–defined novel glycolipid," (1998) *Macromol. Chem. Phys.* 199:2193–2197.

Ohno, H. et al., "Polymerization of liposomes composed of diene–containing lipids by UV and radical initiators: evidence for the different chemical environment of diene groups on 1– and 2–acyl chains," (1987) *Macromol.* 20:929–933.

Ohno, H. et al., "Polymerization of liposomes composed of diene–containing lipids by radical initiators. II. Polymerization of monodiene–type lipids as liposomes," (1987) *J. Polym. Sci.: Part A: Polym. Chem.* 25:2737–2746.

Orban, J.M. et al., "Cytomimetic biomaterials. 4. In–situ photo polymerization of phospholipids on an alkylated surface," (2000) *Macromolecules* 33:4205–4212 (published on Web May 6, 2000).

Omitz, D.M. et al., "FGF binding and FGF receptor activation by synthetic heparan–derived di– and trisaccharides," (1995) *Science* 268:432–434.

Otani et al., "Rapidly curable biological glue composed of gelatin and poly(L–glutamic acid)," (1996) *Biomaterials* 17(14):1387–1391.

Owen, W.G. and Esmon, C.T., "Functional properties of an endothelial cell cofactor for thrombin–catalyzed activation of protein C," (1981) *J. Biol. Chem.* 256(11):5532–5535.

Packer, K. J. et al., "The effects of morphology on $^1$H NMR spectra and relaxation in semicrystalline polyolefins," (1984) *J. Polym. Sci.: Polym. Phys.* 22:589–616.

Panitch, A. et al., "Design and biosynthesis of elastin–like artificial extracellular matrix proteins containing periodically spaced fibronectin CS5 domains," (1999) *Macromolecules* 32:1701–1703.

Parikh, A.N. et al., "An intrinsic relationship between molecular structure in self–assembled n–alkysiloxane monolayers and deposition temperature," (1994) *J. Phys. Chem.* 98:7577.

Parker, W. et al., "Transplantation of discordant xenografts: a challenge revisited," (1996) *Immunology Today* 17:373–378.

Pasquali–Ronchetti et al., "Study of elastic fiber organization by scanning force microscopy," (1998) *Matrix Biology* 17:75–83.

Pasquali–Ronchetti et al., "Ultrastructure of elastin," (1995) *Ciba Foundation Symposium* 192:31–50.

Pearce, K.H. et al., "Comparison of the membrane binding kinetics of bovine prothrombin and its fragment 1," (1993) *J. Biol. Chem.* 268:22984–22991.

Peterson, I.D., and Haskins, K. (1996), "Transfer of diabetes in the NOD–scid mouse by CD4 T–cell clones: differential requirement for CD8 T–cells," *Diabetes* 45:328–36.

Petka, W.A. et al., "Reversible hydrogels from self–assembling artificial proteins," (1998) *Science* 281:389–392.

Petitou, M. et al., "Synthesis of thrombin–inhibiting heparin mimetics without side effects," (1999) *Nature* 398:417–422.

Petitou, M. et al., "First synthetic carbohydrates with the full anticoagulant properties of heparin," (1998), *Chem. Int. Ed.* 37:3009–3014.

Pierson, R. et al., (1989), "CD4+ lymphocytes play a dominant role in murine xenogeneic responses," *Transplantation Proceedings* 21:519.

Plant, A.L. et al., "Phospholipid/alkanethiol bilayers for cell–surface receptor studies by surface plasmon resonance," (1995) *Anal. Biochem.* 226:342–348.

Plant, A. L., "Self–assembled phospholipid/alkanethiol biomimetic bilayers on gold," (1993) *Langmuir* 9: 2764–2767.

Plant, A.L. et al., "Generic liposome reagent for immunoassays," (1989) *Anal. Biochem.* 176:420–426.

Ponpipom, M.M. and Bugianesi, R.L., "Isolation of 1,3–distearoyl–glycero–2–phosphocholine (β–lecithin) from commercial 1,2–distearoyl–sn–glycero–3–phosphocholine," (1980) *Lipid Res.* 21:136–139.

Pourdeyhimi, B. et al., "Measuring fiber diameter distribution in nonwovens," (1999) *Textile Res. J.* 69:233–236.

Qiu, Z–H. and Leslie, C.C., "Protein kinase C–dependent and –independent pathways of mitogen–activated protein kinase activation in macrophages by stimuli that activate phospholipase $A_2$," (1994) *J. Biol. Chem.* 269:19480–19487.

Rand, M.D. et al., "Blood clotting in minimally altered whole blood," (1996) *Blood* 88(9):3432–3445.

Rapaka, R.S. et al., "Non–elastomeric polypeptide models of elastin," (1978) *Int. J. Pept. Protein Res.* 11:109–127.

Regen, S.L. et al., "Polymer–supported membranes. A new approach for modifying polymer surfaces," (1983) *Macromolecules* 16:335–338.

Reneker, D.H. and Chun, I., "Nanometre diameter fibres of polymer, produced by electrospinning," (1996) *Nanotechnology* 7:216–223.

Reneker, D.H. and Srinivasan, G., "Electrospun polyaramid fibers: structure and morphology," (1995) *Bull Am. Phys. Soc.* 40:351.

Rifkin, D.B. and Moscatelli, D., "Recent developments in the cell biology of basic fibroblast growth factor," (1989) *J. Cell. Biol.* 109:1–6.

Ringsdorf et al., "Molecular architecture and function of polymeric oriented systems: models for the study of organization, surface recognition, and dynamics of biomembranes," (1988) *Angew. Chem. Int. Ed. Engl.* 27:113–158.

Roach, M.R. and Burton A.C., "The reason for the shape of the distensibility curves of arteries," (1957) *Can. J. Biochem. Physiol.* 35:681–690.

Roberts, I. et al. (1996), "Dopamine secretion by PC12 cells microencapsulated in a hydroxymethyl methacrylate–methyl methacrylate copolymer," *Biomaterials* 17:267–275.

Robins, S. P., "Analysis of the crosslinking components in collagen and elastin," (1982) *Methods Biochem. Anal.* 28:329–379.

Rosen, E.M. et al., "Regulation of motility in bovine brain endothelial cells," (1991) *J. Cell Physiol.* 146:325–35.

Roy, B.C. et al., "Synthesis and fluorescence properties of new fluorescent, polymerizable, metal–chelating lipids," (2000) *J. Org. Chem.* 65:3644–3651.

Roy, R., "Recent developments in the rational design of multivalent glycoconjugates," (1997) *Topics in Current Chem.* 187:241–274.

Roy, R., "Syntheses and some applications of chemically defined multivalent glycoconjugates," (1996) *Current Opinion in Structural Biology* 6:692–702.

Sabatani, E. and Rubinstein, I., "Organized self–assembly monolayers on electrodes. 2. Monolayer–based ultramicroelectrodes for the study of very rapid electrode kinetics," (1987) *J. Phys. Chem.* 91:6663–6669.

Sackmann, E. and Tanaka, M., Supported membranes on soft polymer cushions: fabrication, characterization and applications, (2000) *Trans Biotechnol.* 18:58–64.

Sadler, J.E., "Thrombomodulin structure and function," (1997) *Thromb. Haemostasis* 78(1):392–395.

Sakai, H. and Umemura, J., "Molecular orientation in Langmuir films of 12–hydroxystearic acid studied by infrared external–reflection spectroscopy," (1998) *Langmuir* 14:6249–6255.

Sakata, Y., et al., "Activated protein C stimulates the fibrinolytic activity of cultured endotheliat cells and decreases antiactivator activity," (1985) *Proc. Natl. Acad. Sci. USA* 82(4):1121–1125.

Sandberg, L.B. et al., "Elastin covalent structure as determined by solid phase amino acid sequencing," (1985) *Pathol. Biol.* 33:266–274.

Sandberg, L.B. et al., "Elastin structure, biosynthesis, and relation to disease states," (1981) *N. Engl. J. Med.* 304:566–579.

Sandberg, L.B. et al., "Primary structure of porcine tropoelastin," (1977) *J. Adv. Exp. Med. Biol.* 79:277–284.

Santin, M. et al., "Synthesis and characterization of a new interpenetrated poly(2–hydroxyethylmethacrylate)–gelatin composite polymer," (1996) *Biomaterials* 17(15):1459–1467.

Sato, Y. and Rifkin, D.B., "Autocrine activities of basic fibroblast growth factor: regulation of endothelial cell movement, plasminogen activator synthesis, and DNA synthesis," (1988) *J. Cell. Biol.* 107:1199–1205.

Schmidt, R.R., "Recent developments in the synthesis of glycoconjugates," (1989) *Pure Appl. Chem.* 61(7):1257–70.

Sefton, M.V., (1989), *Can. J. Chem. Eng.* 67:705–712.

Seifert, K. et al., "Charge transport by ion translocating membrane proteins on solid supported membranes," (1993) *Biophys. J.* 64:384–391.

Seitz, M. et al., "Formation of tethered supported bilayers via membrane–inserting reactive lipids," (1998) *Thin Solid Films* 329:767–771.

Sells, T.D. & O'Brien, D.F., "Two–dimensional polymerization of lipid bilayers: degree of polymerization of acryloyl lipids," (1994) *Macromolecules* 27:226–233.

Serruys, P.W. et al., "Randomised comparison of implantation of heparin–coated stents with balloon angioplasty in selected patients with coronary artery disease (Benestent II)," (1998) *Lancet* 352:673–681.

Shen, W. W. et al., "Polymer–supported lipid bilayers on benzophenone–modified substrates," (2001) *Biomacromolecules* 2:70–79.

Shi, X. and Caruso, F., "Release behavior of thin–walled microcapsules composed of polyelectrolyte multilayers," (2001) *Langmuir* 17:2036–2042.

Shoji, M. et al., "Human and baboon integrin $β_5$ subunit–encoding mRNAs have alternative polyadenylation sites," (1993) *Gene* 133:307–308.

Shultz, L. et al., "Multiple defects in innate and adaptive immunologic function in NOD/LtSz–scid mice," (1995) *J. Immunology* 154:180–191.

Siedlecki, C.A. et al., "Interactions of human von Willebrand factor with a hydrophobic self–assembled monolayer studies by atomic force microscopy," (1994) *Biomed. Mater. Res.* 28;971.

Slack, S.M. et al., "The effects of flow on blood coagulation and thrombosis," (1993) *Thromb. Haemostasis* 70(1):129–134.

Slack, S.M. and Turitto, V.T., "Flow chambers and their standardization for use in studies of thrombosis," (1994) *Thromb. Haemostasis* 72(5):777–781.

Smirnov, M.D. et al., "The effect of membrane composition on the hemostatic balance," (1999) *Biochemistry* 38(12):3591–3598.

Smirnov, M.D. and Esmon, C.T., "Phosphatidylethanolamine incorporation into vesicles selectively enhances factor VA inactivation by activated protein C," (1994) *J. Biol. Chem.* 269(2):816–819.

Snyder, R.G. et al., "Vibrational spectra in the C–H stretching region and the structure of the polymethylene chain," (1978) *Spectrochim. Acta. Part A* 34A:395–406.

Solletti, J.M. et al., "Elaboration and characterization of phospholipid Langmuir–Blodgett films," (1996) *Langmuir* 1:5379–5386.

Spinke, J. et al., "Polymer–supported bilayer on a solid substrate," (1992) *Biophys. J.* 63:1667–1671.

Stoll, M.S. et al., "Improved procedure for the construction of neoglycolipids having antigenic and lectin–binding activities, from reducing oligosaccharides," (1988) *Biochemical J.* 256:661–664.

Sun, F. et al., "Ultrathin self–assembled polymeric films on solid surfaces. 2. Formation of 11–(n–pentyldithio)undecanoate–bearing polyacrylate monolayers on gold," (1993) *Langmuir* 9:3200–3207.

Sun, F. et al., "Spontaneous polymer thin film assembly and organization using mutually immiscible side chains," (1996) *J. Am. Chem. Soc.* 118:1856–1866.

Sun, F. et al., "Ultrathin self–assembled polymeric films on solid surfaces. III. Influence of acrylate dithioalkyl side chain length on polymeric monolayer formation on gold," (1994) *J. Vac. Sci. Technol.* 12:2499.

Sun, L. and Chaikof, E.L., "The synthesis of neoglycophospholipid conjugates via reductive amination of ω–oxoalkylglycosides and phosphatidylethanolamines," (1998) *Carbohydrate Res.* 370:77–81.

Sun. L. and Chaikof, E.L., "Neoglycophospholipids with alkyl spacers: synthesis via an improved reductive amination and monolayer properties," (1997) *Bioconjugate Chem.* 8:567–571.

Sun, Y. et al. (1996), "Normalization of diabetes in spontaneously diabetic cynomologus monkeys by xenografts of microencapsulated porcine islets without immunosuppression," *J. Clin. Invest.* 98:1417–1422.

Takeuchi, T. et al. (1992), "Heart allografts in murine systems: The differential activation of Th2–like effector cells in peripheral tolerance," *Transplantation* 53:1281–1294.

Tasumi, M.S. and Miyaza, T.J., "Normal vibrations and force constants of polymethylene chain," (1962) *J. Mol. Spectrosc.* 9:261–287.

Tendian, S.W. et al., "Evidence from total internal reflection fluorescence microscopy for calcium–independent binding of prothrombin to negatively charged planar phospholipid membranes," (1991) *Biochemistry* 30:10991–10999.

Terranova, V.P. et al., "Human endothelial cells are chemotactic to endothelial cell growth factor and heparin," (1985) *Cell Biol.* 101:2330–2334.

Thomas, G.J. and Prescott, B., "Raman amide bands of type–II β–turns in cyclo–(VPGVG)$_3$ and poly–(VPGVG), and implications for protein secondary–structure analysis," (1987) *Biopolymers* 26:921–934.

Toshima, K. and Tatsuta, K., "Recent progress on O–glycosylation methods and its application to natural products synthesis," (1993) *Chem. Rev.* 93:1503–1531.

Turitto, V.T and Hall, C.L., "Mechanical factors affecting hemostasis and thrombosis," (1998) *Thromb. Res.* 92(6 Suppl.2):S25–310.

Ueda, T. et al., "Preparation of 2–methacryloyloxyethyl phosphorylcholine copolymers with alkyl methacrylates and their blood compatibility," (1992) *Polym. J.* 24(11):1259–1269.

Uludag, H. and Sefton, M.V., "Metabolic activity and proliferation of CHO cells in hydroxyethyl methacrylate–methyl methacrylate (HEMA–MMA) microcapsules," (1993) *Cell Transplantation* 2:175–182.

Urry, D.W. et al., "Protein–based materials with a profound range of properties and applicaitons: the elastin $\Delta T_1$, hydrophobic paradigm," K. McGrath and D. Kaplan, Ed., Birkhauser: Boston, (1997), pp 133–177.

Urry, D.W. et al., "Molecular biophysics of elastin structure, function and pathology," (1995) *Ciba Foundation Symposium* 192:4–30.

Urry, D.W., "Molecular machines: how motion and other functions of living organisms can result from reversible chemical changes," (1993) *Angew. Chem. Int. Ed. Engl.* 32:819–841.

Urry, D.W. et al., "Two dimensional proton NMR studies on poly(VPGVG) and its cyclic conformational correlate, cyclo(VPGVG)$_3$," (1989) *Biopolymers* 28:819–833.

Urry, D.W., "Entropic elastic processes in protein mechanisms. 1. Elastic structure due to an inverse temperature transition and elasticity due to internal chain dynamics," (1988) *J. Prot. Chem.* 7(1):1–34.

Urry, D.W. et al., "Polytetrapeptide of elastin," (1986) *Int. J. Pept. Protein Res.* 28:649–660.

Urry, D.W. et al., "Polypentapeptide of elastin: temperature dependence of ellipticity and correlation with elastomeric force," (1985) *Biochem. Biophys. Res. Commun.* 130:50–57.

Urry, D.W. et al., "Phase–structure transitions of the elastin polypentapeptide–water system within the framework of composition–temperature studies," (1985) *Biopolymers* 24:2345–2356.

Urry, D.W. et al., "Studies on the conformation and interactions of elastin secondary structure of synthetic repeat hexapeptides," (1975) *Biochim. Biophys. Acta* 393:296–306.

Urry, D.W. et al., "Studies on the conformation and interactions of elastin. Proton magnetic resonance of the repeating pentapeptide," (1974) *Biochemistry* 13:609–616.

van Ackern, F. et al., Ultrathin membranes for gas separation and pervaporation prepared upon electrostatic self–assmebly of polyelectrolytes, (998) *Thin Solid Films* 329:762–766.

Van Boeckel, C.A.A. et al., "the unique antithrombin III binding domain of heparin: a lead to new synthetic antithrombotics," (1993) *Chem. Int. Ed. Engl.* 32(12):1671–1690.

Van Den Bulcke, A.I. et al., "Structural and rheological properties of methacrylamide modified gelatin hydrogels," (2000) *Biomacromolecules* 1:31–38.

Vanderhart, D. L., "Proton spin diffusion as a tool for characterizing polymer blends," (1990) *Makromol. Chem., Macromol. Symp.* 34:125–159.

van't Veer, C. et al., "Inhibitory mechanism of the protein C pathway on tissue factor–induced thrombin generation," (1997) *J. Biol. Chem.* 272(12):7983–7984.

Vasilets, V.N. et al., "Microwave $CO_2$ plasma–initiated vapour phase graft polymerization of acrylic acid onto polytetrafluoroethylene for immobilization of human thrombomodulin," (1997) *Biomaterials* 18(17):1139–1145.

Viitala, T. et al., "Protein immobilization to a partially cross–linked organic monolayer," (2000) *Langmuir* 16:4953–4961.

Walt, R.T. et al., "Human endothelial cell migration: stimulation by a released platelet factor," (1978) *Lab Invest.* 39(5):523–529.

Wang, P. et al., "Synthesis of phospholipid–inhibitor conjugates by enzymatic transphosphatidylation with phospholipase D," (1993) *J. Am. Chem. Soc.* 115:10487–10491.

Wasserman, Z.R. and Salemme, F.R., "A molecular dynamics investigation of the elastomeric restoring force in elastin," (1990) *Biopolymers* 29:1613–1631.

Wasserman, S.R. et al., "The structure of self–assembled monolayers of alkylsiloxanes on silicon: a comparison of results from ellipsometry and low–angle X–ray reflectivity," (1989) *J. Am. Chem. Soc.* 111:5852–5861.

Weber, C.J. et al., "CTLA4–lg prolongs survival of microencapsulated neonatal porcine islet xenografts in diabetic NOD mice," (1997) *Cell Transplantation* 6(5):505–508.

Weber, C.J. et al., "Encapsulated islet iso–, allo–, and xenografts in diabetic NOD mice," (1995) *Transplantation Proceedings* 27:3308–3311.

Weber, C. et al. (1994), "NOD mouse peritoneal cellular response to poly–L–lysine–alginate microencapsulated rat islets," *Transplantation Proceedings* 26:1116–1119.

Weber, C. et al. (1990), "Microencapsulated dog and rat islet xenografts into streptozotocin–diabetic and NOD mice," *Horm. Metab. Res.* 35:219–226.

Weber, C.I. et al. (1990), "The role of $CD4^+$ helper T cells in destruction of microencapsulated islet xenografts in NOD mice," *Transplantation* 49(2):396–404.

Weiner, A.L. et al., (1985), "Liposome–collagen gel matrix: A novel sustained drug delivery system," *J. Pharm. Sci.* 74(9):922–925.

Welsh, E. R. and Tirrell, D. A., "Engineering the extracellular matrix: A novel approach to polymeric biomaterials. I. Control of the physical properties of artificial protein matrices designed to support adhesion of vascular endothelial cells," (2000) *Biomacromolecules* 1:23–30.

Westerduin, P. et al., "Synthesis of tailor–made glycoconjugates showing AT III–mediated inhibition of blood coagulation factors Xa and thrombin," (1996) *Chem. Int. Ed. Engl.* 35:331–333.

Westman, J. et al., "Synthesis and fibroblast growth factor binding of oligosaccharides related to heparin and heparan sulphate," (1995) *J. Carbohydr. Chem.* 14:95–113.

Wick et al., "Unusually large von Willebrand factor multimers increase adhesion of sickle erythrocytes to human endothelial cells under controlled flow," (1987) *J. Clin. Invest.* 80:905–910.

Wilbur, D.S. et al., "Biotin reagents for antibody pretargeting. 4. Selection of biotin conjugates for in vivo application based on their dissociation rate from avidin and streptavidin," (2000) *Bioconjugate Chem.* 11:569–583.

Winger, T.M. et al., "Formation and stability of complex membrane–mimetic monolayers on solid supports," (1999) *Langmuir* 15:3866–3874.

Winger, T.M. and Chaikof, E.L., "Synthesis and characterization of supported phospholipid monolayers: a correlative investigation by radiochemical titration and atomic force microscopy," (1998) *Langmuir* 14:4148–4155.

Winger, T.M. and Chaikof, E.L., "Synthesis and characterization of supported bioactive lipid membranes," In: *Materials Science of the Cell*, A. Plant and V. Vogel (Ed.), MRS Publications, Pittsburgh (1998), pp. 113–118.

Winger, T.M. et al., "Behavior of lipid–modified peptides in membrane–mimetic monolayers at the air/water interface," (1997) *Langmuir* 13:3256–3259.

Winger, T.M. et al. , Lipopeptide conjugates: Biomolecular building blocks for receptor activating membrane–mimetic structures. (1996) *Biomaterials* 17:443–449.

Winger, T.M. et al., "A convenient route to thiol terminated peptides for conjugation and surface functionalization strategies," (1995) *Bioconjug. Chem.* 6:323–326.

Winger, T.M. et al., Purification of synthetic lipopeptide conjugates by liquid chromatography, (1995) *J. Liquid Chromatogr.* 18:4117–4125.

Winger, T.M. et al. (1995) *Biomaterials* 16:443–449.

Wong, J.S. & Yen, Y.S., "Intriguing absorption band behavior of IR reflectance spectra of silicon dioxide on silicon, " (1988) *Appl. Spectrosc.* 42(4):598–604.

Wright, E.R and Conticello, V.P., "Self–assembly of block copolymers derived from elastin–mimetic polypeptide sequences," (Oct. 2002) *Adv. Drug. Deliv. Rev.* 54(8):1057–1073.

Wright, E.R. et al., "Thermoplastic elastomer hydrogels via self–assembly of an elastin–mimetic triblock polypeptide," (Feb. 2002) *Adv. Funct. Mater.* 12:149–154.

Xiao, X–D et al., "Preparation, structure, and mechanical stability of alkylsilane monolayers on mica," (1995) *Langmuir* 11(5):1600–1604.

Yamada, K. et al., "Controlled synthesis of amphiphilic block copolymers with pendant N–acetyl–D–glucosamine residues by living cationic polymerization and their interaction with WGA lectin," (1999) *Macromolecules* 32:3553.

Yamada, K. et al., "Controlled synthesis of glycopolymers with pendant D–glucosamine residues by living cationic polymerization," (1997) *J. Polym. Sci. Part A: Polym. Chem.* 35:751–757.

Yen, Y.–S. and Wong, J. (1989) *J. Phys. Chem.* 93:7208–7216.

Yoshioko, T. et al., "Encapsulation of mammalian cell with chitosan–CMC capsule," (1990) *Biotechnol. Bioeng.* 35:66–72.

Yu, S.M. et al., "Smectic ordering in solutions and films of a rod–like polymer owing to monodisperity of chain length," (1997) *Nature* 389:167–170.

Zhang, H. et al., "Synthesis of 4% glu–containing $Val^1$ and $Ile^1$–polypentapeptides: model protein systems for demonstrating mechanochemical coupling," (1989) *J. Protein Chem.* 8:173–182.

Zierler et al., "Accuracy of duplex scanning for measurement of arterial volume flow," (1992) *J. Vasc. Surg.* 16(4):520–526.

\* cited by examiner

ANTITHROMBOGENIC MEMBRANE MIMETIC COMPOSITIONS AND METHODS

CROSS-REFERENCE TO RELATED APPLICATIONS

This application is filed under 35 U.S.C. 371 and claims priority to International Application No. PCT/US01/12094 of International Filing Date 13 Apr. 2001, which claims priority to U.S. application Ser. Nos. 60/197,072 (filed 13 Apr. 2000) and Ser. No. 60/221,618 (filed 28 Jul. 2000).

ACKNOWLEDGMENT OF FEDERAL RESEARCH SUPPORT

This invention was made, at least in part, with funding from the National Institutes of Health. Accordingly, the United States Government may have certain rights in this invention.

THE BACKGROUND OF THE INVENTION

The field of the present invention is the area of medical prostheses, including artificial blood vessels, and materials and methods for coating same so as to improve performance, especially by minimizing thrombosis.

Atherosclerosis is a serious cause of morbidity and mortality despite advances in preventive measures and pharmacological therapeutics. Nearly 700,000 vascular surgical procedures are preformed each year in the United Stats along with several hundred thousand peripheral and coronary angioplasties. Prosthetic bypass grafts and, more recently, arterial stents and other endovascular prosthesis have been utilized in association with these reconstructive procedures. Although large diameter vascular grafts (at least 6 mm internal diameter) have been successfully developed from polymers such as polytetrafluoroethylene (PTFE) and polyethylene terephthalate, the fabrication of a durable small diameter prosthesis (less than 6 mm internal diameter) remains unresolved. Thrombus formation and restenosis currently limit usefulness of small diameter grafts, and these complications require that the patient endure discomfort, health risks and further medical treatments. Furthermore, while prosthetic bypass grafting can be performed in the infrainguinal position with reasonable short term success, within 5 years 30–60% of these grafts fail. Likewise, restenosis and/or occlusion occur in as many as half of all patients within 6 months of stent placement, depending upon the site and the extent of the disease.

It is recognized that the adverse events leading to the failure of many vascular prostheses are related to maladaptive biological reactions at the blood-material and the tissue-material interfaces. In response to these problems, and particularly thrombosis of the small caliber prosthesis, grafts and stents have been coated with albumin, heparin and prostacyclin analogs, which inhibit the clotting cascade and platelet reactivity, or with relatively inert materials, such as polyethylene oxide. An alternate approach has been to design materials which support the in situ regeneration of an endothelial cell line in order to create a functional arterial substitute with a durable thromboresistant interface. However, strategies based on the coating or derivitization of fr a prosthetic have not overcome the capacity of these same substrates to activate platelets and the coagulation cascade. Thus, in the period prior to complete endothelial regeneration, the surface of a small diameter prosthesis remains at increased risk for thrombus formation. Notwithstanding the recognized difficulties of this approach, including the additional constraints for both selective cell growth and normal endothelial function, a biohybrid strategy does offer the potential for incorporating into a prosthesis at least some of the complex physiological response which nature appears to require in this environment.

The control of thrombus formation on molecularly engineered surfaces is critical in the development of improved small diameter arterial prostheses for use in cardiac, plastic and vascular surgery, as well as in the successful implantation of artificial organs and metabolic support systems. It has been postulated that a clinically durable vascular prosthesis may be achieved by identifying and incorporating actively antithrombogenic mechanisms that operate at the blood-material interface under a range of hemodynamic conditions.

Previous attempts to create antithrombogenic materials have includes those where thrombomodulin was attached to artificial materials including polyethylene, acryloyl-modified polytetrafluoroethylene, poly acrylic-acid modified polyethylene, and cellulosic materials (See. e.g., Kishida et al. (1994) *Biomaterials* 15(10):848–852; Kishida et al. (1994) *Biomaterials* 15(14): 1170–1174; Kishida et al. (1994) *ASAIO Journal* 40(3):M840–845; Vasilets et al. (1997) *Biomaterials* 18(17):1139–1145; Kishida et al. (1995) *ASAIO Journal* 41:M369–374).

There is a longfelt need in the art for a clinically durable small diameter vascular prosthesis so that graft performance is improved, especially with respect to thrombus formation and restenosis associated with the small diameter grafts, with concomitant improvement in patient outcomes and quality of life and in the economic costs of surgical procedures involving implant of prosthetic blood vessels and other prosthetic materials.

SUMMARY OF THE INVENTION

The present invention provides compositions and methods for coating small diameter blood vessel prosthetic materials, blood contacting materials and other implantable medical devices and prosthetics so that the performance of the prosthetics and other devices are less prone to thromboses and less likely to induce inflammatory response in the patient in which the prosthesis or device has been installed. Coating the medical prostheses, blood contacting materials and other devices, especially those formed of PTFE, ePTFE, Dacron and certain other synthetic materials, with stable alkylated materials on hydrated surfaces by sequential complexation of polyelectrolytes followed by surface coating with an oppositely charged amphiphilic polymer containing long chain alkanes is within the scope of the present invention. Stable membrane-mimetic assemblies on alkylated hydrated surfaces can be accomplished by vesicle fusion and then followed by photopolymerization. In situ photopolymerization of a surface assembly of lipids is preferred, and photocrosslinking of the lipid molecules to appropriate functionalities associated with surface bound alkyl chains can also be used in the present invention. Preferably, the lipids are phosphatidylcholine lipids, although other lipids which can be used include, without limitation, phosphatidylethanolamine, ether-based phospholipids and lipid conjugates (e.g., lipopeptide or glycolipid conjugates, such as those described in International Patent Published Application WO 00/000239 and U.S. Pat. No. 6,171,614) can be used along with or instead of phosphatidylcholine phospholipids to enhance the membrane biostability and/or bioactivity of thrombomodulin or other antithrombotic proteins. It is desirable that the lipids contain at least one polymerizable group (e.g., mono- or bis-acrylate, mono- or bis-diene, etc.). However, the present invention further encompasses a mixtures of polymerizable and nonpolymerizable phospholipids to generate non-polymerized domains in association with thrombomodulin, truncated thrombomodulin or other antithrombotic protein.

The present invention further provides stable antithrombogenic membrane mimetic surface assemblies in which thrombomodulin, a truncated thrombomodulin and/or an endothelial protein C receptor has been incorporated into a lipid assembly. Thrombomodulin, truncated thrombomodulin or endothelial protein C receptor can be from native or recombinant sources, and coding sequences for same are known to the art.

The present invention provides methods for generation of a stable alkylated surface assembly on the surface of a porous conduit or other material by impregnation of the conduit with a hydrated substrate, sequential complexation of polyelectrolytes to the charged hydrated substrate present on the lumenal side of the conduit and surface coating of the charged hydrated substrate with an oppositely charged amphiphilic polymer containing long chain alkanes (C14 to C24, desirably C16 to C22). Preferred conduits of the present invention include porous expanded PTFE (ePTFE) or Dacron prosthesis impregnated with gelatin or alginate, followed by sequential coating with alginate and poly-L-lysine. However, the conduit can be made of any synthetic polymer (PTFE, PET, PEU) or appropriately processed native biomacromolecules (such as collagen or polysaccharides) or recombinant polymers (e.g., elastin or collagen or protein mimetic polypeptide polymers). Likewise, the hydrated substrate can be any synthetic polymer (e.g., glycopolymers or hydrogels), at least one native biomacromolecule (e.g., collagen, gelatin, alginate or other polysaccharides or proteins and/or cross-linked derivatives thereof) or recombinant proteins or protein-mimetics) chosen to facilitate complexation with positively and negatively charged polyelectrolytes, including but not limited to alginate or poly-L-lysine. Other pairs of oppositely charged polymers are known to the art, and with the proviso that a pair is compatible with the intended medical use, it can be substituted in the practice of this invention. Cross-linkable pairs of charged polyelectrolytes can also be used in the practice of the present invention. It is desired that the last polyelectrolyte applied to the surface carries a positive charge to facilitate ionic complexing with the negatively charged phospholipid to be subsequently applied to the surface. The hydrated substrate can also contain other biologically active compounds, including therapeutic agents.

A preferred embodiment of the alkylated surface is a charged amphiphilic oligomer or polymer with long chain alkanes that complexes onto oppositely charged polyelectrolytes when coated onto the surface of the impregnated conduit. Alternative means of forming an alkylated surface can also include ionic complexation of charged lipid conjugates onto the surface or direct surface grafting of lipid conjugates. Next there is added a polymerizable functionalized phospholipid and liposomes comprising at least one antithrombogenic protein, desirably a thrombomodulin or a truncated thrombomodulin.

The method of the present invention for producing a stable antithrombotic membrane mimetic surface on a synthetic prosthesis, synthetic vascular graft, medical implant, medical device or heterograft tissue comprises the steps of:

(a) providing a hydrated surface on at least one surface of a synthetic prosthesis, synthetic vascular graft, medical implant, heterograft tissue or medical device;

(b) complexing at least one polyelectrolyte to the hydrated surface of step (a) to produce a polyelectrolyte-complexed surface;

(c) coating the polyelectrolyte-complexed surface of step (b) with an amphiphilic polymer, wherein said amphiphilic polymer comprises alkyl groups of from about 8 to about 20 carbon atoms to produce an alkylated hydrated surface;

(d) providing at least one polymerizable functionalized phospholipid to the alkylated surface of step (c) and further fusing antithrombotic liposomes to the alkylated hydrated surface of step (c) to produce a stabilization surface;

(e) photopolymerizing the at least one polymerizable functionalized phospholipid in the stabilization surface of step (d) to produce a stable, antithrombotic membrane mimetic surface on the synthetic prosthesis, synthetic vascular graft, medical implant, medical device or heterograft tissue, whereby the synthetic prosthesis, synthetic vascular graft, medical implant or medical device is improved in biocompatibility over a synthetic prosthesis, synthetic vascular graft, medical implant or medical device lacking said stable, antithrombotic membrane mimetic surface.

The present invention further provides blood contacting materials, prostheses and other implantable materials and devices, surface coated according to the methods of the present invention, can include, without limitation, vascular grafts, shunts, stents, small diameter (about 4 to about 6 mm inner diameter), dialysis tubing, membranes and hollow fiber systems, membrane oxygenators, artificial heart valves and left ventricular assist devices and medical diagnostic devices as well as biological material for implantation into a patient, for example, heterograft tissues including but not limited to porcine heart valves and bovine carotid vascular grafts, made by the methods of the present invention.

The blood contacting materials, prostheses and other implantable materials and devices, surface coated according to the methods of the esent invention, can include, without limitation, vascular grafts, shunts, stents, small diameter (about 4 to about 6 mm inner diameter), dialysis tubing, membranes and hollow fiber systems, membrane oxygenators, artificial heart valves and left ventricular assist devices and medical diagnostic devices as well as biological material for implantation into a patient, for example, heterograft tissues including but not limited to porcine heart valves and bovine carotid vascular grafts. Surface coating of a blood contacting organ such as an artificial heart, lung, kidney or liver is within the scope of the present invention.

DETAILED DESCRIPTION OF THE INVENTION

Figure 1:
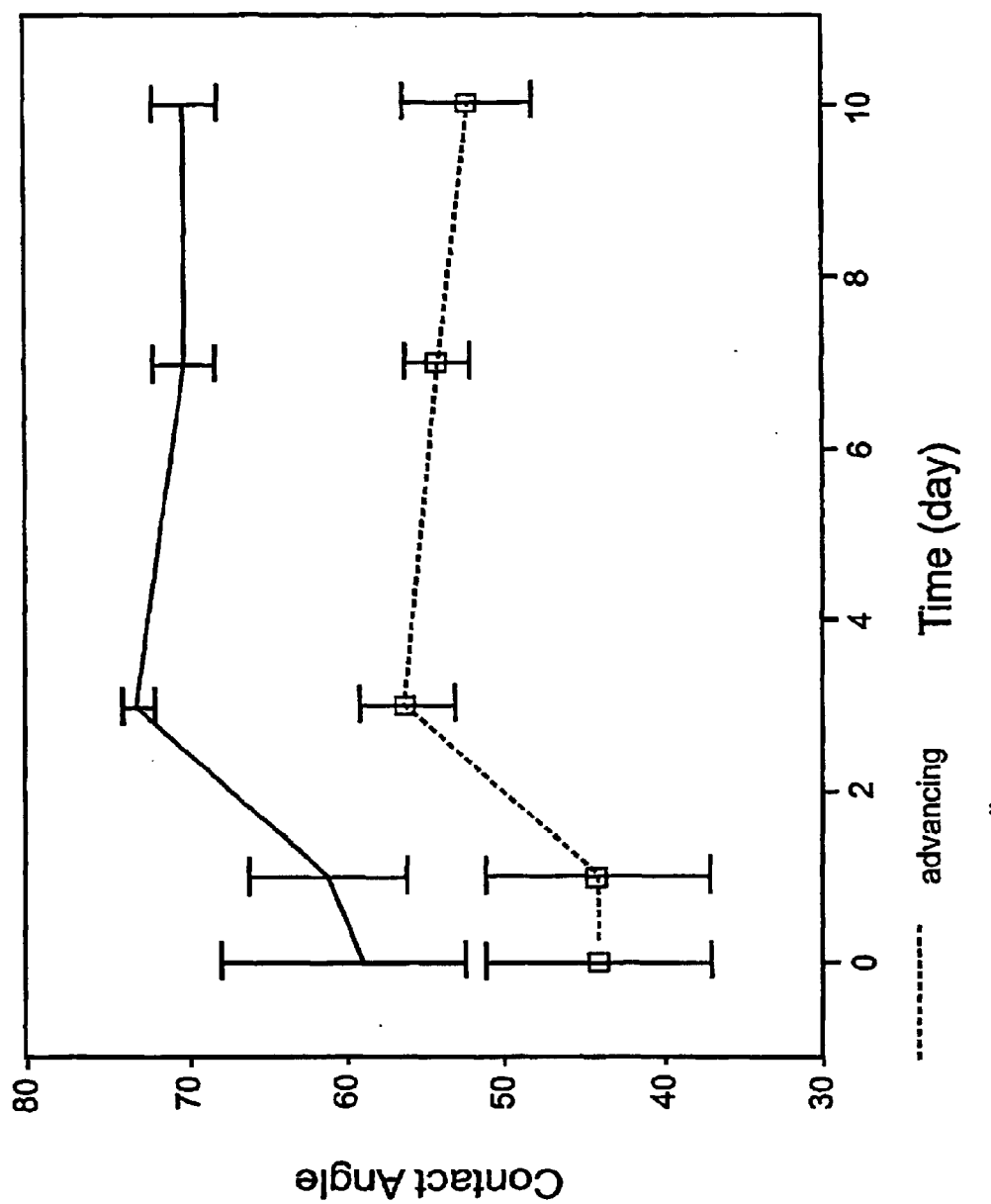
FIG. 1 tracks the serial contact angles of TM-containing photopolymerized planar membrane mimetic assemblies over 10 days of storage in water.

Abbreviations used in the present disclosure include the following: mono-AcrylPC, AcPC, acrylate functionalized phosphatidylcholine; mono-AcrylPE, acrylate functionalized phosphatidylethanolamine; DCC, dicyclohexylcarbodiimide; DDG, 2,3-dichloro-5,6-dicyano-1,4-benzoquinone; DMAP, N,N-dimethylaminopyridine; EY, eosin Y; FITC, fluorescein isothiocyanate; NHS-Biotin, N-hydroxysuccinimidobiotin; EMC, -ε-maleimidocaproyl; EMCS, -ε-maleimidocaproyl succinimide; PMB, p-methoxybenzyl; Troc-amide, 2,2,2-trichloroethoxyamide; PEU, poly(ether urethaneurea); PFTE, polytetrafluoroethylene; ePFTE, expanded polytetrafluoroethylene; PLL, poly-L-lysine; HEA, 2-hydroxyethyl acrylate; AOD, 3-acryloyl-e-3-(N,N-dioctadecylcarbamoyl propionate); AAPD, 2,2'-azobis(2-methylpropionamidine) dihydrochloride; AIBN, 2,2'-azobisisobutyronitrile; SS, styryl sulfonate.

Model thin films that mimic cell and tissue surfaces have attracted considerable attention due to their potential as tools to probe cell and molecular interactions and as bioactive coatings for sensor or medical implant applications (Fuhrhop, J.-H. and Koning, J. (1994) *Membranes and Molecular Assemblies: The Synkinetic Approach*, The Royal Society of Chemistry; Sackmann, E. and Tanaka, M. (2000) *Trans Biotechnol.* 18, 58–64). Specifically, the fabrication of supported lipid membranes provides a practical method for the immobilization of transmembrane proteins, including those that serve as receptors, channels, or pores, as well as the incorporation of native or synthetic lipopeptides or glycoplipids. In most studies, phospholipids differing in chemical composition, saturation and size have been utilized as the primary building blocks of film structures (Lamparski et al. (1992) *Biochemistry* 31:685–694; Plant, A. L. (1993) *Langmuir* 9: 2764–2767; Plant et al. (1995) *Anal. Biochem.* 226,342–348; O'Brien et al. (1998) *Acc. Chem. Res.* 31, 861–868). We have previously reported a method to prepare stable, substrate-supported phospholipid films via in situ photopolymerization of an acrylate functionalized phosphatidylcholine (mono-AcrylPC, 1) assembly (Marra et al. (1997) *Macromolecules* 30, 6483–6488; Marra et al. (1997) *Langmuir* 13, 5697–5701; Orban et al. (2000) *Macromolecules* 33, 4205–4212). See also U.S. Pat. Nos. 6,171,614 and 5,071,532 and International Published Application WO 00/000,239. Herein, we describe the design of a novel polymerizable lipid, acrylate functionalized phosphatidylethanolamine (mono-AcrylPE, 2), in which the amino function can serve as a handle for further modifications. As shown in Scheme 2, terminal groups, such as biotinyl and N-(ε-maleimidocaproyl) (EMC) were introduced by acylation of the amine group of phosphatidylethanolamine. These linkers facilitate the incorporation of proteins or other target molecules via specific high affinity (biotin) interaction (Plant et al. (1989) *Anal. Biochem.* 176, 420426; Kim et al. (2000) *Langmuir* 16, 2808–2817; Hergenrother et al. (2000) *J. Am. Chem. Soc.* 122, 7849–7850; Wilbur et al. (2000) *Bioconjugate Chem.* 11, 569–583) or by covalent (EMC) attachment (Viitala et al. (2000) *Langmuir* 16, 4953–4961; Elliott, J. T. and Prestwich, G. D. (2000) *Bioconjugate Chem.* 11, 832–841). An example is also provided, in the case of generating a polymerizable lipid conjugate containing a fluorescent dye (FITC), which provides a mechanism for direct detection of the lipid membrane (Kim et al. (2000) supra; Roy et al. (2000) *J. Org. Chem.* 65, 3644–3651; Einaga et al. (1999) *J. Am. Chem. Soc.* 121, 3745–3750; Daugherty, D. L. and Gellman, S. H. (1999) *J. Am. Chem. Soc.* 121, 4325–4333). A polymerized thin film composed of both AcrylPC and AcrylPE is associated with an increase in protein binding efficiency due to its inherently greater stability over that of lipid assemblies that are stabilized solely by non-covalent interactions (Marra et al. (1997) *Macromolecules* 30, 6483–6488; Ringsdorf et al. (1988) *Angew. Chem. Int. Ed. Engl.* 27, 113–158; Chapman, D. (1993) *Langmuir* 9, 39–45). Herein, we report the synthesis, characterization, and terminal functionalization of mono-AcrylPE (2).

Unlike mixed diacyl phosphatidylcholine, mixed diacyl phosphatidylethanolamine could not be prepared directly from commercially available lyso-phospholipid because protection and deprotection of the ethanolamine requires additional steps (Marra et al. (1997) *Macromolecules* 30, 6483–6488; Martin et al. (1994) *J. Org. Chem.* 59, 4805–4820). Therefore, in the present approach sequential acylation of the primary and secondary hydroxy groups of a 3-protected sn-glycerol was performed and followed by deprotection and phosphorylation with an N-protected phosphorylating agent. Subsequent global deprotection yielded the expected phospholipid. The selective acylation of the primary hydroxy group in 3 (Hebert et al. (1992) *J. Org. Chem.* 57, 1777–1783) was performed with palmitic acid in the presence of coupling reagent dicyclohexylcarbodiimide (DCC) and N,N-dimethylaminopyridine (DMAP) to give monoester 4 and trace diester. Sequential acylation of 4 with 12-acryloxy-1-dodecanoic acid (O'Brien et al. (1998) *Acc. Chem. Res.* 31, 861–868) provided a protected 1,2-diacyl-sn-glycerol (5). The p-methoxybenzyl (PMB) group was removed by treating it with 2,3-dichloro-5,6-dicyano-1,4-benzoquinone (DDG) to give 1,2-diacyl-sn-glycerol (6) in good yield. The phosphorylation of 6 with 2,2,2-trichloroethoxyamide (Troc-amide) (24) afforded Troc-PE (Marra et al. (1997) supra) which was used for the next reaction without purification. The Troc-protecting group was removed by treating crude 7 with zinc in acetic acid to yield the desired polymerizable mono-AcrylPE (2) as a white solid in 62% yield (Scheme 1). These compounds were characterized by NMR spectra. For example, the distinctive multiplet peaks at 5.10–5.00 ppm are characteristic of the proton at the C-2 position on the glycerol backbone of 1,2-diacyl glycerol (5) (Ponpipom, M. M. and Bugianesi, R. L. (1980) *Lipid Res.* 21, 336–339), and the vinyl group of acrylate was confirmed at 6.38 (dd, 1H), 6.11(dd, 1H) 5.80 (dd, 1H) ppm as an AMX spin system. Three additional methylene groups in compound 7 were assigned at 4.73 (2H), 3.96 (2H) and 3.47 (2H) ppm as multiplet peaks. For compound 2, the $NH_3^+$ group was noted as a broad peak at 8.51 ppm (3H) (26), and the vinyl group of acrylate was confirmed at 6.39 (dd, 1H), 6.14(dd, 1H), 5.81 (dd, 1H) ppm as an AMX spin system.

Treatment of mono-AcrylPE (2) with commercially available fluorescein isothiocyanate (FITC), N-hydroxysuccinimidobiotin (NHS-Biotin), and N-(e-maleimidocaproyl) succinimide (EMCS) in the presence of triethylamine provided the desired conjugated lipid-AcrylPE-FITC (8), AcrylPE-Biotin (9), AcrylPE-EMC (10)—all in good yield (Scheme 2). $^1$H NMR spectra confirmed the predicted structures of the lipid conjugates. Excluding lipid backbone protons, nine aromatic protons were observed at 8.26 (m, 1H), 7.40–7.30 (m, 1H), 7.16–7.04 (m, 3H) and 6.68–6.59 (m, 4H) ppm for AcrylPE-FITC (8); two amido protons were noted at 7.79 (br, 1H) and 7.00 (br, 1H) ppm for AcrylPE-Biotin (9), and two olefin protons were observed at 6.67 (s, 2H) ppm for AcrylPE-EMC (10).

Preliminary fabrication of mixed lipid films containing AcrylPE-FITC (8) and mono-AcrylPC (1) (Marra et al. (1997) supra) was performed on the alkylated surface of alginate beads as models supports. Briefly, the beads (d=300 nm) were incubated with a lipid vesicle solution composed of 8 and 1, followed by photopolymerization using EY/triethanolamine as co-initiator. The resultant beads were examined by confocal microscopy. The successful formation of the lipid film was confirmed by the presence of fluorescent activity on the surface of the beads while no such activity was observed in the interior of the beads.

Thus, we have successfully developed a synthetic approach for generating bifunctional phospholipid conjugates containing both an acrylate functionality and a terminal linker, such as biotin or the N-(e-maleimidocaproyl) function group. These conjugates will enhance the capacity to generate stable, self-assembled, biologically functional and chemically heterogeneous, membrane-mimetic films for use in medical implants, prostheses and medical diagnostic devices and materials. The presence of at least one of a phosphatidylethanolamine and a phosphatidylcholine group on the artificial surface significantly improves the biological activity of thrombomodulin or a truncated thrombomodulin derivative in terms of minimizing thrombogenesis via activation of the endogenous protein C activation anticoagulant pathway, and similarly, improves biocompatibility for the implanted medical materials.

The present inventors have developed biologically active, membrane-mimetic, substrate-supported surface assemblies that are sufficiently robust for medical implants and prostheses. The incorporation of thrombomodulin or truncated thrombomodulin into the membrane-mimetic assemblies described herein has resulted in thromboresistance (at least short term), and in addition, such coated surfaces have not exhibited significant levels of platelet adhesion in the acute baboon ex vivo shunt model. Thus, the antithrombotic-containing surface assemblies of the present invention are improved in biocompatibility over those previously reported.

Despite the partial loss of an endothelial lining, intimal repair processes often occur in the absence of overt vessel thrombosis due to physiological responses which efficiently modulate the coagulation cascade and platelet activation. The release of nitric oxide and prostacyclin by the vessel wall limits platelet activation and aggregation. However, the inhibition of blood coagulation is primarily achieved by two alternate mechanisms: serine proteinase inhibitors, also known as 'serpins,' which act by the formation of stable 1:1 molar complexes with their target enzymes and the protein C pathway that leads to inactivation of coagulation factors Va and VIIIa. Antithrombin III (ATIII) and tissue factor pathway inhibitor are both examples of serpins that inhibit thrombus formation. Serpin mediated anticoagulation processes are largely confined to the surface of endothelial and smooth muscle cells due to their ability to bind to sulfated glycosaminoglycans, particularly heparan sulfate. Moreover, heparan sulfates on the smooth muscle cell surface, in the ECM or on neighboring uninjured endothelium, actively accelerate these proteinase inhibition reactions. To date, the catalysis of the ATIII-thrombin reaction by heparan sulfate has been the most thoroughly characterized. However, despite the presence of serpin binding sites on heparan sulfates and the well characterized anticoagulant properties of these glycosaminoglycans, the physiological significance of the anticoagulant/antithrombotic functions attributed to heparan sulfates at the vascular cell surface has not been conclusively established. For example, high affinity ATIII binding sites have not been localized to heparan sulfates that are in direct contact with blood. Moreover, the catalytic effect of heparan sulfate on the ATIII-thrombin reaction in recirculating rabbit Langendorff heart preparations has not been confirmed. There is, however, growing evidence that thrombomodulin (TM), as a critical regular of the endogenous protein C pathway, represents the major anticoagulant mechanism that is operative in both normal and injured blood vessels under physiologic conditions in vivo (Bourin, M. C. and U. Lindahl [1993] *Biochemical J*. 289[Pt2]:313–330; Kalafatis et al. [1997] *Crit. Rev. Eukaryotic Gene Expression* 7(3): 241–280).

Thrombomodulin is a 60 kD type I transmembrane protein that provides high affinity binding sites for thrombin at the lumenal surface of the vascular endothelium and on smooth muscle cells (Owen et al. [1981] *J. Biol. Chem.* 256[11]:5532–5535; Esmon et al. [1981] *Proc. Natl. Acad. Sci. USA* 78[4]:2249–2252; Esmon et al. [1982] *J. Biol. Chem.* 257[2]:859–864; Esmon et al. [1999] *Haematologica* 84[4]:363–368; and Esmon et al. [1997] *Thromb. Haemostasis* 78[1]:70–74). While it is constitutively present on the cell surface, its expression is also upregulated after exposure to thrombin, basic fibroblast growth factor (bFGF), and platelet-derived growth factor (PDGF). TM forms a 1:1 molar complex with thrombin, and in the process, switches off all known procoagulant/proinflammatory functions of thrombin, and instead channels the catalytic power of the enzyme into complex anticoagulant/anti-inflammatory activities. TM alters the biological function of thrombin in three distinct substrate dependent anticoagulant pathways. While free thrombin efficiently converts fibrinogen to fibrin, thrombin bound to TM is no longer capable of cleaving fibrinogen, nor is it able to activate factor V or platelets (Esmon et al. [1983] *J. Biol. Chem.* 258(20):12238–12242). TM also enhances the rate of thrombin inactivation by ATIII (~8-fold) and dramatically accelerates (~20,000-fold) the ability of thrombin to activate protein C, a vitamin K dependent serine protease. Inactivated thrombin and activated protein C (APC) are released from TM, which is then capable of accommodating additional macromolecular substrates. The transfer of fluid phase reactants, such as protein C, thrombin, and ATIII, to a catalytic surface and the removal rate of formed products depends upon the kinetics of molecular adsorption and desorption processes ($k_{on}/k_{off}$), intrinsic surface reaction rate constants, convection by fluid flow and diffusion within the boundary layer region. Thus, in the presence of competing substrates for a given cofactor and enzyme active site, local flow conditions are likely to have a significant effect on whether thrombin behaves as a pro-or anticoagulant. Surprisingly little information is available regarding the extent to which flow influences the efficiency of TM in vitro or in vivo.

Activated protein C, together with its cofactor protein S, inactivates two coagulation factors, Va and VIIIa, to prevent the generation of Xa and thrombin, which are critical for the amplification of the coagulation cascade. Sakata et al. (1985) *Proc. Natl. Acad. Sci. USA* 82(4):1121–1125, have suggested that activated protein C also promotes fibrinolysis. Once generated, APC is one of the slowest of the serine proteases to be inactivated and cleared from the circulation. Somewhat paradoxically, TM promotes the inactivation of thrombin by ATIII and this, in turn, limits protein C activation. Conceivably, APC generation proceeds only as long as excess thrombin is generated. Thus, the antithrombin-dependent anticoagulant mechanism of TM ensures that protein C activation is terminated once excess thrombin formation ceases. Without wishing to be bound by any particular theory, it is believed that local hemodynamic conditions in the arterial and venous circulation are important regulators of APC's capacity to locally inactivate factors Va and VIIIa. It is well established that patients with protein C or protein S deficiency, as well as those with resistance to APC, are prone to develop thromoembolic events. Likewise, mutations in the TM gene may be a risk factor for both venous and arterial thrombosis, including myocardial infarction.

Membranes, as self-organizing noncovalent aggregates, offer a model for molecular engineering in which the constituent members can be controlled, modified, precisely defined, and easily assembled. During the past decade, phospholipids differing in chemical composition, saturation, and size have been utilized as building blocks in the design of a variety of structures of complex geometry. Lipid-based cylinders, cubes, and spheres have found applications in both drug delivery and as templates for composite molecularly engineered structures. Surface-coupled bilayers for biosensor applications have also been produced by assembling a layer of closely packed hydrocarbon chains onto an underlying substrate followed by exposure to either a dilute solution of emulsified lipids or unilamellar lipid vesicles (Spinke et al. [1992] *Biophys. J*. 63:1667–1671; Seifert et al. [1993] *Biophys. J*. 64:384–393; and Florin et al. [1993] *Biophys J*. 64:375–383). In addition, Langmuir-Blodgett techniques have been used as an alternate strategy to construct supported bilayers via a process of controlled dipping of a substrate through an organic amphiphilic monolayer (Ulman, A. [1991] *An Introduction to Ultrathin Organic Films from Langmuir-Blodgett to Self-assembly*, New York, Academic Press). Remarkably, these noncovalent molecular assemblies exhibit a high degree of stability. A force of 26 kT is required to remove a double chained C-16 phosphatidylcholine molecule from a bilayer into water (Cecv G. and Marsh D. [1987] *Phospholipid Bilayers*, N.Y., Wiley; and Helm et al. [1991] *Proc. Natl. Acad. Sci. USA* 88:8169–8173). This nearly approximates the biotin-streptavidin bond energy of 35 kT and is several orders of magnitude greater than the strength of typical monoclonal antibody-antigen interactions. Thus, the significance of the methodologies of the present invention lies in the ability to engineer relatively robust materials with an unparalleled level of reproducibility and molecular control over surface order and chemistry.

Membrane-mimetic systems have also had a direct impact on efforts aimed at understanding the mechanisms of blood coagulation at sites of vascular wall injury and on artificial surfaces. In a series of investigations using planar membrane models, Thompson and colleagues (Pearce et al. [1993] *J. Biol. Chem*. 268:22984–22991; and Tendian et al. [1991] *Biochemistry* 30:10991–10999) have characterized the molecular requirements for prothombin binding to phospholipid membranes. It has been observed that the phosphoiylcholine head group appears to limit the induction of blood clot formation on synthetic surfaces (Ishihara et al. [1994] *J. Biomed. Mater. Res*. 28:225–232; Hayward et al. [1984] *Biomaterials* 5:135–142; and Hall et al. [1989] *Biomaterials* 10[4]:219–224). It has been proposed that this biological property is related to the large amount of water bound to this zwitterionic head group, or conceivably, the selective adsorption to phosphorycholine of specific plasma protein(s) that inhibit the blood clotting process (Chapman, D. [1993] *Langmuir* 9:39–45). While we have also observed limited thrombus formation and neointimal hyperplasia on phospholipid functionalized surfaces using short term in vivo assays (Marra et al. [1997] *Macromolecules* 30:6483–6487; and Chen et al [1997] *Ann. Vasc. Surg*. 11[1]:74–79), the inherent strength of a membrane-mimetic based approach is the capacity to incorporate within these systems a variety of biologically active components which control blood coagulation and endothelial regeneration. Supramolecular membrane complexes provide useful systems for probing and controlling processes at both blood- and tissue-material interfaces.

Several investigators have described the direct immobilization of thrombomodulin onto polymeric surfaces in order to generate thromboresistant materials for blood contacting applications. Kishida et al. (1994) *Biomaterials* 15(10): 848–852; Kishida et al. (1994) *Biomaterials* 15(14): 1170–1174; and Kishida et al. (1994) *ASAIO Journal* 40(3): M840–845 have conjugated TM to both aminated and carboxylated surfaces, including poly(vinyl amine) and poly (acrylic acid) surface-grafted polyethylene and a surface-hydrolyzed poly(ether urethaneurea). Vasilets et al. (1997) *Biomaterials* 18(17):1139–1145, have reported the immobilization of TM onto poly(acrylic acid) surface-grafted PTFE. In all cases, the conjugation scheme utilized a carbodiimide based coupling reaction to link TM to the substrate via freely available amino or carboxyl functionalities on the protein surface. In vitro studies demonstrated that both clotting time and protein C activation were enhanced, and this activity appeared to be directly proportional to TM surface density, as determined by a ninhydrin assay. However, the ability to control TM surface concentration was substrate dependent, with reported TM densities ranging between 0.15 and 0.45 $\mu g/cm^2$, and TM bioactivity was significantly reduced after surface coupling, as evident by protein C activation rates which were increased only 5 to 10-fold as compared with an observed 20,000-fold enhancement when TM is evaluated as a component of either lipid vesicles or the endothelial cell surface. The loss of cofactor activity is believed attributable to the protein immobilization procedure, which is driven by random-site reactions to any accessible functional group on the TM surface, including those within the thrombin binding site. The impact of local flow conditions on the effectiveness of this strategy was not reported.

Although these studies confirm that substrate bound TM has the potential to limit thrombus formation on synthetic surfaces that are otherwise thrombogenic, the observed reduction in TM bioactivity emphasizes that thrombomodulin's biological properties are intimately tied to a variety of structural features which can be lost upon direct covalent coupling to a biomaterial surface. For example, TM's ability accelerate the thrombin-dependent activation of protein C requires three tandemly repeated EGF-like domains that serve as a thrombin binding site; a serine/threonine-rich 65 A spacer between the EFT-like domains and the transmembrane domain which optimally align thrombin's active site with the critical scissile bond in protein C; and a covalently associated chondroitin sulfate moiety that increases the affinity of thrombin binding to TM by 10- to 20-fold and catalyzes ATIII inactivation of thrombin (Sadler, J. E. [1997] *Thromb. Haemostasis* 78[1]:392–395; and Esmon, C. T. [1995] *FASEB Journal* 9[10]:946–955). While some activity is retained even after the solubilization of TM with detergents, membrane association significantly accelerates protein C activation by TM. This is mediated, in part, by the ability of the membrane to locally concentrate and coordinate the approximate alignment of reacting cofactors and substrates with TM (Galvin et al. [1987] *J. Biol. Chem.* 262[5]:2199–2205). For example, protein C has a C-terminal 4-carboxyglutamic acid (Gla) domain which binds to the cell membrane and presumably increases its local concentration by confining it to the two-dimensional plane of the lipid bilayer (Esmon et al. [1983] *J. Biol. Chem.* 258:[9]:5548–5553; Mann et al. [1988] *Ann. Rev. Biochemistry* 57:915–956; Kalafatis et al. [1996] *Critical Reviews in Eukaryotic Gene Expression* 6[1]:87–101). In addition, the binding of protein C to the plasma membrane may also induce conformational changes that help align the protein C cleavage site with thrombin's proteolytically active domain. Both electrostatic and hydrophobic interactions may be involved in the association of protein C with the cell membrane. In this regard, recent studies suggest that protein C prefers to bind to and function on membranes that contain both phosphatidylcholine and phosphatidylethanolamine lipids. Protein C may also directly interact with fatty acid side chains within the membrane bilayer (Smirnov et al. [1999] *Biochemistry* 38[12]:3591–3598). It is surprising that the nature of the phospholipid headgroup may contribute to the subsequent catalytic and binding efficiency of activated protein C. For example, Smirnov et al. (1999 supra); and Smirnov et al. (1994) *J. Biol. Chem.* 269(2):816–819, have demonstrated that both the PE headgroup and phospholipid polyunsaturation contribute to factor Va inactivation by the activated protein C complex. Thus, the lipid bilayer serves as an essential 'cofactor,' that in concert with TM, accelerates protein C activation and subsequently optimizes APC anticoagulant activity. The present inventors have developed TM and tTM-containing membrane mimetics which, when coated onto vascular prostheses, implants and other blood contacting material, provide actively antithrombogenic materials.

Biocompatibility (or biological compatibility) refers to the interactions of living body tissues, compounds and fluids, including blood, etc., with any implanted or contacting polymeric material (biomaterial). Of particular interest are those materials which are in contact with blood, especially with flowing blood. Biocompatible biomaterials are of great importance in any biomedical application including, for example, in the implantation of vascular grafts and medical devices such as artificial organs, artificial heart valves, artificial joints, catheters and various other prosthetic devices into or on the body as well as those which contact blood ex vivo.

The present invention provides a biomaterial comprising as part of a membrane mimetic surface a phospholipid or phospholipid derivative with a polymerizable monomeric group (e.g., acryloyloxy, methacryloyl, dienoyl, sorbyl, styryl, acrylamide, acrylonitrile, N-vinyl pyrrolidone, etc.). Such biomaterial phospholipid molecules form self-assembled monolayers that attach or absorb (e.g., through hydrophobic interactions, etc.) to a substrate whereon the polymerizable monomeric groups of the biomaterial phospholipid moieties are photopolymerized in situ. The biomaterial of the invention comprises at least two levels of attachment or cross reaction, i.e., within the plane of phospholipid molecules, e.g., linking together of different phospholipid alkyl chains, and between planes, e.g., interdigitating chains between phospholipid monolayers and the substrate surface. The vesicle fusion and photopolymerization conditions provided herein are less harsh than polymerization conditions previously used, thus mediating less inactivation of biologically active molecules, e.g. TM.

Biomaterials taught in the art are often covalently linked to a substrate. In the instant invention, a biomaterial is provided that is non-covalently affixed to a substrate, permitting a detachment of the polymerized biomaterial from the substrate or a replacement of one type of polymerized biomaterial by another type of biomaterial of the invention. The instant invention also contemplates biomaterials that are covalently attached to a substrate to fulfill a specific purpose or to meet a specific environmental condition. The biomaterials of the invention serve as specific modular surface design units. This concept of biomaterials composed of modular design units offers increased variability, versatility and flexibility not only with respect to choice of functional groups on a molecular or microscopic level (e.g., in the phospholipid functional groups such as phosphorylalkylamino groups, etc.) but also in the assembly of units into a layer on a macroscopic surface structure.

The present invention provides for biocompatible implanted and blood contacting surfaces that include, but are not limited to, in situ polymerized phospholipids on solid alkylated surfaces of a self-assembled monolayer, e.g., octadecyltrichlorosilane (OTS) on glass; in situ polymerized phospholipids on a polymer supported monolayer of molecularly mobile alkyl chain, e.g, an amphiphilic, dialkyl-containing terpolymer bound to a gold-coated silicon wafer; and in situ polymerized phospholipids onto hydrated surfaces further complexed with polyelectrolytes, amphiphilic molecules, polymerized phospholipids and an antithrombotic protein. The antithrombotic protein can be TM, a truncated TM or an endogenous protein C activator.

The biocompatible surfaces of the present invention comprise at least one biocompatible biomaterial surface modular unit comprising a phospholipid moiety comprising a polymerizable monomeric group, e.g., an acryloyloxy group, methacryloyl, dienoyl, sorbyl, styryl, acrylamide, acrylonitrile, N-vinyl pyrrolidone, etc., which unit is attached or adsorbed or affixed to an alkylated substrate, and polymerized thereon in situ, in an amount and orientation effective to provide an improved nonthrombogenic surface relative to a substrate without the polymerizable monomeric group-containing phospholipid moiety attached thereto. The phospholipid moiety contains an alkyl amino group, e.g., a choline, ethanolamine or the like, and a phosphate polar group. In one embodiment the biocompatible biomaterial has the structure (I):

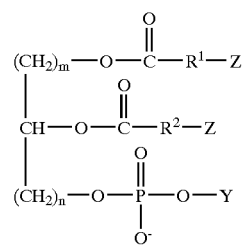

wherein $R^1$ is a ($C_{14}$–$C_{30}$) alkyl group;
$R^2$ is a ($C_{14}$–$C_{30}$) alkyl group;
m is 1–4;
n is 1–4;

Y is 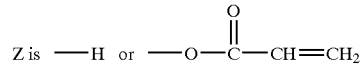

Z is 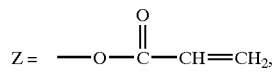

such that if $R^1$ is attached to Z=—H, then $R^2$ is attached to $$Z = -O-\overset{O}{\underset{\|}{C}}-CH=CH_2,$$

or vice versa.

The biocompatible biomaterial can comprise the structure (I) wherein $R^1$ is a ($C_{12}$–$C_{30}$) alkyl group; $R^2$ is a ($C_{10}$–$C_{20}$) alkyl group; m is 1 and n is 1. In a preferred exemplification, the biocompatible material is 1-palmitoyl-2[12-(acryloyloxy)dodecanoyl]-sn-glycero-3-phosphorylcholine. The acrylate groups of the lipid molecules polymerize, forming a surface network in a two-dimensional plane; desirably the polymerization is carried out at from about 25 to about 42 C, desirably 40 C where EY/triethanolamine initiate polymerization to prevent thermal decomposition of biomolecules present on the blood contacting surface of the prosthetic or other material of the present invention.

The substrate (or blood contacting surface) which is coated for improved biostability and biocompatibility, can include, but is not limited to, an insoluble synthetic or natural, inorganic or organic material such as glass, silicon wafer, hydrogel (e.g., alginate, gelatin, collagen, polyhema, hydroxyethylmethacrylate, polyacrylamide, derivatives thereof, and the like), Dacron, ePTFE, PTFE, PEU, etc. The material of which the substrate is formed can be porous or solid. Specific examples can include h allylated substrates such as octadecyltrichlorosilane (OTS) coated glass, a self-assembling monolayer of an acylated octadecylmercaptan (e.g., ODT) on gold, octadecyl chains of an amphiphilic copolymer cast onto an alginate substrate, etc. A preferred substrate of the invention is exemplified by an amphiphilic dialkyl containing terpolymer bound to gold coated silicon wafers. Thus, a preferred biomaterial of the invention comprises an acryloyloxy-containing phospholipid which is adsorbed to an amphiphilic polymer surface (a molecularly mobile alkylated surface extending from a polymer bonded to a substrate) and which is polymerized thereon.

The biocompatible biomaterial of the present invention exhibits enhanced stability. In a particular example of this embodiment, a stabilized, phosphatidylcholine-containing polymeric surface was produced by in situ polymerization of 1-palmitoyl-2-[12-(acryloyloxy)dodecanoyl-sn-glycero-3-phosphorylcholine at a solid-liquid surface. The polymerizable phospholipid monomer was synthesized, prepared as unilamellar vesicles, and fused onto close-packed octadecyl chains as part of an amphiphilic terpolymer. Photopolymerization was carried out as described herein. Contact angle measurements demonstrated that the polymerized lipid monolayer when supported by the amphiphilic terpolymer exhibited enhanced stability than when supported on a self-assembled monolayer of octadecyl mercaptan (ODT)-coated surface. The amphipilic molecule is desirably applied to the surface of interest over a hydrated layer (e.g., alginate or gelatin) over which a polyelectrolyte is applied (alginate or PLL, and preferably sequential coatings of both).

The term improved stability as used herein refers to the stability of a membrane mimetic layer at a liquid-solid interface as determined by the absence of significant increases in serial contact angle measurements of surface properties, as is commonly used in the art. An increase in water contact angles over time is correlated with decreased stability.

The term substrate as used herein refers to a surface of any synthetic or natural material that is insoluble in physiological fluids, for example, metal (e.g., titanium, stainless steel, etc.), glass (e.g., soda glass, silica glass), inorganic material or organic material (e.g., hydrogel, polyacrylamide, methacrylate, other polymers such as PFTE, ePFTE, PEA, PEU, etc). The phospholipid units can be attached or adsorbed to substrates or, alternatively, that substrates can be coated or modified appropriately (e.g., addition of polymerizable groups, e.g., acrylate groups, to the terminal end of surface alkyl chains) for covalent attachment of the phospholipid unit to the substrate and/or for improved performance in vivo or in contact with blood.

The term phosphatidylcholine as used herein refers to a molecule having the structure:

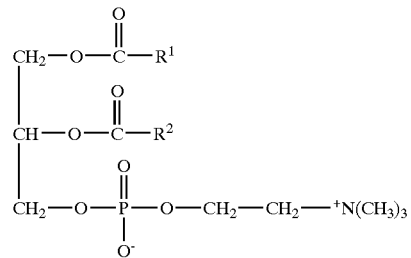

wherein $R^1$ and $R^2$ are usually long chain fatty acyl groups.

The term effective amount and orientation as used herein refers to the amount of phospholipid per substrate as well as the orientation of the phospholipid with respect to the substrate or coating layers thereon required to produce a biomaterial that exhibits improved biocompatibility.

Antithrombotic proteins, as used herein, include thrombomodulin, truncated thrombomodulin and endogenous protein C activator protein. Thrombomodulin refers to a native or recombinant protein which has the full length amino acid sequence of a native thrombomodulin. Desirably, the TM is a native protein and contains the full length amino acid sequence and the covalently bound chondroitin sulfate. Desirably, the ultimate source of a TM (or its coding sequence for recombinant expression) is the same as the organism (human or animal) in which the antithrombotic protein containing device, prosthesis, graft, etc. is to be used. That is, human TM or tTM is to be used in the membrane mimetic surface assemblies where the implant or prosthesis or device is to be in contact with human blood. Truncated thrombomodulin is produced by recombinant means, as described herein, and purified according to the recommendations of the supplier of the expression plasmid, although other expression plasmids and other purification schemes are readily utilized by one of ordinary skill in the art. For example, tTM is expressed with a short poly-histidine tag under the regulatory control of a strongly inducible promoter. The expressed protein is recovered and purified using nickel affinity chromatography. The tTM of the present invention includes at least three epidermal growth factor (EGF) binding domains, a transmembrane domain and a serine-threonine rich spacer of about 65 Å between the EGF domains and the transmembrane domain, and it retains at least about 5–10% of the antithrombotic activity of the native protein, i.e., activation of the endogenous protein C anticoagulation pathway. tTM can bind thrombin, itenhances thrombin inactivation by aTIII and it accelerates protein C activation by thrombin. With respect to the present disclosure the use of the term TM-containing membrane mimetic surface assemblies encompasses surface assemblies containing either full length or truncated thrombomodulin.

In order to stabilize a planar lipid assembly, we had developed a scheme based upon the polymerization of monoacrylate functionalized lipid monomers in the presence of either AIBN or AAPD as free radical initiator. See, e.g., WO 00/000,239, published 6 Jan. 2000. Limitations of this approach include a requirement to carry out this reaction at 70° C. for periods of time exceeding 8 hours; the ability to effectively incorporate proteins or carbohydrate structures into these systems is limited by thermal degradation during the polymerization reaction and the corresponding reduction in biological activity. To functionalize lipid films with thrombomodulin or other elements necessary for an effective membrane-based anticoagulant system, we developed a visible light mediated photopolymerization and liposome fusion scheme that can be carried out at room temperature to minimize thermal denaturation or degradation of the components, including. Briefly, following the fusion of lipid vesicles with an alkylated substrate, eosin Y and triethanolamine are added as free radical initiator and accelerator, respectively. The molecular assembly is polymerized at room temperature following a 30-minute exposure to a quartz halogen lamp. Average advancing/receding contact angles were 58/42° and are comparable to values for materials obtained by the thermally initiated approach. Angle-dependent ESCA measurements were carried out to further define atomic level surface properties, and perpendicular and parallel reflectance-absorbance IR spectra were acquired. These measurements revealed that the molecular orientation of hydrocarbon chains in acrylate-PC films was 46.5° relative to the surface normal. Stability studies and the use of vibrational spectroscopy to characterize lipid packing and orientation are described in Orban at al. (2000) *Macromolecules* 33:3204–4212. The increased film stability over that observed using a thermally initiated process through a mechanism is believed to be related to an increase in molecular chain length, which is achieved when polymerization occurs at a temperature below the transition temperature of the lipid species.

In situ polymerization of phospholipids on an alkylated hydrogel is used to functionalize the lumenal surface of a small diameter vascular graft with a membrane-mimetic thin film. Commercially available vascular grafts, fabricated from expanded PTFE or Dacron fibers, are porous textile structures. Coating these prostheses is facilitated by their initial impregnation with a substrate amenable to subsequent alkylation and lipid film formation. For example, substrates for graft impregnation can include, without limitation, medically compatible materials such as gelatin and/or alginate. In the model study to investigate formation of a stabilized lipid film on a hydrated substrate, an alginate solution was layered onto a glass slide and gelled following the addition of calcium chloride [Chon et al.(1999) *J. Biomater. Sci. Polymer. Ed.* 10:95–108]. A copolymer consisting of the monomers 2-hydroxyethyl acrylate (HEA) and 3-acryloyl-3-oxapropyl-3-(N,N-dioctadecylcarbamoyl)propionate (AOD) in a statistical composition of 1:1 HEA:AOD was synthesized. The alginate was exposed to the copolymer solution, dried, and rehydrated. During water desorption from the gel surface, the hydrophilic HEA component is entangled within the alginate chains, anchoring the copolymer, and allowing the hydrophobic dialkylated monomers to self-assemble at the solid-air interface. Formation of a hydrophobic surface on the rehydrated polysaccharide gel was verified by advancing and receding contact angle measurements of 94±5° and 63±7°, respectively. Unilamellar vesicles consisting of the monacrylate phospholipid monomer were prepared and fused onto the copolymer coated surface. Free radical polymerization was carried out in aqueous solution using AAPD. The supported lipid monolayer displayed advancing and receding water contact angles of 47±8 and 26±7 degrees, respectively. ESCA results confirmed the presence of a lipid film. Contact angle measurements remained unchanged over a several week observation period under static conditions in water, indicating a high level of intrinsic film stability. Comprehensive data analysis can be found elsewhere (Chon et al. 1999 supra).

While coating alginate with an HEA:AOD amphiphilic polymer yielded promising results, several limitations included reliance on an organic solvent, THF, and vacuum drying to mediate alkylation of the hydrogel; therefore, we elected to include styrene sulfonate as a monomer in ths copolymer system. The resulting novel alkylated polyelectrolyte was composed of HEA, AOD, and styrene sulfonate in a molar ratio of 6:3:1. This terpolymer carries negatively charged sulfonate ($SO_3^-$) groups that serve to anchor this polymer to positively charged substrates, such as poly-L-lysine (PLL) [Liu et al. (2000) *Polymer Preprints*]. The capacity to form membrane-mimetic films without the requirement for organic solvents or prolonged vacuum drying was demonstrated using substrates consisting of alginate/PLL multilayers. Briefly, a multilayer of alginate (Kelco, 0.15% w/v in PBS) and PLL (459 kDa; 0.1% w/v in PBS) was generated on glass slides by submerging test surfaces for 30 seconds of contact time in each solution (PLL-alg)$_n$ PLL films were subsequently incubated with a solution of the polyelectrolyte terpolymer in tri(ethylene glycol) (TEG) at a concentration of 1 mM of sulfonate for 4 to 6 h. See Scheme 5. Vesicle fusion and visible light mediated photopolymerization were performed as described above. Surface analyses including contact angle goniometry, ESCA, ellipsometry, and high resolution scanning electron microscopy confirm lipid film formation. Stability of these systems following incubation in PBS for periods exceeding one month has been confirmed. Of note, stable multilayers of alginate and poly-L-lysine can be produced on a variety of hydrated biologically derived substrates, including but not limited to gelatin, which carries a net positive charge at physiologic pH.

To form a membrane-mimetic lipid film on the lumenal surface of an ePTFE vascular graft, the techniques described above have been utilized to coat the lumenal surface of PTFE grafts (4 mm id) with a polymerized monoacryl PC membrane-mimetic thin film. Briefly, PTFE grafts were initially impregnated with an aqueous solution of gelatin (6 wt %), and then the lumenal surface was coated with a series of five alternating layers of alginate (0.15 wt % in PBS) and poly-L-lysine (0.10 wt % in PBS). Coating was performed by serial perfusion of the prosthesis at a flow rate of 1 mL/min for 30 seconds. After each perfusion, the prosthesis was rinsed with deionized water at 1 mL/min. The lumenal surface was then perfused with a 1 mM solution of the HEA:AOD:SS terpolymer in TEGF at a flow rate of 1 mL/h for 1 hour, followed by a 1 hour perfusion of the surface with TEG at 1 mL/h. A 1.2 mM solution of 600 nm monoacrylPC vesicles was prepared in 20 Mm sodium phosphate buffer (pH 7.4) containing 150 mM NaCl and a 10:1 molar ratio of monoacryl PC to Eosin Y. The vesicle solution was perfused through the prosthesis at a flow rate of 1 mL/h for 3 hours and then irradiated for 30 minutes using a quartz halogen lamp. High resolution SEM images were obtained after vacuum drying and coating with chromium. Vesicle fusion and polymerization generates a stable uniform membrane-mimetic coating on the graft surface. At high magnification, fused vesicles are noted on the lumenal surface.

In summary, modification of a gelatin-(alginate/PLL)$_n$ coacervate with a membrane-mimetic thin film has been successfully performed using an amphiphilic polymer with dialkyl side chains, flexible spacer groups, and anionic substituents which anchor the polymer to a cationic surface. After lipid vesicle fusion to the alkylated hyrogel, the lipid assembly is stabilized via in situ photopolymerization. Film structure and morphology have been characterized using a variety of surface sensitive techniques. Film stability for up to four weeks in PBS has been confirmed.

Thrombomodulin has been incorporated into membrane-mimetic lipid assemblies. Rabbit TM was reconstituted into unilamellar phospholipid vesicles varying in mole ratio of POPC to monoacrylPC (AcPC). The incorporation efficiency of TM exceeded 95% as determined by a sucrose gradient. Vesicles were exposed to visible light for varying periods of time in the presence of eosin Y/triethanolamine. Total TM concentration, as determined by measuring Gla-domainless protein C (GD-PC) activity after detergent solubilization of lipid vesicles, is in excellent agreement with those values obtained by use of $^{125}I$ labeled TM [Galvin et al. (1987) *J. Biol. Chem.* 262(5):2199–2205]. Gla-domainless protein C is obtained by the proteolytic cleavage of the γ-carboxyglutamic acid (Gla) containing domain localized to residues 1–41 [Esmon et al. (1983) *J. Biol. Chem.* 258(9):5548–5553]. This domain is responsible for optimal protein C activation by providing an anchor for protein C binding to cell membranes [Kalafatis et al. (1996) Critical Reviews in *Eukaryotic Gene Expression* 6(1) :87–101]. Galvin (1987) supra have demonstrated that Gla-domainless protein C activity can be used to assess the surface concentration of functionally active TM, appropriately oriented such that the catalytic site is positioned above the outer surface of the lipid vesicle. Vesicle concentrations of TM are calculated upon the measurement of the GD-PC activation rate.

All vesicle systems, irrespective of lipid composition (POPC vs AcPC), exhibited similar rates of protein C activation prior to polymerization. Following photopolymerization a modest reduction in the PC activation rate was noted. We believe that this effect may be attributed to two factors. In part, a reduction of TM activity was probably related to direct inactivation of a proportion of TM molecules by free radicals generated during the polymerization process, and we believe that the catalytic efficiency was diminished as a consequence of reduced TM mobility within the membrane complex. The reduction of catalytic activity was greater when TM was incorporated into vesicles composed of increasing concentration of polymerizable lipids.

Kinetic parameters, $k_{cat}$ and Km, were obtained by non-linear regression analysis of observed rates of APC production as a function of protein C concentration (Table 3). As anticipated, free TM has a significantly higher Km value compared to TM incorporated into POPC or non-polymerized AcPC vesicles. However, the Km value for TM in polymerized AcPC is much higher than that observed prior to polymerization, indicating that the mobility of TM in the lipid bilayer influences the formation of the protein C activating complex. The $k_{cat}$ values for all four forms are similar and indicates that the catalytic reaction mechanism remains unchanged. The $k_{cat}$/Km values shows that protein C activation is catalytically efficient in polymeric vesicles, despite a modest increase in Km.

Heparinized surfaces exert a strong anticoagulant activity by delaying the onset of surface induced thrombin generation [Merrill et al. (1970) *Journal of Applied Physiology* 29(5):723–730; Basmadjian et al. (1983) *Journal of Biomedical Materials Research* 17(3):509–518; Goosen et al. (1980) *Thrombosis Research* 20(5–6):543–554; Nojiri et al. (1990) *ASAIO Transactions* 36(3):M168–172; Byun et al. (1996) *Biotechnology Progress* 12(2):217–225; Byun et al. (1996) *J. Biomed. Mater. Res.* 30(4):423–427]. The extent of this effect is generally dependent on the surface density of heparin and the rate of delivery of ATIII to the heparinized surface. Early clinical studies evaluating the efficacy of end-point attached heparin coated coronary stents have reported promising results [van der Giessen et al. (1998) Seminars in *Interventional Cardiology* 3(3–4):173–176; Serruys et al. (1998) *Lancet* 352(9129):673–681; Buller et al. (1999) *Circulation* 100(3):236–242]. Nonetheless, several limitations of a heparin-based strategy exist. Blezer et al. (1998) *Throm. Haemostasis* 79(2):296–301 and (1997) *J. Biomedical Materials Research* 37(1):108–113, have observed that factor IXa, XIa, and thrombin are generated when recalcified human plasma contacts immobilized heparin either static or flow conditions. Thus, initiation of the contact activation pathway is not inhibited by ATIII associated with immobilized heparin. Moreover, at physiological concentrations of ATIII, the contribution of the heparinized surface to the inactivation of total circulating thrombin is negligible [Lindhout et al. (1995) *J. Biomed. Mater. Res.* 29(10):1255–1266]. This is an important consideration, particularly when one considers the potential for long-term expression of tissue factor at sites of vascular wall injury with consequent chronic thrombin generation at a site upstream to the implanted device. Heparin can be inactivated by factors released from activated platelets, such as platelet factor 4, and it is relatively ineffective in limiting the formation of platelet rich thrombus [Eitzman et al. (1994) *Circulation* 89(4):1523–1529]. Additionally, cases of heparin induced thrombocytopenia caused by heparin coated materials have been reported [Laster et al (12988) *J. Vasc. Surg.* 7(5):667–672]. TM, in contrast to heparin, not only inactivates thrombin by an ATIII mediated mechanism, but also markedly enhances thrombin's ability to activate protein C [Esmon, C. T. (1995) *FASEB Journal* 9(10):946–955]. Activated protein C together with its cofactor protein S inactivates two coagulation factor, VIIIa and Va, thereby preventing the generation of Xa and thrombin which are critical for the amplification of the coagulation cascade [Lu et al. (1996) *Blood* 87(11):4708–4717; vant Veer et al. (1997) *J. Biol. Chem.* 272(12):7983–7984]. Thus, unlike surface bound heparin, the release of activated protein C into the blood stream provides an efficient means for inactivating coagulation reactions that are localized on a surface or occur within the general vicinity of APC generation.

Membrane-mimetic films containing TM in an appropriate transmembrane orientation can be produced by a process of molecular self-assembly and in situ polymerization. Polymeric lipid films both limit contact activation and selectively inactivate thrombin through the appropriate choice of constituent lipid components and TM surface concentration. TM, as a component of a polymeric lipid assembly, can selectively activate protein C and effectively limit thrombin generation. Membrane-mimetic films containing TM have extended in vitro stability and bioactivity.

Model membrane-mimetic surfaces containing TM are produced on planar alkylated substrates formed on polymer, glass, gold, or silicon substrates. The formation of membrane-mimetic surfaces involves surface fusion of unilamellar phospholipid vesicles, followed by in situ photopolymerization and has been described in detail. Recent studies suggest that protein C best binds onto lipid membranes that contain both phosphatidylcholine and phosphatidylethanolamine [Smirnov et al. (1999) *Biochemistry* 38(12) 3591–3598; Smirnov et al. (1994) *J. Biol. Chem.* 269(2) :816–819]. Moreover, the PE headgroup can contribute to the catalytic efficiency of APC, particularly with respect to factor Va inactivation. TM is incorporated at different molar concentrations to a baseline DPPC surface ($1:10^4$–$1:10^6$) and to surfaces composed of different molar ratios of phosphatidylcholine and phosphatidylethanolamine phospholipids (0–50 mol %) at a single TM concentration. Finally, the ability to generate stable surface microdomains with locally enhanced membrane dynamics examined by utilizing mixed assemblies comprising polymerizable lipids (e.g. monoacrylDPPC) and nonpolymerizable lipids (e.g., DPPC). This allows us to determine the effect of generated "molecularly-mobile" microdomains on membrane anticoagulant properties. Morphological, structural, and chemical properties of substrate supported films are investigated by techniques, including contact angle goniometry, ESCA, external reflectance IR and Raman spectrosocopy, as well as by high resolution SEM and AFM. Membrane dynamics are studied using fluorescence recovery after photobleaching (FRAP) techniques coupled with confocal fluorescence microscopy. We determine the molecular diffusivities of fluorescently tagged lipids and TM as a function of alkylated substrate type (HEA:AOD:MTEM vs HEA:AOD:SS), lipid microenvironment (PC vs PE), and extent of 2-D polymerization (% AcPC). Effective TM surface concentration is determined by measuring Gla domainless-protein C (GD-PC) activation.

$K_m$ and $k_{cat}$ values for the activation of protein C are dependent upon the species source for TM and protein C (e.g., bovine vs. rabbit vs. human). All studies described herein are conducted with human TM and protein C unless otherwise indicated. A high degree of sequence homology exists (>98%) between human and baboon cDNA species encoding for a variety of proteins (Hayzer et al. (1993) *Gene* 127:271–272; Shoji et al. (1993) *Gene* 133:307–308; Shoji et al. (1993) *Gene* 133:307–308; Hayzer et al. (1999) *Throm. Res.* 98:195–201]. Recombinant human soluble TM is capable of activating protein C and limiting thrombin generation when injected into baboons. No acute allergic reactions were observed. High resolution SEM and AFM investigations provide topological data regarding the surface distribution of TM, including assessment of protein clustering in phase separated regions. Fluorescently labeled TM in conjunction with confocal fluorescence microscopy of antibody labeling of TM using gold or chromophore labeled primary or secondary antibodies allows detection. TM has a short cytoplasmic domain that consists of 38 amino acids, a 23 amino acid transmembrane domain and a 496 amino acid extracytoplasmic domain that also contains a chondroitin sulfate chain comprised of 25 disaccharide units. The membrane-mimetic surface consists of a lipid monolayer supported on an alkylated terpolymer. The terpolymer film is a multi-component structure consisting of anchoring groups and an HEA hydrophilic cushion on top of which lies a self-assembled array of C16 alkyl chains. Current thickness estimates for the HEA hydrophilic cushion are approximately 100 A [Marra et al. (1997) *Langmuir* 13:5697–5701].

Thus, due to steric hindrance considerations alone, the extracytoplasmic TM domain orients itself on the outside of the membrane-mimetic film and not within the hydrophilic cushion of the supporting terpolymer base layer. Nevertheless, the potential to further tailor the dimensions of the terpolymer cushion in order to improve TM orientation and bioactivity exists. In situ polymerization of acrylated lipids facilitates the generation of a stable membrane-mimetic film. Nevertheless, the optimal assembly of TM with protein C and thrombin may be dependent on their 2-D movement within the planar lipid membrane. Mixed lipid systems that include nonpolymerizable lipid molecules can also be used. Alternate design strategies are illustrated below. See Schemes 6A–6B.

Although lipid membranes composed of phosphatidylcholine head groups reportedly do not initiate contact activation, most artificial surfaces, including heparinized materials, activate the intrinsic pathway of the coagulation system [Blezer (1998) supra]. In order to determine if TM containing membrane-mimetic films initiate blood coagulation, two test systems are utilized: supported lipid films and polymeric lipid vesicles. Supported lipid films are produced on circular glass cover slips (d 20 mm), placed in multiwell plates, and exposed to citrated platelet free human plasma. Clotting is initiated by the addition of calcium to a total concentration of 4 mM. Samples are taken from the reaction mixture over 90 minute period and assayed for factor XIa, IXa, Xa, thrombin production and generation of APC. The effect of surface induced protein C activation is determined by selectively repeating these investigations using protein C depleted plasma (George King Biomedical, Overland Park, Kans.). In a second experimental system, various concentrations of polymeric lipid vesicles are substituted for planar glass coated surfaces in order to maximize test surface area. Factor XIa, IXa, Xa, thrombin activity and APC levels are measured after recalcification of citrated platelet free human plasma. Given vesicle dimensions determined by quasi-elastic light scattering, total phospholipid concentration, and published dimensions for head group surface area, the total vesicle concentration and exposed membrane surface area can be determined readily.

Recalcified platelet free human plasma, as a model to study the dynamics of blood clotting has been validated by a variety of investigators [3 lezer (1998) supra; Kawamoto et al. (1992) *Blood Coagulation & Fibrinolysis* 3(4): 371–379]. A synthetic plasma mixture prepared with purified coagulation proteins and inhibitors is an established alternative [van't Veer et al. (1998) supra; Rand et al. (1996) *Blood* 88(9):3432–3445; Brummel et al. (1999) *J. Biol. Chem.* 274(32):22862–22870]. There are several known physiologic inhibitors of activated protein C, including protein C inhibitor (PCI), $\alpha_1$-antitrypsin ($\alpha_1$-AT), and $\alpha_2$-macroglobulin. These inhibitors are stable in pooled citrated human plasma, as is protein C. The rates of interaction of APC with PCI, $\alpha_1$-AT and $\alpha_2$-macroglobulin are unaffected by other plasma components. The APC inhibitory pathway is identical in humans and baboons. Thus, data generated with pooled human plasma are relevant to baboon experiments. Nonetheless, the ability to use ELISA to measure plasma levels of all components of the protein C pathway, including inhibitory factors, exists, and has been reported [Espana et al. (1991) *Blood* 77(8):1754–1760]. Activation of the intrinsic pathway of the clotting cascade in test wells composed of non tissue culture treated polystyrene is limited [Blezer (1997) supra]. However, background activity is examined with appropriate controls. Surface functional properties are dependent on the transport of reactants from the solution to the surface. Even well-stirred systems do not necessarily mimic the protein flux achieved under arterial or venous flow conditions in vivo; however, in vitro static assays of blood coagulation provide a simple means for an initial assessment of the surface bioactivity of a potentially large number of different test samples. The ability to conveniently vary the amount of exposed surface area to enhance the sensitivity of the test system is a distinct advantage of using polymeric lipid vesicles. However, vesicles only approximate the structure of planar lipid films, since they consist of a true polymerized bilayer and not a polymeric lipid monolayer supported on an alkylated terpolymer ionically linked to a hydrogel substrate. Such planar lipid films provide useful information.

In order to determine the role of TM-containing lipid assemblies in limiting the propagation phase of blood coagulation, test surfaces are exposed to citrated platelet free human plasma spiked with 20 $\mu$M unilamellar vesicles composed of 25 mol % DOPS/75 mol % DOPC [Blezer (1997) supra]. These vesicles mimic lipid composition of procoagulant platelet phospholipid membranes, thereby facilitating the assembly of the factor X activating complex (tenase). Clotting is initiated by the addition of calcium to a final concentration of 4 mM and samples taken from the reaction mixture over 90 minutes are assayed for factor Xa, activated protein C, and thrombin production. The approximate proportion of thrombin accessible to the procoagulant pathway is determined by measuring fibrinopeptide A formation. Test samples include polymeric lipid vesicles and/or supported planar polymeric lipid films.

Contact suppressed whole blood, containing corn trypsin inhibitor as an inhibitor of factor VIIa, is an established alternative to recalcified platelet free human plasma in the investigation of the propagation phase of blood coagulation [van't Veer supra; Rand (1996) supra; Brummel et al. (1999) *J. Biol. Chem.* 274(32):22862–22870].

The films described herein have sufficient biostability for both in vitro studies and in vivo use. Even in non-polymerized forms, liposomes persist for days or even weeks at the site of subcutaneous injection [Mauk et al. (1980) *Science* 207:309–311]. Other studies have also determined that surfaces modified with a variety of biomacromolecules retain molecule specific bioactivity for prolonged periods in vitro and in vivo [Imanishi, Y., (1992) CRC Press, Boca Raton, Fla.; Nojiri et al. (1996) *ASAIO Journal* 42(5): M468–475].

Film stability is initially assessed by incubation of samples in PBS and citrated human plasma at 23 and 37° C. Changes in TM surface concentration are determined by measuring the GD-PC activation rate. Additional surface-sensitive techniques to assess changes in film physical and chemical properties are performed on a selective basis. These studies can determine if there is significant loss of TM activity through direct desorption or due to the effect of binding interactions with serum proteins or naturally occurring surfactant molecules. Finally, in most clinical applications, blood-contacting surfaces are subjected to wall shear rates of 20 dyn/cm$^2$ or less. Therefore, films are also analyzed after PBS exposure to a continuous shear stress (20 and 200 dyn/cm$^2$) for up to 120 minutes in a parallel plate flow chamber.

The effect of biochemical factors on membrane stability is determined. Test surfaces are incubated in the presence of endothelial cells using a dual chamber co-culture system (Falcon, Inc.) consisting of a 24-well plate fitted with porous inserts (0.45 $\mu$m pore size). Endothelial cells are cultured in the insert, and test substrates are placed in the underlying well. Replacement of the well insert with newly cultured endothelial cells may be required, depending on the duration of the experiment. At various time intervals (0,24 h, 48 h, 96 h, 1 wk, 2 wk, and 4 wk), test substrates are removed, and changes in TM surface concentration are determined by measuring the GD-PC activation rate. Incubation of the samples in PBS alone or PBS with phospholipase C at weight ratios of lipase to lipid of 1:20, 1:100, and 1:1000 serves as negative and positive controls, respectively. Additional surface sensitive techniques to assess changes in film physical and chemical properties are performed on a selective basis.

While biostability investigations have been promising, alternate synthetic routes for polymerizable lipids are available, including the generation of phospholipids with ether linkages that are less susceptible to hydrolysis than the naturally occurring ester groups. Prior studies have demonstrated that covalently coupled TM retains some biological activity. We believe it valuable to explore the effect of membrane dynamics on TM activity. When lipid molecular mobility have a dramatic impact on surface catalytic efficiency, it is possible that films with "molecularly-mobile" microdomains have compromised long-term film stability. One possible failure mode includes the loss of DPPC and TM from non-polymerized lipid domains. If so, alternate synthetic routes for the generation of a molecularly mobile membrane exist, as previously discussed. However, an additional option includes the use of lipids containing longer alkyl chains (>C16, and up to about C32). Increased intermolecular van de Waal interactions enhance the stability of free lipids, albeit with some reduction in membrane fluidity. In order to confirm the loss of free or polymeric lipid molecules as a possible cause of film instability, the extent of lipid loss can be determined by use of $^{14}$C-labeled lipids or fluorescently tagged lipid conjugates coupled with either confocal microscopy or total internal reflectance fluorescence (TIRF) spectrosocopy.

The local hemodynamic environment is a critical regulatory factor in blood coagulation [Hanson et al. (1998) *Am. Heart Journal* 135(5 Pt 2 Su):S132–145; Slack et al. (1993) *Thromb. Haemostasis* 70(1):129–134; Turitto et al. (1998) *Thromb. Res.* 92(6 Suppl. 2):S25–310. The progress of coagulation reactions is fundamentally different during flow or under static conditions. The type of flow regime, including the magnitude of the wall shear rate, influences both conversion rates of coagulation proteins at a catalytic surface and removal rates of formed products. An example of this effect is the enhanced catalytic efficiency of the Factor X activation complex (tissue factor: factor VIIIa) noted with increasing wall shear rate in a tubular flow reactor [Gemmell et al. (1990) *Microvasc. Res.* 40(30):327–340; Gir et al. (1996) *Ann. Biomed Eng.* 24(3):394–399; Hall et al. (1998) *J. Biomech. Eng.* 120(4):484–490]. Specifically, a three-fold increase in Vmax was noted, as the shear rate increased from 25 to 300 sec$^{-1}$. Forces generated by flow are capable of including changes in the structural conformation of a variety of enzymatic complexes and, as a consequence, may alter their kinetic behavior [Gemmell et al (1990) *Blood* 76(11): 2266–2271; Gentry et al. (1995) *Biophys. J.* 69(2):362–371; Nemerson et al. (1991) *Thromb. Haemostasis* 66(3): 272–276; Bjorquist et al. (1997) *Thromb. Res.* 85(3): 225–236]. Nonetheless, the interdependence of blood flow and surface reactivity lies primarily in the flow-mediated transport of plasma proteins to and from an interface. As such, the overall coagulation rate is dependent not only upon the chemical reaction kinetics at the interface, but also on the mass transfer conditions dictated by fluid connection and molecular diffusion [Basmadjian et al. (1997) *Biomaterials* 17(23):1511–1522]. Therefore, mass transfer coefficients reflect both the rate at which pro- or anticoagulants are conveyed to the reactive surface and the rate of removal of intermediates and products. The latter are important participants in the positive and negative feedback loops that regulate the coagulation process. Several monographs summarize the principles and methodologies necessary for the investigation of coupled processed at reactive solid-liquid interfaces under varying flow conditions [See, e.g., Kobayashi et al. (1974) *Biotech. Bioeng.* 16(1):77–97; Kobayashi et al. (1974) *Biotech. Bioeng.* 16(1):99–118; Goldsmith et al. (1986) *Thromb. Haemostasis* 55(3):415–435; Slack et al (1994) *Thromb. Haemostasis* 72(5):777–781; Andree et al. (1994) *Biochemistry* 33(14):4368–4374].

Shear dependent experimental models of thrombosis have impacted the evaluation of the preclinical efficacy of antithrombotic agents and have helped refine our understanding of the optimal mode of action and shear dependent effects [Hanson (1998) supra]. Likewise, improving the clinical performance characteristics of an implanted device requires a fundamental understanding of the behavior of the biomaterial surface within the imposed constraints of a local hemodynamic environment. For example, Amander et al. (1988) *J. Biomed Mater. Res.* 22(10):859–868 have demonstrated that blood flow influences the performance of a heparanized arteriovenous shunt. At low but not high flow rates, fibrinopeptide A was generated, suggesting that, at least under these conditions, circulating thrombin had more time to convert fibrinogen to fibrin before inactivation at the heparinized surface. Similarly, Lindhout et al. (1995) supra, have observed that the rate of thrombin inhibition at heparinized surfaces is transport limited, largely due to limitations imposed by the rate of ATIII delivery to the surface. Both studies imply that heparinized surfaces are best suited for a high shear flow environment. Paradoxically, plateletdependent thrombus, which is normally produced at arterial shear rates, is heparin-resistant [Hanson (1988) supra]. In contrast, systemic administration of activated protein C markedly reduces venous and arterial type thrombosis. This phenomenon has been characterized in a variety of experimental animal models, including those studying the induction of thrombus formation on the surface of a vascular prosthesis [Gruber et al (1989) *Blood* 73(3):639–742; Gruber et al. (1990) *Circulation* 82(2):578–585; Espana (1991) supra; Gruber et al (1991) *Circulation* 84(6):2454–2462].

The catalytic efficiency ($k_{cat}$/Km) of TM under flow conditions is similar whether reconstituted within polymeric or non-polymeric lipid films. TM containing films are antithrombogenic under both arterial and venous flow conditions. A kinetically limited regime for APC production has been defined at venous (50 sec$^{-1}$) and arterial flow rates (500 sec$^{-1}$); the intrinsic kinetic parameters for APC production and the effect on these parameters of shear rate, lipid head group composition, and membrane dynamics have been defined; and we have identified whether the rate of formation of the protein C-activating complex is a diffusion or reaction controlled process. The methodological approach in all of these studies is based on the use of a capillary tube flowreactor system, as detailed by Blezer (1998) supra; Billy et al. (1995) *J. Biol. Chem.* 270(3):1029–1034; Contino et al. (1994) *Biophys. J.* 67(30:1113–1116. This technique has been used extensively in studying the effect of flow rates on lipid membrane based processes. Briefly, a glass capillary tube (0.65 mm id and 127 mm length) is coated with a membrane-mimetic film and attached to a Hamilton syringe. The flow rate of the test solution is controlled by a syringe pump, and timed samples are collected from the tip of the flow reactor. All studies are conducted at 37° C. In addition to photopolymerized lipid films, TM is incorporated into vesicles comprised of non-acrylate containing lipid molecules (e.g. POPC, DL$_2$PE, etc.) for fusion onto the inner wall of glass capillary tubes. The reconstitution of TM into a lipid coating comprised of native phospholipids serves as a reference point for studies described herein. The data generated using this reference system closely mimics the true microenvironment of the cell membrane in the body.

Experiments to define a kinetically limited regime for APC production involve the perfusion of coated capillaries with activation buffer (20 mM Tris-HCl pH 5.5) containing 100 mM NaCl, 5 mg/mL BSA, 5 mM Ca$^{2+}$, protein C (0.1 µM), and thrombin (10 nM). APC production is determined as a function of TM surface density at venous and arterial shear rates. Transport limitations have a significant impact on the behavior of these systems. Therefore, these experiments define, for a given flow regime, a TM surface density above which APC production becomes independent of TM concentration due to mass transfer limitations.

The intrinsic kinetic parameters for APC production are assessed in a kinetically limited regime by perfusion of coated capillary tubes with activation buffer containing thrombin (10 nM) (with varying concentrations of protein C (0.01–4 µM). In all cases, capillary tubes are preperfused with thrombin alone for 10 min. Rates of APC production are determined from the steady state levels of APC measured at the outlet of the flow reactor. Kinetic parameters, $k_{cat}$ and Km are obtained by non-linear regression analysis of observed rates of APC production as a function of protein C concentration in the perfusion solution. The effect on these parameters of shear rates (50 sec$^{-1}$ vs. 500 sec$^{-1}$) and lipid head group composition (i.e. varying molar ratios of phosphatidylcholine to phosphatidylethanolamine) are determined. In addition, where mixed membrane-mimetic assemblies comprised of polymeric and non-polymeric lipids are found to be sufficiently stable, kinetic parameters are defined for these systems, as well. Finally, kinetic parameters are compared to those values reported for TM complexes inserted into POPC vesicles [Galvin et al. (1987) *J. Biol. Chem.* 262(5):2199–2205], as well as to those derived for TM complexes inserted into lipid vesicles composed wholly, or in part, of polymeric lipids.

The rate of formation of the protein C-activating complex (i.e. TM:thrombin) is estimated under arterial and venous flow conditions and defined as a diffusion or reaction controlled process. Membrane coated capillary tubes are perfused with activation buffer containing protein C (0.1 µM) and varying amounts of thrombin (0.1–10 nM), and APC production is measured at the reactor outlet. The time to reach steady state levels of APC production decreases with increasing amounts of thrombin in the perfusion solution. The initial part of the APC generation curve, therefore, reflects the rate of formation of APC generating activity at the membrane-mimetic surface, and this rate increases with increasing amounts of thrombin in the perfusion mixture. The experimental rate of APC production is compared to the calculated rate of thrombin mass transfer to the catalytic surface in order to determine whether formation of the protein C activating complex is a transport or kinetically limited process.

Protein C activation by a TM containing membrane-mimetic system is an efficient process, as evidenced by low concentrations of protein C required to obtain half-maximal velocity of APC production. Nonetheless, it may be difficult to achieve a catalytic efficiency identical to that obtained for TM inserted into non-acrylate containing native membrane mimics due to the polymeric nature of the membrane-mimetic system. This can be circumvented by modest increases in the surface concentration of TM, and alternative strategies to increase membrane dynamics within these artificial systems have been described above. A distinct advantage of the capillary flow reactor is its large catalytic surface area. In order to confirm that surface properties for films generated on either planar or tubular surfaces are similar, the effective TM surface concentration for coated tubes is determined by measuring Gla domainless-protein C activation. In addition, one can assess the uniformity of surface coating using chromophore conjugated lipid probes. Phospholipid films have been coated onto capillary tubes, and the use of parallel plate flow chambers, however, is an alternative option.

The antithrombogenic properties of TM containing membrane-mimetic films are examined under arterial (500 $sec^{-1}$) and venous (50 $sec^{-1}$) flow conditions. As described above, a capillary tube flow reactor system can be used. Recalcification of citrated platelet free human plasma or the addition of other initiators of the coagulation cascade, such as thrombin or tissue factor, occurs by mixing these factors into the perfusate just before entrance into the flow reactor. All studies are conducted at 37° C.

Experiments to define the ability of membrane-mimetic films to limit the propagation of blood coagulation when initiated via the intrinsic pathway involve the perfusion of coated capillaries with recalcified platelet-free human plasma. Samples are collected from the outlet of the flow reactor and assayed for factor XIa, IXa, Xa, APC and thrombin production. The effect of surface-induced protein C activation in this system is determined by measuring clotting factor activation in the presence of TM-free membrane systems. To potentiate the propagation of blood coagulation, experiments are selectively repeated with recalcified platelet free human plasma spiked with 20 $\mu M$ of unilamellar vesicles composed of 25 mol % DOPS/75 mol % DOPC. These vesicles mimic the lipid composition of procoagulant platelet phospholipid membranes and facilitate the assembly of the factor X activating complex (tenase).

The ability of membrane mimetic films to limit blood coagulation when initiated via the extrinsic pathway is examined. These investigations involve the perfusion of coated capillaries with recalcified platelet free plasma spiked with varying concentrations of tissue factor (12–100 pM) reconstituted into unilamellar vesicles composed of 25 mol % DOPS/75 mol % DOPC. Samples at the flow reactor outlet are collected and assayed for factor Xa, APC and thrombin production. The approximate proportion of thrombin accessible to the procoagulant pathway is determined by measuring fibrinopeptide A formation. The effect of surface induced protein C activation is determined by measuring clotting factor activation in the presence of TM-free membrane systems.

To estimate the rate of formation of direct thrombin inactivation complexes (TM:ATIII), coated capillary tubes are perfused with Hepes buffer containing 15 nM of thrombin and 20 nM of antithrombin. At timed intervals samples are collected and assayed for residual thrombin activity and thrombin-antithrombin III (TAT) complex formation. Thrombin inactivation activity is compared to the known ATIII-binding capacity of the membrane as described herein.

To examine antithrombogenic film properties in the presence of thrombin containing human plasma, coated capillaries are perfused with recalcified platelet free plasma spiked with varying concentrations of thrombin (10–100 nM). Samples at the flow reactor outlet are collected and assayed for factor Xa, APC, thrombin and fibrinopeptide A formation.

The properties of a small diameter vascular graft coated with a TM functionalized membrane mimetic surface film at the blood- and tissue-materials interface in vivo are characterized as follows. A number of reports have documents the feasibility of surfaces modified with PC in preventing platelet adhesion and activation in vitro (Ishihara et al. (1994) Biomaterials 28:225–232; Hall et al. (1989) 10(4):219–224). Hanson and colleagues (Chen et al. (1997) Ann. Vasc. Surg. 11(1): 74–79) have reported in a canine artery model that graft neointimal hyperplasia and cell proliferation were reduced in standard ePTFE prostheses coated with a PC containing copolymer, suggesting that the PC headgroup is bioactive in vivo and that a membrane mimetic strategy might improve the performance of implanted vascular grafts. We demonstrate herein that the incorporation of TM into a membrane mimetic surface creates an antithrombogenic interface, and the methods described herein allow for significant improvement in the antithrombogenic activity in the blood contacting materials of the present invention. Combining membrane mimetic and protein C activation strategies is useful. Clinical studies have yet to conclusively demonstrate that antithrombins reduce restenosis after coronary angioplasty. However, this failure may relate more to the inability to safely inhibit thrombin by systemic administration of an antithrombin than to a lack of a role for thrombin in restenosis. Local delivery of thrombin inhibitors, as with the TM containing membrane mimetic materials offers significant benefits in preventing the deleterious and dangerous sequellae to graft implantation and/or contact of blood with synthetic medical devices and materials. The clinical durability of a small vascular graft by limiting thrombus formation requires a membrane mimetic strategy that locally activates the endogenous protein C anticoagulant pathway, as taught herein.

The following issues are addressed using both a baboon ex vivo femoral arteriovenous shunt model and direct in vivo implant studies: kinetics and magnitude of protein C activation, plasma protein adsorption, platelet adhesion and activation and graft patency; short and long term stability of the biomimetic materials of the present invention; and the magnitude of the neointimal hyperplastic response.

Baboons are hemostatically similar to humans. Despite the well known effects of heparin for reducing restenosis in rabbits and rats after angioplasty, heparin in a similar study failed to reduce restenosis in baboons (175). Likewise, the ACE inhibitor cilazapril markedly reduced intimal hyperplasia in rats but fails to reduce lesion size in baboons. In addition, studies in primates are important for testing materials for medical use in humans.

Membrane mimetic surfaces containing TM or tTM induce minimal platelet and fibrinogen deposition and are essential for reducing thrombus formation in small diameter vascular grafts. Reduction in anastomotic neointimal hyperplasia is achieved by following a membrane mimetic that incorporates an activator of the endogenous protein C anticoagulant pathway.

Film composition, including the surface concentration of TM or tTM, is dictated by in vitro studies, as described herein. Composite prostheses (or other blood contacting materials) are fabricated by first impregnating the graft wall (6 mm id ePTFE) with gelatin followed by coating of the lumenal surface of the material with alternative polyelectrolyte layers of alginate and PLL. Subsequent formation of an alkylated layer on the lumenal surface of the prosthesis is achieved using an amphiphilic terpolymer. The prosthesis or other material is then incubated with polymerizable functionalized phospholipids and an aqueous mixture of lipid vesicles followed by in situ polymerization of the self assembled lipid membrane, as described herein. Surface characterization is performed using ESCA, contact angle goniometry, high resolution SEM and surface TM concentration measured by the GD-PC activation assay. Uniformity of film coating is determined using chromophore labeled lipid probes combined with epifluorescent microscopy.

The limitations of short term blood contacting studies in predicting the risk of surface induced thromboses are well known in the art. Nonetheless, characterization of the performance of the materials of the present invention using acute blood-contacting assays provides a convenient screening mechanism for a large array of surface compositions. A baboon ex vivo femoral arteriovenous shunt model is used to evaluate acute platelet and fibrinogen deposition in well defined flow regimes. A test sample is placed in the shunt and exposed to $^{111}$In labeled platelets for up to 120 minutes at a wall shear rate of either 50 sec$^{-1}$ or 500 sec$^{-1}$. Platelet deposition is monitored by scintillation camera imaging. Adsorption of injected $^{125}$I labeled fibrinogen is determined at the end of the blood exposure period by gamma counting. Using $^{125}$I labeled fibrinogen as a marker of plasma adsorption reveals whether platelets adhere to and are activated by the primary surface or via an adsorbed plasma protein/fibrin film. Several in vivo plasma assays of markers which are elevated upon activation of platelets and coagulation enzymes are utilized in these studies. Consumption of fibrinogen and its cleavage by thrombin is assessed by measurements of plasma clottable fibrinogen and fibrinopeptide A (FPQ) levels. Activation of platelets is judged from the change in circulating platelet count and by plasma levels of releasable platelet α-granule protein, β-thromboglobulin and platelet factor 4. Fibrinolysis is estimated by measuring circulating levels of fibrin D-dimer fragment. Activated partial thromboplasmin time (APTT) measurements are performed using citrated plasma samples. Significantly, the degree of surface induced thrombin formation is determined by measuring levels of thrombin-antithrombin III complexes. See Hanson et al. (1993) J. Clin. Invest. 92(4):2003–2012 for methods. Use of radiolabeled or chromophore labeled conjugates within the lipid film allow characterization of biostability (short term) in a blood contacting environment. Platelet and protein deposition on the lumenal surfaces of small caliber grafts are compared with alginate/PLL and with alginate/PLL/terpolymer coatings are compared. Because of the high homology between baboon and human TM, human TM and tTM are used in the baboon model.

For studies conducted under arterial shear rate conditions, prostheses are deployed in the carotid and iliac arteries of a primate model. Using both iliac and carotid arteries for these studies, at least 40 arterial sites are used. Films tested are a simple PC phospholipid membrane mimetic assembly and a membrane mimetic film containing TM or tTM as compared with an uncoated graft of the same synthetic material, e.g., ePTFE. Following graft implantation, patency is established initially and prior to sacrifice at 30 days or 6 months after implantation by Duplex imaging with associated arterial volume flow measurements as described by Zierler et al. (1992) J. Vasc. Surg. 16(4):520–526. By one month, ingrowth extends about 1 cm into the graft and a significant anastomotic neointimal lesion is present, obstructing about 10% of the graft lumen. These finding are reproducible. Intimal area and the extent of pannus in growth increase progressively between 1 and 6 months, with little further change up to 12 months.

Prior to graft harvesting, animals receive intravenous injections of Evans Blue, which enters the graft wall where endothelium is absent and bromodeoxyuridine (BrdU) for measurements of cell proliferation. At the time of explantation, grafts are opened longitudinally and photographed for measurements of thrombus free surface and overall pannus tissue in growth, which in control studies with ePTFE grafts averages about 1 cm/month. Serial sections of the adjacent artery are obtained at about 5 mm intervals for examination by scanning electron microscopy and light microscopy. Thus, there is histological reconstruction of healing events along the entire graft length (as described in Hanson et al. (1991) Hypertension 18(4Suppl): I170–I176). Staining is performed for examination of endothelial and smooth muscle cell coverage, as well as associated arterial wall cellular and matrix responses. For example, immunohistochemical studies include staining with endothelial factor VIII/von Willebrand factor to identify endothelial cells, smooth muscle α-actin to identify smooth muscle cells and Ham56 to identify macrophages. Neointimal hyperplasia (of the inner capsule of the graft) is assess by established quantitative computerized morphometric techniques.

Although the vascular prostheses have been evaluated in a canine model, primate studies are preferred. The baboon is particular preferred. Prothrombin time is somewhat longer in baboon than in man, but the activated partial prothrombin time (PTT), fibrinogen level, Factor VIII clotting activity and thrombin time (TT) are similar in man and baboon. Additionally, baboon and human Factor VIII antigens cross react and the platelets of both species are equivalent in size distribution, number of dense bodies and responsiveness to collagen, ristocetin and arachadonic acid. In contrast, the dog has very active hemostatic and fibrinolytic systems and platelets, which are readily activated by heparin. The PT, PTT and TT are significantly reduced whole fibrinogen and Factor VIII are elevated in dog relative to man. Although the porcine animal model has been used to study vascular wall injury, many of the reagents used in human studies cross react with primate cells but not with dogs, swine and other animal models. Additionally, standard commercial vascular grafts are spontaneously endothelialized in pig models but not in man or primates.

Animals are housed in animal care facilities staffed by veterinarians. The site is equipped with standard operating and postoperative care rooms. Major surgical procedures are performed aseptically and monitored appropriately after the surgery. Ketamine HCl (200–250 mg IM) is used for sedation and sodium pentobarbital (50–75 mg IV pm) is used for anaesthesia. Intravenous injections of barbiturate and potassium chloride are used for euthanasia in a manner consistent with the recommendations of the Panel of Euthanasia of the American Veterinary Medical Association.

Monoclonal or polyclonal antibodies, preferably monoclonal, specifically reacting with a particular protein of interest may be made by methods known in the art. See, e.g., Harlow and Lane (1988) *Antibodies: A Laboratory Manual*, Cold Spring Harbor Laboratories; Goding (1986) *Monoclonal Antibodies: Principles and Practice*, 2d ed., Academic Press, New York, N.Y.; and Ausubel et al. (1993) *Current Protocols in Molecular Biology*, Wiley Interscience, New York, N.Y.

Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al. (1989) *Molecular Cloning*, Second Edition, Cold Spring Harbor Laboratory, Plainview, N.Y.; Maniatis et al. (1982) *Molecular Cloning*, Cold Spring Harbor Laboratory, Plainview, N.Y.; Wu (ed.) (1993) *Meth. Enzymol.* 218, Part I; Wu (ed.) (1979) *Meth. Enzymol.* 68; Wu et al. (eds.) (1983) *Meth. Enzymol.* 100 and 101; Grossman and Moldave (eds.) *Meth. Enzymol.* 65; Miller (ed.) (1972) *Experiments in Molecular Genetics*, Cold Spring Harbor Laboratory, Cold Spring Harbor, N.Y.; Old and Primrose (1981) *Principles of Gene Manipulation*, University of California Press, Berkeley; Schleif and Wensink (1982) *Practical Methods in Molecular Biology*; Glover (ed.) (1985) *DNA Cloning* Vol. I and II, IRL Press, Oxford, UK; Hames and Higgins (eds.) (1985) *Nucleic Acid Hybridization*, IRL Press, Oxford, UK; Setlow and Hollaender (1979) *Genetic Engineering: Principles and Methods*, Vols. 1–4, Plenum Press, New York; and Ausubel et al. (1992) *Current Protocols in Molecular Biology*, Greene/Wiley, New York, N.Y. Abbreviations and nomenclature, where employed, are deemed standard in the field and commonly used in professional journals such as those cited herein.

All references cited in the present application are incorporated by reference herein to the extent that there is no inconsistency with the present disclosure.

The following examples are provided for illustrative purposes, and are not intended to limit the scope of the invention as claimed herein. Any variations in the exemplified articles which occur to the skilled artisan are intended to fall within the scope of the present invention.

EXAMPLES

Example 1

Synthesis and Terminal Functionalization of Polymerizable Phosphatidylethanolamine Thin layer chromatography (TLC) was performed on Whatman silica gel aluminum baked plate (F254, 250 mm thickness) and detected by fluorescence quenching, sulfuric acid (10 ml % in methanol), or phosphomolybdic acid (20 wt % in ethanol). Column chromatography was performed on silica gel (Fisher Chemical, 200–425 Mesh). $^1$H and $^{13}$C NMR spectra were recorded at 300 and 75 MHz (Varian INOVA) in $CDCl_3$, $CD_3OD$ (internal $Me_4Si$, d=0). Mass spectra (EI, FAB) were measured with JEOL JMS-SX 102/SX102A/E mass spectrometer. Confocal microscopy studies were performed on a Zeiss LSM510 Laser Confocal Microscope (Carl Zeiss, Inc., Germany) equipped with external argon (for excitation at 458,488 and 514 nm), HeNe1 (for excitation at 543 nm) and HeNe2 (for excitation at 633 nm) lasers.

Mono-AcrylPC (1) was prepared as described by Marra et al. (1997) *Macromolecules* 30, 6483–6488.

3-O-(4-methoxybenzyl)-sn-glycerol (3) was prepared from (+) 1,2-O-isopropylidene-glycerol according to the procedure described by Hebert et al. (1992) *J. Org. Chem.* 57, 1777–1783.

1-O-palmitoyl-3-O-(4-methoxybenzyl)-sn-glycerol (4) was prepared as follows. To a solution of 3-O-(4-methoxybenzyl)-sn-glycerol (3) (2.0 g, 9.4 mmol), palmitic acid (2.7 g, 10.4 mmol) and N,N-dimethylaminopyridine (0.06 g, 0.5 mmol) in dichloromethane (60 mL) was added a solution of dicyclohexylcarbodiimide (3.7 g, 18.0 mmol) in dichloromethane (10 mL) dropwise over a period of 45 min at 0° C. The reaction mixture was stirred for 18 hrs at room temperature under Ar atmosphere. Dicyclohexylurea was removed by filtering through celite, and the filtrate was evaporated to give a residue, which was purified by column chromatography ($SiO_2$) using ethyl acetate-n-hexane (1:3) as eluent to afford 4 (3.0 g, 71%). $^1$H NMR ($CDCl_3$) d: 7.24 (d, 2H, J=9.0 Hz, Ph), 6.88 (d, 2H, J=9.0 Hz, Ph), 4.48 (s 2H, $CH_2$—Ph), 4.14 (m, 1H, CH), 4.00 (m, 1H, CH), 3.80 (s, 3H, $OCH_3$), 3.51–3.46 (m, 2H, $CH_2$), 2.50 (d, 1H, J=5.1 Hz, OH), 2.31 (t, 2H, J=7.5 Hz, $CH_2CO$), 1.62–1.60 (m, 2H, $CH_2$), 1.25 (br. s, 24H, $CH_2X12$), 0.87 (t, 3H, J=7.2 Hz, $CH_3$). HR-MS (EI) calc. For $C_{27}H_{46}O_5$: 450.33453; observed 450.33331 M/Z.

1-O-palmitoyl-2-O-(12-acryloyloxy)dodecanoyl-3-O-(4-methoxybenzyl)-sn-glycerol (5) was prepared as follows. To a solution of 4 (2.5 g, 5.5 mmol), 12-acryloyloxy-1-dodecanoic acid (1.67 g, 6.7 mmol) and N,N-dimethylaminopyridine (0.06 g, 0.45 mmol) in dichloromethane (30 mL) was added a solution of dicyclohexylcarbodiimide (3.0 g, 13.4 mmol) in dichloromethane (10 mL) dropwise over a period of 20 min. at room temperature. The reaction mixture was stirred for 18 hrs at room temperature under Ar atmosphere. Dicyclohexylurea was removed by filtering through celite, and the filtrate was evaporated to give a residue, which was purified by column chromatography ($SiO_2$) using ethyl acetate-n-hexane (1:4) as eluent to afford 5 (3.0 g, 71%). $^1$H NMR ($CDCl_3$) d: 7.24 (d, 2H, J=9.0 Hz, Ph), 6.88 (d, 2H, J=9.0 Hz, Ph), 6.38 (dd, 1H, J=17.0, 1.5 Hz, CH=$CH_2$), 6.11 (dd, 1H, J=17.0, 10.5 Hz, CH=$CH_2$), 5.80 (dd, 1H, J=1.5, 10.5 Hz, CH=$CH_2$), 5.21 (m, 1H, CH-2), 4.48 (d, 1H, J=11.7 Hz, $CH_2$—Ph), 4.42 (d, 1H, J=11.7 Hz, $CH_2$—Ph), 4.31 (dd, 1H, J=3.9, 12.0 Hz), 4.16 (dd, 1H, J=6.0, 9.9 Hz), 3.78 (s, 3H, $OCH_3$), 3.54 (d, 2H, J=5.1 Hz), 2.33–2.24 (m, 4H, $CH_2COX2$), 1.67–1.55 (m, 6H, $CH_2X3$), 1.24 (br. s, 38H, $CH_2X19$), 0.89 (t, 3H, J=6.6 Hz, $CH_3$). $^{13}$C NMR ($CDCl_3$) d: 173.94, 173.60, 166.61, 130.66, 128.81, 72.26, 64.89, 62.35, 61.52, 53.89, 34.55, 34.45, 34.28, 32.11, 29.88, 29.66, 29.60, 29.55, 29.43, 29.31, 28.77, 26.10, 25.07, 22.30, 14.30. HR-MS (EI) calc. For $C_{42}H_{70}O_8Li$: 709.5231; observed 709.5211 M/Z.

1-O-palmitoyl-2-O-(12-acryloyloxy)dodecanoyl-sn-glycerol (6) was prepared according to the following. To a solution of 5 (2.5 g, 4.2 mmol) in dichloromethane/water (18:1, 20 mL) was added 2,3-dichloro-5,6-dicyano-1,4-benzoquinone (1.04 g, 4.6 mmol). The reaction mixture was stirred for 16 hrs at room temperature under Ar atmosphere. The reaction was quenched with $NaHCO_3$ and extracted with chloroform (20 mLX3). The combined organic portion were dried over anhydrous $Na_2SO_4$ and the solvent evaporated to give a residue, which was purified by column chromatography ($SiO_2$) using ethyl acetate-n-hexane (1:3) as eluent to afford 6 (1.4 g, 55%). $^1$H NMR ($CDCl_3$) d: 6.39 (dd, 1H, J=17.0, 1.2 Hz, CH=$CH_2$), 6.11 (dd, 1H, J=17.0, 10.8 Hz, CH=$CH_2$), 5.82 (dd, 1H, J=1.2, 10.8 Hz, CH=$CH_2$), 5.07 (m, 1H, CH-2), 4.31 (dd, 1H, J=4.2, 12.0 Hz), 4.26 (dd, 1H, J=4.2, 13.2 Hz), 4.13 (t, 2H, J=6.9 Hz, $CH_2$—O), 3.73 (t, 2H, J=4.2 Hz $CH_2OH$), 2.37–2.23 (m, 4H, $CH_2COX2$), 1.67–1.60 (m, 6H, $CH_2X3$), 1.24 (br. s, 38H, $CH_2X19$), 0.87 (t, 3H, J=7.2 Hz, $CH_3$). HR-MS (EI) calc. For $C_{34}H_{62}O_7Li$: 590.0035; observed 590.0021 M/Z.

1-O-palmitoyl-2-O-(12-acryloyloxy)dodecanoyl-sn-glycero-3-phosphoethyltrichloro ethoxycarbamate (7) was prepared as follows. To an ice-cooled solution of dichloro (N-b, b, b-trichloroethoxycarbonyl-2-aminoethyl)phosphate (1.5 g, 4.4 mmol) in dichloromethane (15 ml) was added dropwise a solution of 6 (1.2 g, 2.1 mmol) and triethylamine (1.8 mL, 13.5 mmol) in dichloromethane (10 ml). The reaction mixture was stirred for 16 hrs at room temperature under Ar atmosphere. Then washed with water (10 mL×3). The organic portion was dried over anhydrous $Na_2SO_4$ and the solvent evaporated to give 7 as a light brown syrup (1.36 g, 71%), which showed high purity in $^1$H NMR determination and showed the molybdenum blue positive on TLC (Rf=0.8 $CHCl_3/MeOH/H_2O$, 65:25:1). Thus it was directly used for the next reaction without purification.

1-O-palmitoyl-2-O-(12-acryloyloxy)dodecanoyl-sn-glycero-3-phosphoethanolamine (2) was prepared according to the following protocol. To a solution of crude7 (1.0 g, 1.0 mmol) in acetic acid (10 mL) was added Zinc dust (2.0 g). The reaction mixture was stirred for 20 hrs at room temperature. The reaction mixture was diluted with diethyl ether (30 mL) and filtered through celite. The filtrate was washed with water and aqueous $NaHCO_3$, and dried over anhydrous $Na_2SO_4$ and the solvent evaporated to give a residue, which was purified by column chromatography ($SiO_2$) using chloroform/methanol/water (65:25:4) as eluent to afford 2 (0.462 g, 62%). $^1$H NMR ($CDCl_3$) d: 8.51 (br, 3H, $NH_3^+$), 6.39 (dd, 1H, J=17.4, 1.0 Hz, CH=$CH_2$), 6.11 (dd, 1H, J=17.4, 10.5 Hz, CH=$CH_2$), 5.82 (dd, 1H, J=1.0, 10.5 Hz, CH=$CH_2$), 5.21 (m, 1H, CH-2), 4.37 (dd, 1H, J=3.0, 12.3 Hz), 4.14 (t, 2H, J=6.6 Hz, $CH_2$—O), 4.14–4.05 (m, 3H), 3.94 (br, 2H, $CH_2$—O), 3.16 (br, 2H, $CH_2$—N), 2.33–2.26 (m, 4H, $CH_2COX2$), 1.68–1.57 (m, 6H, $CH_2X3$), 1.24 (br. s, 38H, $CH_2X19$), 0.87 (t, 3H, J=6.6 Hz, $CH_3$). $^{13}$C NMR ($CDCl_3$) d: 173.59, 173.29, 166.48, 130.59, 128.83, 70.50, 64.86, 64.63, 64.09, 62.75, 62.44, 40.61, 34.44, 34.26, 32.11, 29.50, 29.41, 28.81, 27.79, 26.14, 25.13, 25.07, 22.87, 14.30. FABMS (M/Z): 728.6 $[M+Na]^+$.

mono-AcrylPE-FITC (8) was prepared as follows. To a solution of 2 (50 mg, 0.071 mmol) in DMF (5 mL) was added triethylamine (0.1 ml, 0.71 mmol). After the solution was stirred for 30 min., a solution of fluorescent isothiocyanate (55 mg, 0.142 mmol) was added. The reaction mixture was stirred for 12 hrs at room temperature in the dark, then concentrated in vacuum to give a residue, which was purified by column chromatography ($SiO_2$) using chloroform/methanol (4:1) as eluent to afford 8 (26 mg, 67%). $^1$H NMR ($CDCl_3$) d: 8.25 (br, 1H, Ph), 7.25 (br, 1H, Ph), 7.16–7.08 (m, 3H, Ph), 6.68 (m, 4H, Ph), 6.59 (dd, 1H, J=15.6, 1.5 Hz, CH=$CH_2$), 6.09(dd, 1H, J=15.6, 10.5 Hz, CH=$CH_2$), 5.82 (dd, 1H, J=1.5, 10.5 Hz, CH=$CH_2$), 5.17 (m, 1H, CH-2), 4.34 (dd, 1H, J=3.0, 12.3 Hz), 4.11 (t, 2H, J=6.6 Hz, $CH_2$—O), 4.13-4.02 (m, 3H), 3.94 (br, 2H, $CH_2$—O), 3.36 (br, 2H, $CH_2$—N), 2.27–2.23 (m, 4H, $CH_2COX2$), 1.66–1.54 (m, 6H, $CH_2X3$), 1.24 (br. s, 38H, $CH_2X19$), 0.83 (t, 3H, J=6.6 Hz, $CH_3$). FABMS (M/Z): 1096.2 $[M+1]^+$.

mono-AcrylPE-Biotin (9) was prepared as follows. To a solution of 2 (50 mg, 0.071 mmol) in DMF (5 mL) was added triethylamine (0.1 mL, 0.71 mmol). After the solution was stirred for 30 min., a solution of N-hydroxysuccinimidobiotin (36 mg, 0.11 mmol) was added. The reaction mixture was stirred for 24 hrs at room temperature, then concentrated in vacuum to give a residue, which was purified by Sephadex LH-20 column using methanol as eluent to afford 9 (17 mg, 53%). $^1$H NMR ($CDCl_3.CD_3OD$) d: 7.79 (br. 1H, NH), 7.00 (br, 1H, NH), 6.38 (dd, 1H, J=17.1, 1.0 Hz, CH=$CH_2$), 6.10 (dd, 1H, J=17.1, 10.5 Hz, CH=$CH_2$), 5.80 (dd, 1H, J=1.0, 10.5 Hz, CH=$CH_2$), 5.21 (m, 1H, CH-2), 4.48 (m, 1H), 4.35 (dd, 1H, J=3.0, 12.3 Hz), 4.32 (m, 1H), 4.13 (t, 2H, J=6.6 Hz, $CH_2$—O), 3.97 (br, 4H), 3.24 (br, 1H), 3.13–3.04 (br, 3H), 2.31–2.20 (m, 5H, $CH_2CO$), 1.70–1.57 (m, 6H, $CH_2X3$), 1.24 (br. s, 38H, $CH_2X19$), 0.85 (t, 3H, J=6.9 Hz, $CH_3$). FABMS (M/Z): 932 $[M+]^+$.

mono-AcrylPE-Biotin (10) was prepared as described: To a solution of 2 (25 mg, 0.035 mmol) in DMF (5 mL) was added triethylamine (0.05 mL, 0.35 mmol). After the solution was stirred for 30 min., a solution of N-(e-maleimidocaproyl)-Succinimide (22 mg, 0.11 mmol) was added. The reaction mixture was stirred for 24 hrs at room temperature, then concentrated in vacuum to give a residue, which was purified by Sephadex LH-20 column using methanol as eluent to afford 10 (23 mg, 71%). $^1$H NMR ($CDCl_3$) d: 7.19 (br, 1H, NH), 6.70 (s, 2H, CH=CH), 6.39 (dd, 1H, J=17.4, 1.2 Hz, CH=$CH_2$), 6.11 (dd, 1H, J=17.4, 10.5 Hz, CH=$CH_2$), 5.81 (dd, 1H, J=1.2, 10.5 Hz, CH=$CH_2$), 5.21 (m, 1H, CH-2), 4.37 (dd, 1H, J=3.0, 12.3 Hz), 4.29 (t, 1H, J=6.9 Hz), 4.14 (t, 2H, J=6.9 Hz, $CH_2$—O), 4.07–4.01 (m, 3H), 3.95 (br, 4H), 3.15 (br, 5H), 2.33–2.17 (m, 4H, $CH_2COX2$), 1.68–1.57 (m, 6H, $CH_2X3$), 1.24 (br. s, 38H, $CH_2X19$), 0.87 (t, 3H, J=6.6 Hz, $CH_3$). FABMS (M/Z): 907.2 $[M+1]^+$.

Example 2

Truncated TM Mutant Protein With a Gly-Gly-Cys C-Terminal Linker for Surface Conjugation A thrombomodulin fragment consisting of only the EGF-like domains 4, 5, 6 with a glycine-glycine-cysteine addition at the C-terminus (TMs) was expressed in *E. coli* as follows (FIG. 1). Human thrombomodulin cDNA, puc19TM15 (Accession No. 61348), was purchased from American Type Culture Collection, Manassas, Va. The DNA insert coding for TMs (residues 1200–1703) from full-length TM was obtained by the polymerase chain reaction using primers 5'-GAGATATACCATATGTACCCTAACTACGACCT GGTGGA-3' and 5'-CGCGCCTCGAGTTAATTAATTAG CAACCACCTATGAGCAAGCCCGAATGC-3' (SEQ ID NO:1 and SEQ ID NO:2, respectively). This 504-base pair NdeI and XhoI fragment of TM was cloned into a pET28a (+) expression vector (Novagen, Madison, Wis.), downstream of a T71ac promoter and a N-terminus His-tag coding sequence. The resulting plasmid, pET28aTMs, was verified by sequencing using the following primers: 5'-GCTAGTTATTGCTCAGCGG-3' and 5'-TAATACGACTCACTATAGGG-3' (SEQ ID NO:3 and SEQ ID NO:4, respectively). Thrombomodulin coding sequences are available on GenBank; see, e.g., Accession No. J02973.

Figure 2:
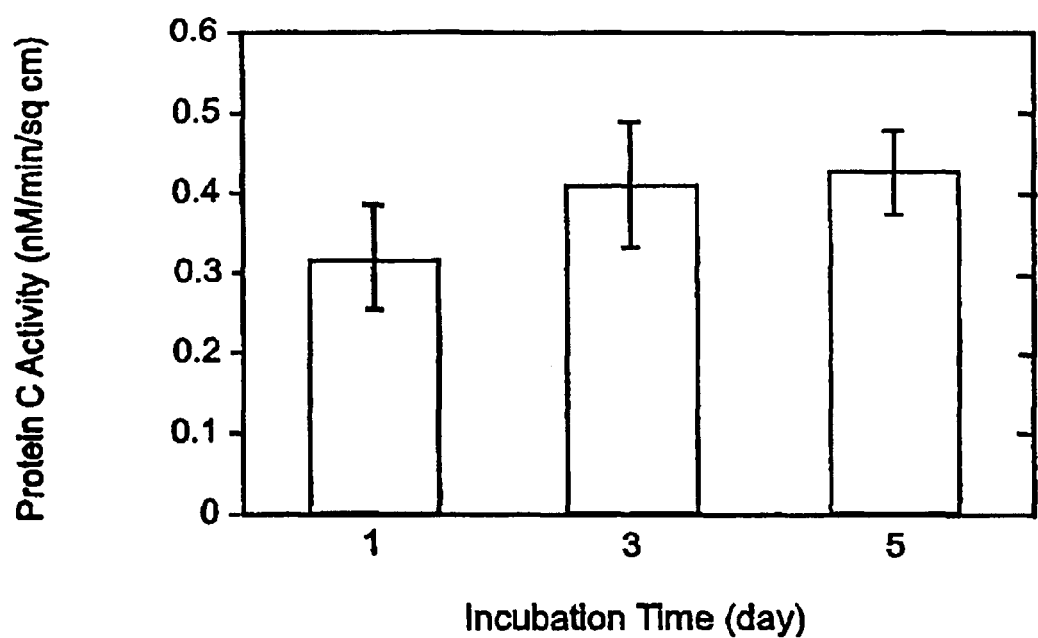
FIG. 2 shows that the surface-associated TM in the planar photopolymerized membrane-mimetic surface assembly is stable over at least 5 days of storage in PBS at 4 C. Stability is measured as the ability to activate protein C.
Figure 3:
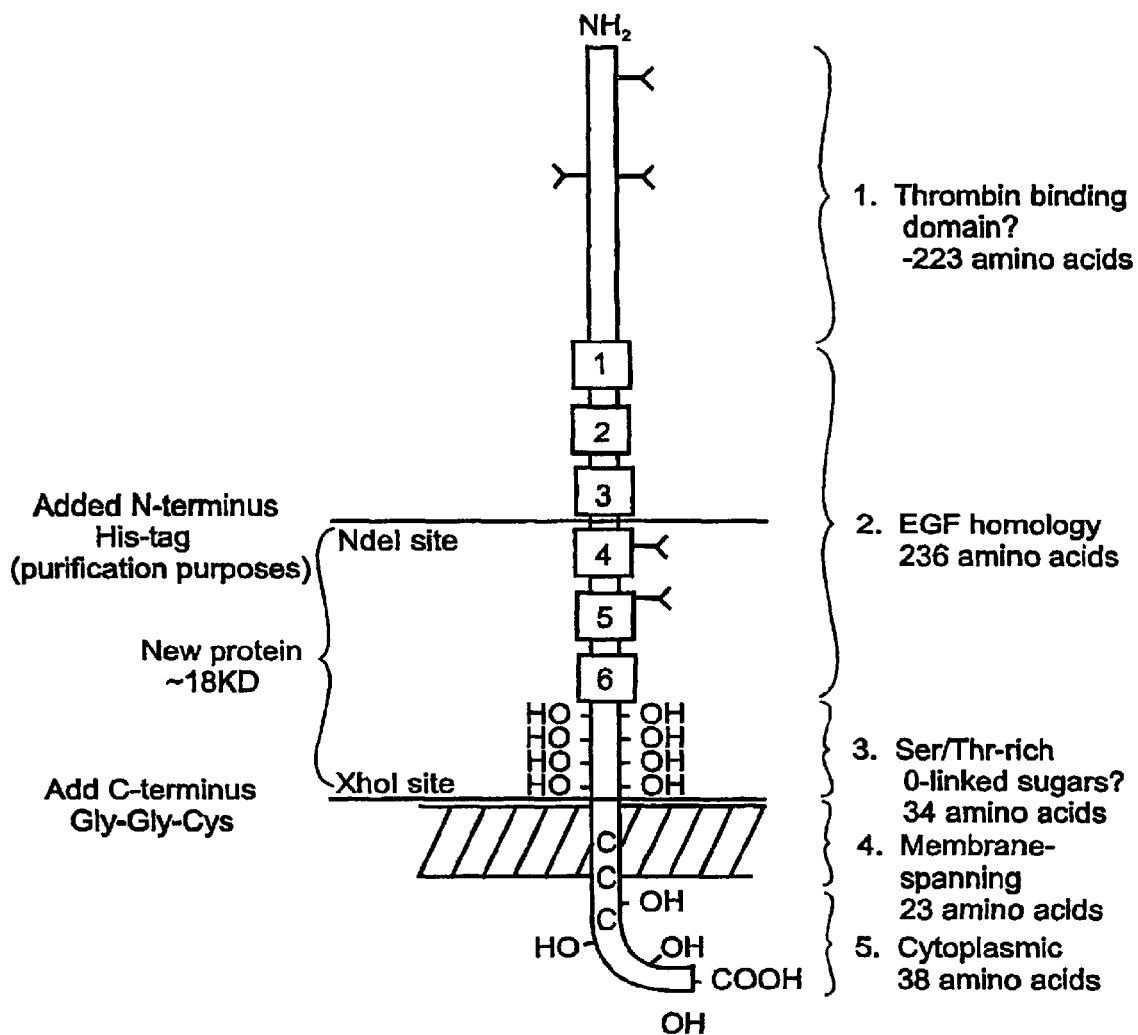
FIG. 3 is a schematic of the thrombomodulin protein, with the modifications made for expression of the truncated TM molecule used in the present work. An N-terminus of polyhistidine was incorporated by genetic engineering techniques at a NdeI site and eliminating 223 amino acids of the natural TM protein, and a C-terminus (Gly-Gly-Cys) was created, again through genetic engineering, at a XhoI site, eliminating the membrane spanning domain of 23 amino acids and the 38 amino acid cytoplasmic tail.
Figure 4:
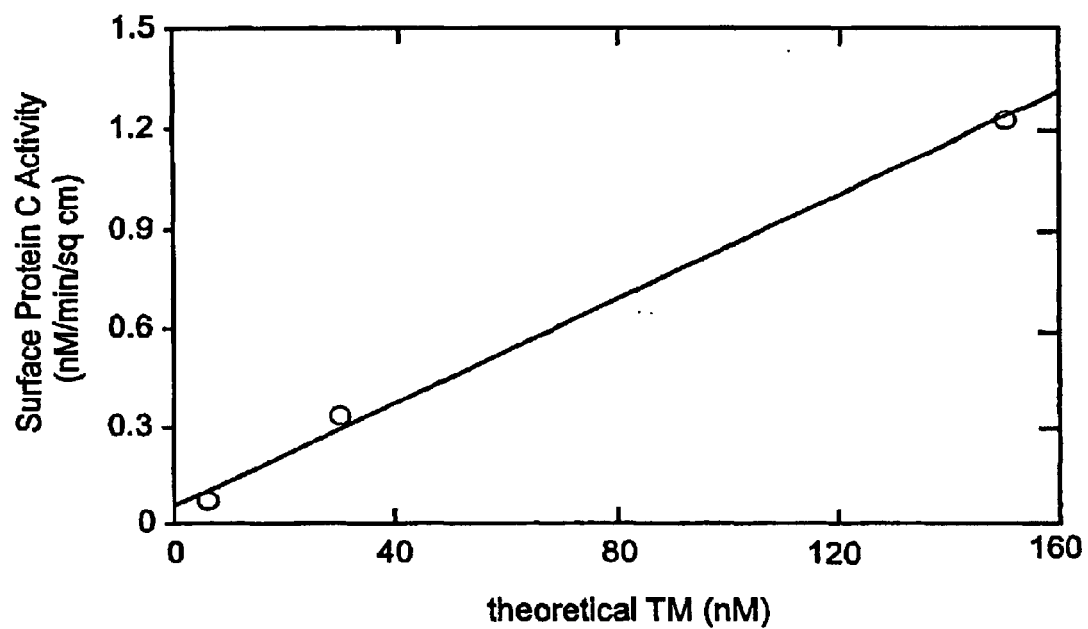
FIG. 4 illustrates that surface dependent APC activity increases with increasing TM surface concentration, where the TM is associated with a membrane-mimetic surface assembly.

The PET28aTMS plasmid was transformed into BL21 (DE3) cells (Novagen, Madison, Wis.) and grown in 2 ml Luria Broth containing 30 μg/ml kanamycin at 37 C until the $OD_{600}$ reached 0.6. The culture was stored at 40 C overnight. The following morning, the cells were collected by centrifugation and resuspended in 2 ml fresh LB/kan. This 2 ml culture was used to inoculate a 50 ml culture that was again grown to $OD_{600}$ Of 0.6. The culture was induced by the addition of IPTG to a final concentration of 1 mM and incubated for a total of 5 hours, taking 1 ml aliquots each hour for analysis. Induced TM protein expression was confirmed by SDS-PAGE (12% acrylamide) and western blot using a His-Tag monoclonal antibody (Novagen, 70796-4) (FIG. 2). Preliminary purification studies were done on the 5 hour induction aliquots using a Ni-NTA (Qiagen) protein miniprep procedure under native conditions. Briefly, cells were resuspended in lysis buffer (50 mM $NaH_2PO_4$, 300 mM NaCl, 10 mM imidazole, pH 8.0) and lysozyme to 1 mg/ml. Cells were vortexed, and cell debris was pelleted. The supernatant was added to Ni-NTA resin for 30 min at 40 C, then washed with wash buffer (50 mM $NaH_2PO_4$, 300 mM NaCl, 20 mM imidazole, pH 8.0). The protein was eluted with elution buffer (50 mM $NaH_2PO_4$, 300 mM NaCl, 250 mM imidazole, pH 8.0). The eluted TM was used in a thrombomodulin activity assay where thrombomodulin activity was confirmed (Table 1).

Example 3

Liposomes Containing Thrombomodulin

Rabbit thrombomodulin in 0.1% Lubrol PX was obatined from Haematological Technologies, Inc. Nucleopore polycarbonate filters are obtained from Fisher. Acrylic-PC (1-palmitoyl-2-[12-(acryloyloxy)dodeca-noyl]-sn-glycero3-phosphocholine was synthesized as described in Marra et al. (1997) supra.

TM was reconstituted into lipid vesicles as follows: 10 mM lipid solution containing no TM was freeze-thaw-vortexed 3 times before TM was added to make a final TM concentration of 10 nM. The solution was gently mixed and vortexed for 30 minutes before it was extruded through 2000 and 600 nm polycarbonate filters successively. Photopolymerization of AcPC was carried out as follows (Orban et al. (2000) supra). A 10:1 ratio of [AcPC]:[Eosin Y] was added to the AcPC containing TM, and the solution was irradiated for 30 minutes under ambient conditions (lamp power of approximately 30 mW/cm$^2$) from above at a distance of approximately 3 cm.

Sucrose density centrifugation was carried out in an SW 40Ti rotor (Beckman). Reconstituted TM was layered on top of a 6-mL 5–30% discontinuous sucrose gradient prepared in TBS and centrifuged for 16 h at 130,000×g. Aliquot of 0.6 mL was transferred into microcentrifuge tube and TM activity in each fraction was determined.

In an alternative procedure, large unilamellar vesicles (LUV) of 12 mM lipid solution in 20 mM sodium phosphate buffer, pH 7.4, were prepared by four successive freeze-thaw-vortex cycles using liquid nitrogen and a 45 C water bath. TM was them added to make the desired molar TM:lipid ratio, which ranges from 1:8000 (60 nM TM) to 1;2000,000 (60 nM TM). The lipid/TM solution was gently vortexed for at least 1 hr at room temperature before it was extruded 21 times, each through two back-to-back 2000 nm and then 600 nm polycarbonate filters.

Example 4

TM Vesicle Fusion and Photopolymerization

The extruded lipid/TM solution from above was diluted to 1.2 mM with 20 mM sodium phosphate buffer, pH 7.4, and a final salt concentration was achieved using 750 mM NaCl in water. This solution was then purged with argon for 15 min. To a scintillation vial that was purged with argon 1.2 ml of the vesicle solution was added with a terpolymer-coated round glass cover slip (20 mm diameter). The cover slip was immediately immersed in the vesicle solution, facing upwards. The vial was capped quickly and maintained at 40 C overnight.

Photopolymerization of the acrylic-PC in the terpolymer complex coating was carried out as follows: A stock solution of co-initiators as 10 mM EY, 225 mM triethanolamine and 37 mM VP in water, and stored in an amber bottle. In a glove bag purged with argon, the disred amount of initiator stock solution was added to the vial containing the cover slip substrate fused with the vesicles so that a 12:1 ration of monomer:EY was achieved. The mixture was then irradiated for 30 min. under ambient conditions (light intensity of about 40 mW per square cm) from above at a distance of about 6 cm. Following the photopolymerization period, the sample was removed from the polymerization media and washed extensively with water. This protocol is modified for using with tubing, where the lumen is perfused with the relevant solutions in an inert atmosphere.

Activity of rabbit TM was accessed via the activation of human protein C by human thrombin-rabbit TM complex (Galvin et al. (1987) vide infra). All activations were performed in TBS containing 0.1% BSA and 5 mM Ca$^{2+}$ at 37° C. A typical assay contains 1 nM TM, 5 nM Thrombin, and 100 nM protein C. Activated protein C concentration was determined based on their amidolytic activities toward 0.2 mM Spectrozyme PCa substrate (American Diagnostica, Inc.).

Rabbit TM was reconstituted into unilamellar phospholipid vesicles using an extrusion method. TM was added to the phospholipid solution after the freeze-thaw-vortex cycles and before extrusion, to prevent from activity loss. Over 95% of the TM activity was found to be associated with POPC lipid vesicles which stayed at the top of the sucrose gradient; on the other hand, free TM (as purchased) stayed at the bottom of the sucrose gradient. This high level of reconstitution made the separation of reconstituted TM from free TM unnecessary, which is one of the advantages of the extrusion method. The other advantage of this method is that TM activity loss during extrusion period (less than 2 h) is significantly less than that during the dialysis period (approximately 36 h), as reported previously in the literature (Galvin et al. (1987) *J. Biol. Chem.* 262, 2199).

Figure 5:
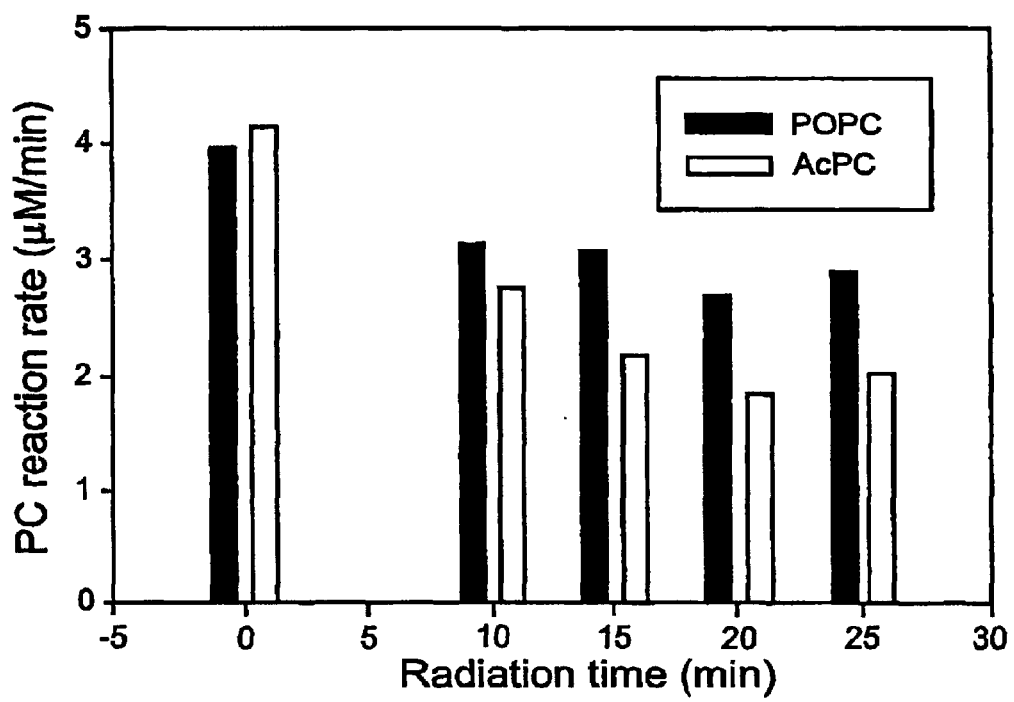
FIG. 5 shows the effects of photopolymerization time on the protein C activation rate. TM was incorporated at a surface concentration of 10 nM into either POPC or acrylic-PC vesicles.
Figure 6:
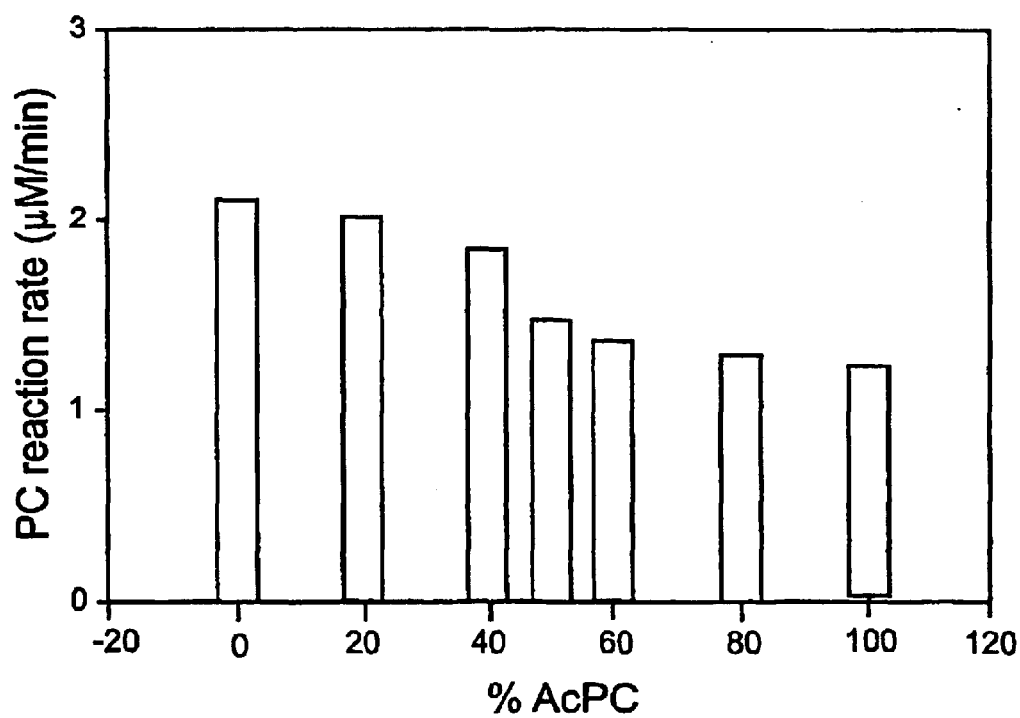
FIG. 6 illustrates the effect of lipid composition on the AcPC rate. TM ws incorporated at a surface concentration of 10 nM into mixed POPC/AcPC vesicles. The photopolymerization period was 30 min.

Photopolymerization of TM containing lipid assemblies. After TM was reconstituted into phospholipid vesicles varying in mole ratio of POPC to AcPC, vesicles were exposed to visible light for 30 minutes in the presence of eosin Y/triethanolamine. All vesicle systems, irrespective of lipid composition (POPC vs AcPC), exhibited similar rates of protein C activation prior to polymerization. However, following photopolymerization a modest reduction in the protein C activation rate was noted (FIG. 5). We believe that this effect may be attributed to inactivation of a portion of TM molecules by free radicals generated during the polymerization process and catalytic efficiency may be somewhat diminished due to reduced TM mobility within the membrane mimetic complex. We note that the reduction of catalytic activity is greater when TM is incorporated into vesicles composed of increasing concentrations of polymerizable lipids (FIG. 6).

TABLE 1

| Activated Protein C Assay (Simple Reads Report) | |
|---|---|
| Software Version: | 02.00 (25) |
| Instrument: | Cary 50 |
| Read | Abs (405 nm) |
| 1 | 1.6539 |
| Zero | (1.6464) |
| 2 | −0.0007 |
| 3 | −0.0570 |
| 4 | 0.0149 |
| 5 | −1.2100 |
| Zero | (0.4365) |
| 6 | −0.0013 |
| 7 | 0.0322 |
| 8 | 0.1312 |
| 9 | 0.3560 |
| Zero | (0.7941) |
| 10 | −0.0003 |
| | blank |
| 11 | 0.5834 |
| | denatured purification |
| 12 | 1.4431 |
| | native purification |

TABLE 2

Kinetic Parameters of Protein C Activation by Thrombin-TM Complex in Lipid Vesicles

| AcPC % | POPC % | Monomer (M) or Polymer (P) | $K_m$ ($\mu$M) | $K_{cat}$ (min$^{-1}$) |
|---|---|---|---|---|
| — | — | — | 4.2 ± 0.3 | 39 ± 1 |
| 0 | 100 | — | 1.3 ± 0.1 | 29 ± 1 |
| 100 | 0 | M | 1.1 ± 0.1 | 30 ± 1 |
| 100 | 0 | P | 3.0 ± 0.2 | 24 ± 1 |
| 50 | 50 | M | 1.0 ± 0.1 | 28 ± 1 |
| 50 | 50 | P | 2.1 ± 0.4 | 18 ± 1 |
| 80 | 20 | M | 1.4 ± 0.1 | 27 ± 1 |
| 80 | 20 | P | 3.0 ± 0.6 | 18 ± 2 |

Vesicles are composed of AcPC, POPC or mixtures thereof.
AcPC = acrylate derivatized-lipid.

TABLE 3

Determination of Km and kcat for TM as a function of local lipid microenvironment*

| | Free TM | TM in POPC vesicles | TM in AcPC vesicles | TM in polymerized AcPC vesicles |
|---|---|---|---|---|
| Km ($\mu$M) | 3.6 ± 1.1 | 0.66 ± 0.14 | 0.86 ± 0.10 | 4.5 ± 0.9 |
| kcat (min$^{-1}$) | 7.0 ± 1.0 | 4.6 ± 0.2 | 2.6 ± 0.1 | 5.7 ± 0.6 |
| kcat/Km (min$^{-1}$· $\mu$M$^{-1}$) | 1.94 | 6.97 | 3.02 | 1.27 |
| Km ($\mu$M) Ref.60) | 7.5 | 0.7 | NA | NA |

*Rabbit TM, human protein C, and human thrombin were sterilized in all experiments.

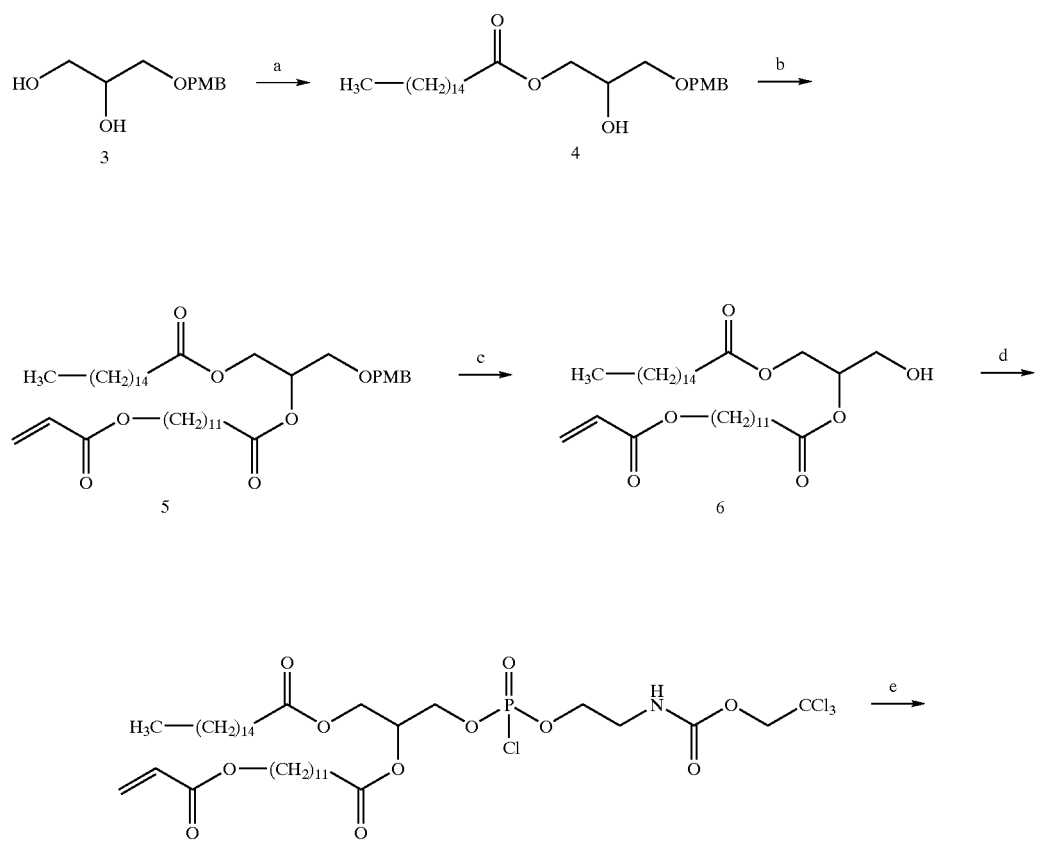

Scheme 1.
Synthesis of acrylate functionalized phosphatidylethanolamine.

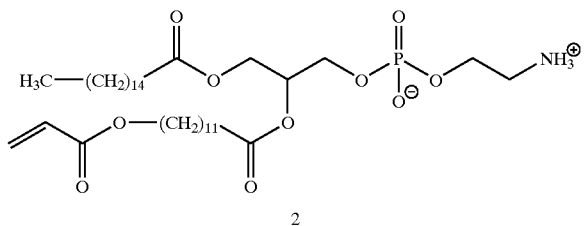
Reagent:
a) Palmitic acid, DCC, DAMP, CH$_2$Cl$_2$, 71%;
b) 12-acryloyloxydodecanoic acid, DCC, DAMP, CH$_2$Cl$_2$, 79%;
c) DDQ, CH$_2$Cl$_2$/H$_2$O, 55%;
d) 2,2,2-trichloroethoxyamide, NEt$_3$, CH$_2$Cl$_2$, 71%;
e) Zn/HOAc, 62%
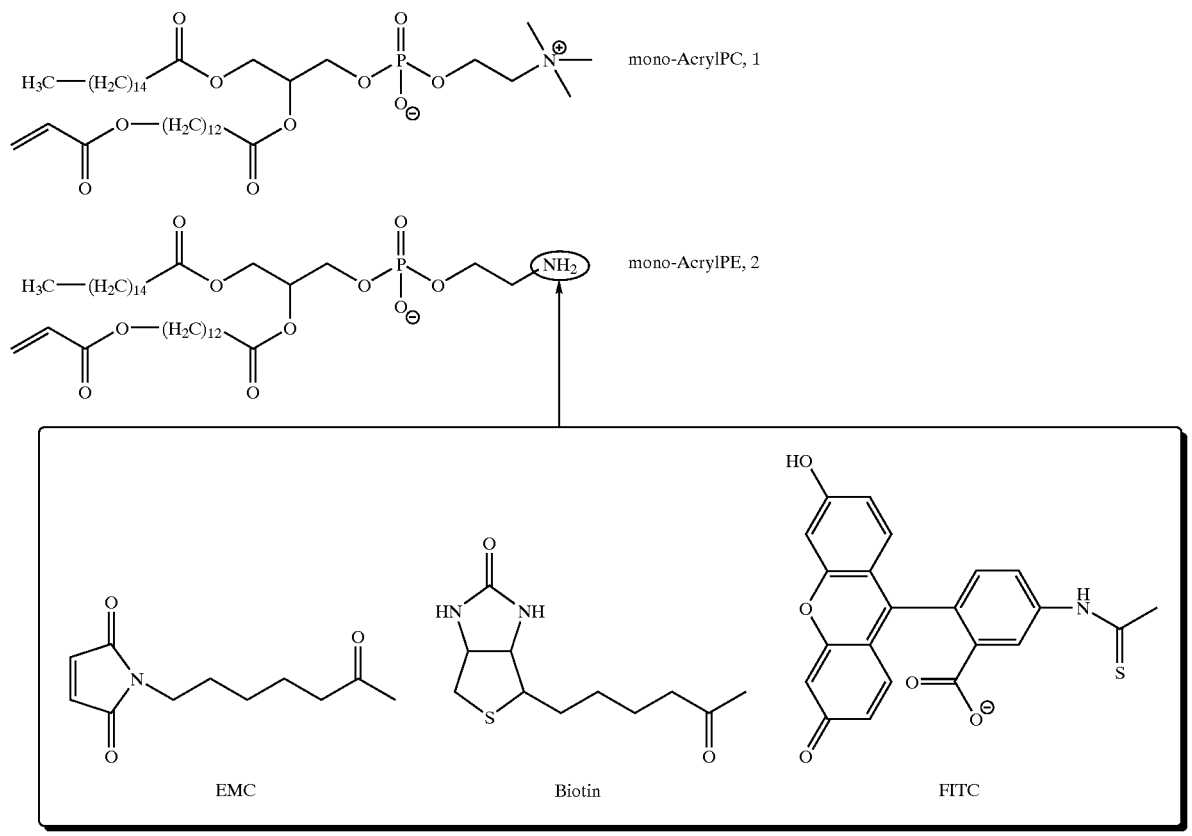
Scheme 2.
Structure and synthesis of bifunctional phospholipid conjugates.
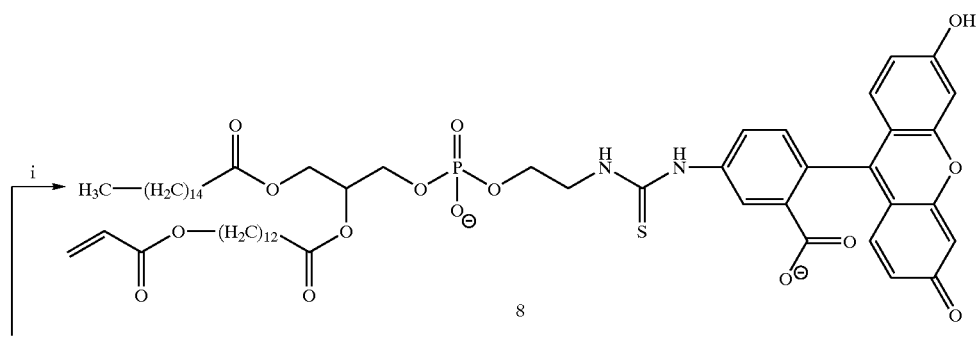

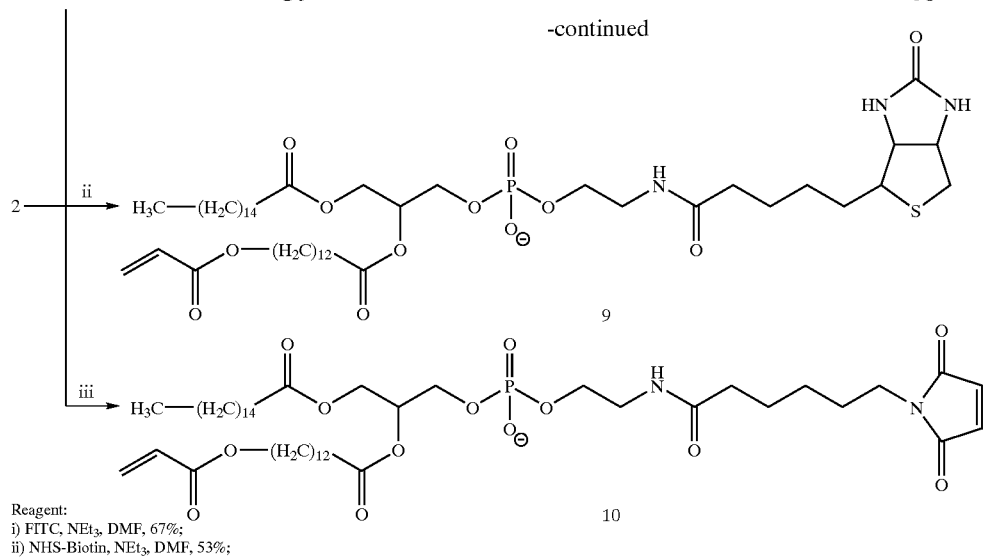
Reagent:
i) FITC, NEt₃, DMF, 67%;
ii) NHS-Biotin, NEt₃, DMF, 53%;
iii) EMCS, NEt₃, DMF, 71%
Scheme 3.
Photopolymerization of mono-AcrylPE-FITC with mono-AcrylPC on the bead surface.
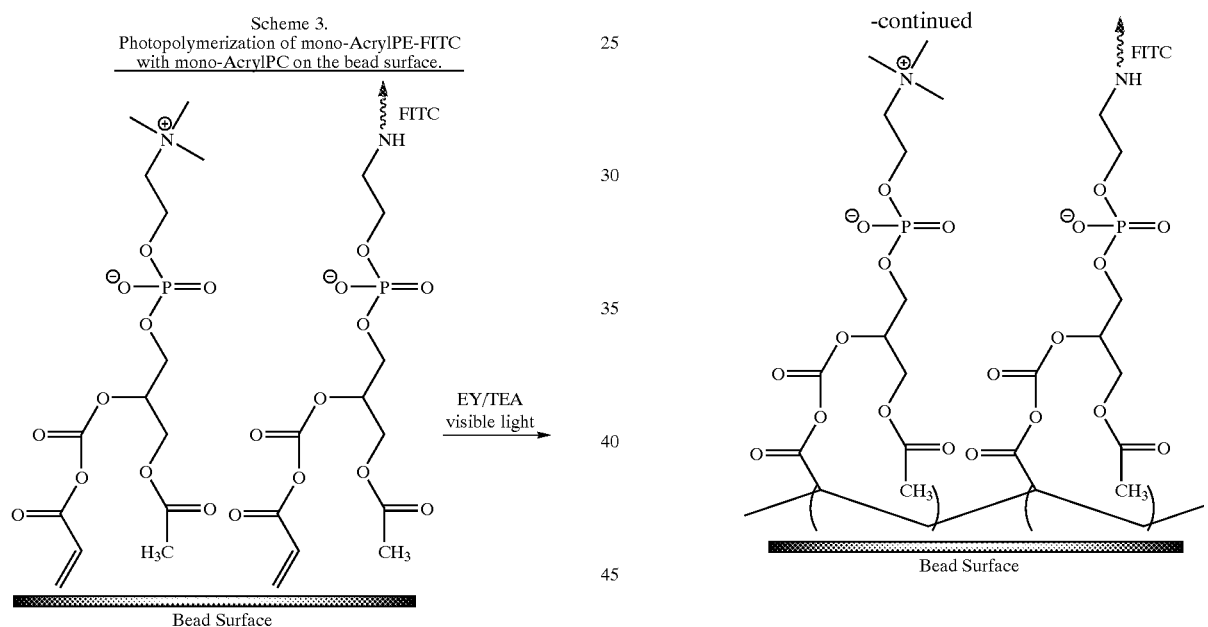
Scheme 4.
Synthesis and terminal functionalization of polymerizable phosphatidylethanolamine.
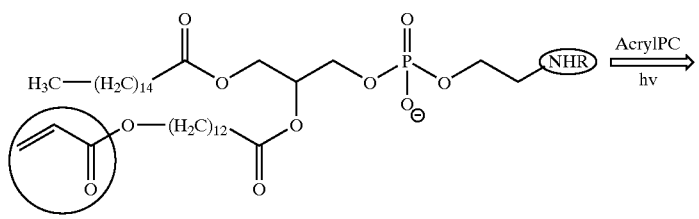
R = FITC, Biotin, EMC

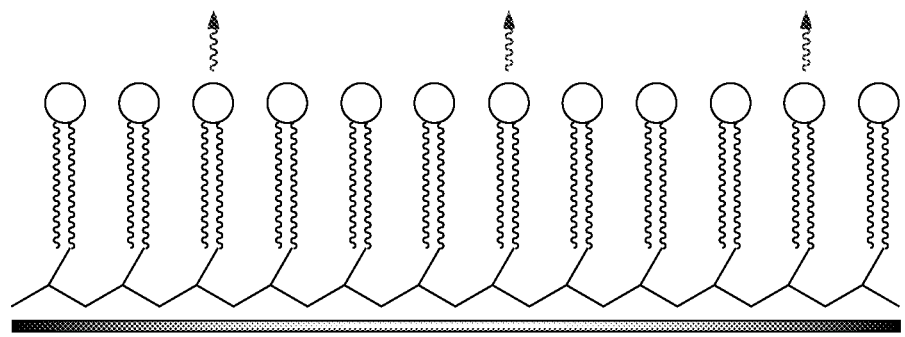
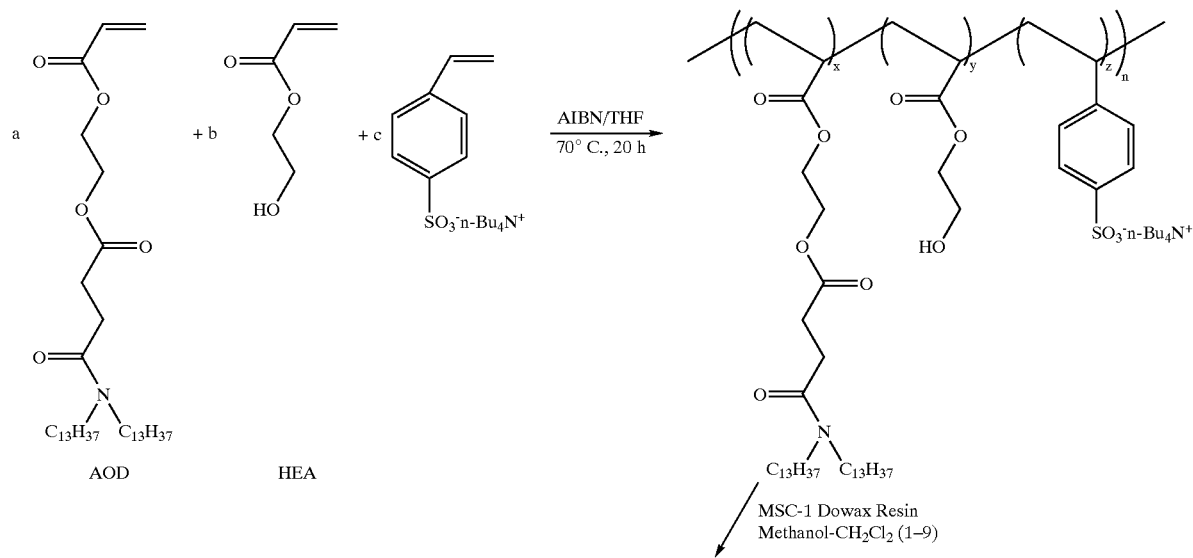
Scheme 5.
Synthesis of HEA:AOD (2.1) and HEA:AOD styrene sulfonate (6:3:1).
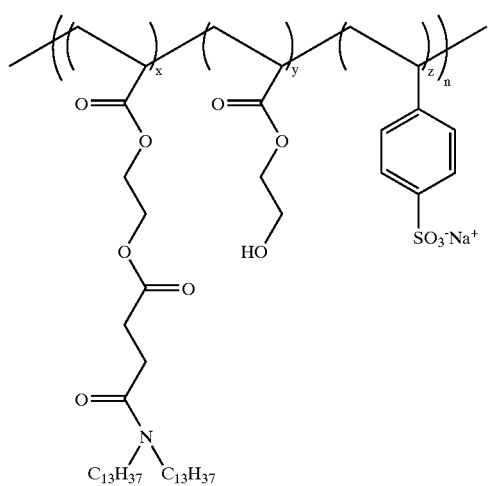
Terpolymer: a = x = 3
b = y = 6
c = z = 1
HEA-AOD copolymer:
a = x = 1
b = y = 2
c = z = 0

Scheme 6A.
Stabilizing a membrane-mimetic monolayer by photocrosslinking across the lipid layer.

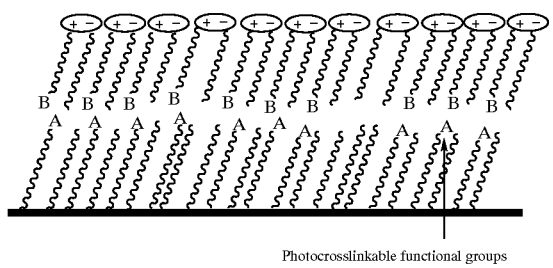

Photocrosslinkable functional groups

Scheme 6B.
Generation of membrane-mimetic monolayer utilizing a phosphatidylcholine containing boloamphiphile.

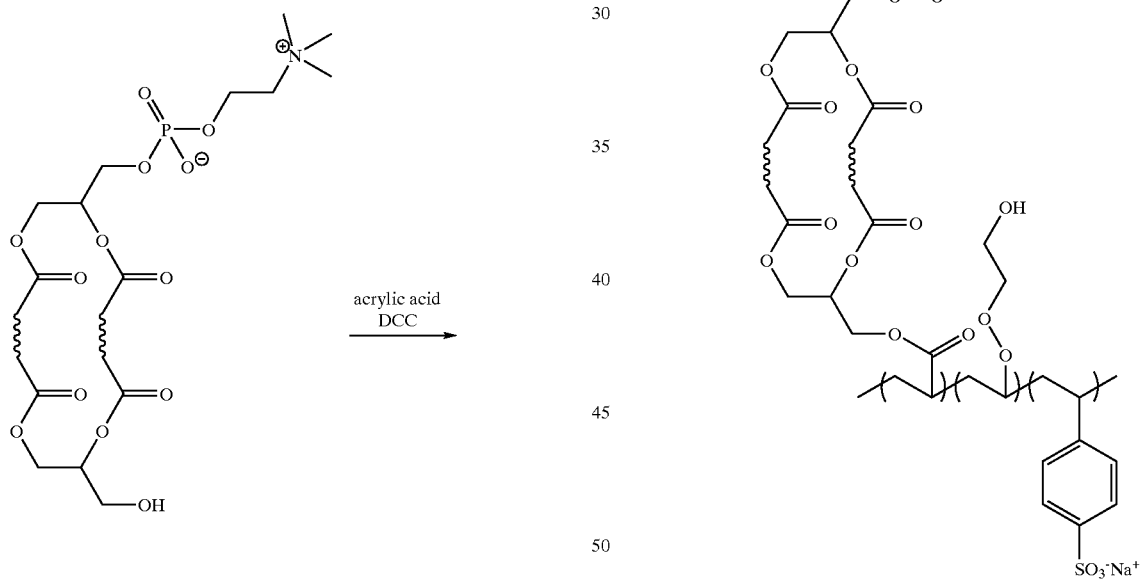

What is claimed is:

1. A method for producing an antithrombotic membrane mimetic surface on a synthetic prosthesis, synthetic vascular graft, medical implant, medical device orheterograft tissue, said method comprising the steps of
   (a) providing a hydrated surface on at least one surface of a synthetic prosthesis, synthetic vascular graft, medical implant, heterograft tissue or medical device;
   (b) complexing at least one polyelectrolyte to the hydrated surface of step (a) to produce a polyelectrolyte-complexed surface;
   (c) coating the polyelectrolyte-complexed surface of step (b) with an amphiphilic polymer, wherein said amphiphilic polymer comprises alkyl groups of from about 8 to about 20 carbon atoms, to produce an alkylated hydrated surface;
   (d) providing at least one polymerizable functionalized phospholipid to the alkylated surface of step (c) and further fusing antithrombotic liposomes to the alkylated hydrated surface of step (c) to produce a stabilization surface;
   (e) photopolymerizing the at least one polymerizable functionalized phospholipid in the stabilization surface of step (d) to produce an antithrombotic membrane mimetic surface on the synthetic prosthesis, synthetic vascular graft, medical implant, medical device or heterograft tissue,
   whereby the synthetic prosthesis, synthetic vascular graft, medical implant or medical device is improved in biocompatibility over a synthetic prosthesis, synthetic vascular graft, medical implant or medical device lacking said antithrombotic membrane mimetic surface.

2. The method of claim 1 wherein the hydrated surface comprises at least one of collagen, gelatin and/or alginate.

3. The method of claim 1 wherein the polyelectrolyte is at least one polyelectrolyte selected from the group consisting of alginate and poly-L-lysine.

4. The method of claim 1 wherein the antithrombotic liposomes of step (d) comprise an antithrombotic protein selected from the group consisting of thrombomodulin, a truncated thrombomodulin, endogenous protein C, an endothelial protein C receptor, and an endogenous protein C activator protein.

5. The method of claim 1 wherein the polymerizable functionalized phospholipid of step (d) comprises a phosphatidylcholine moiety and/or a phosphatidylethanolamine moiety.

6. The method of claim 1 wherein the polymerizable functionalized phospholipid is a mono-acrylate, a bis-acrylate, a mono-diene or a bis-diene derivative of a phospholipid.

7. The method of claim 6 wherein the wherein the polymerizable functionalized phospholipid is selected from the group consisting of mono-acrylate functionalized phosphatidylcholine, acrylate functionalized phosphatidylethanolamine, and combinations thereof.

8. The method of claim 1 wherein the amphiphilic polymer is a 2-hydroxyethyl acrylate (HEA): 3-acryloyl-e-3-(N,N-dioctadecylcarbamoyl propionate) (AOD): styrene sulfonate (SS) terpolymer.

9. The method of claim 8 wherein the ratio of HEA to AOD to SS is about 6 to about 3 to about 1.

10. The method of claim 1 wherein the vascular graft, synthetic prosthesis, heterograft tissue or medical device comprises a porous conduit having an exterior surface and a lumenal surface and wherein the antithrombotic membrane mimetic surface is produced on a lumenal surface of the conduit.

11. The method of claim 10 wherein the conduit has an inner diameter of less than or equal to about 6 mm.

12. The method of claim 11 wherein the conduit has an inner diameter of about 4 to about 6 mm.

13. The method of claim 10 wherein the porous conduit is a vascular graft, stent or shunt.

14. The method of claim 10 wherein the synthetic prosthesis is an artificial heart valve or an artificial organ.

15. The method of claim 1 wherein the medical device is dialysis tubing, a dialysis membrane, a hollow-fiber dialysis system, a left ventricular assist device or a diagnostic device with a blood-contacting surface.

16. The method of claim 1 wherein the heterograft tissue is a porcine heart valve or a bovine carotid vascular heterograft.

17. The method of claim 1 wherein the antithrombotic membrane mimetic surface is produced on expanded polytetrafluoroethylene (ePTFE), polytetrafluoroethylene (PTFE), polyethylene terephthalate (PET), poly (ether urethaneurea) (PEU) or Dacron.

18. The method of claim 1 wherein the antithrombotic membrane mimetic surface is produced on silicon, glass or metal.

19. A synthetic prosthesis, synthetic vascular graft, medical implant, heterograft tissue or medical device comprising at least one antithrombotic membrane mimetic surface produced by the method of claim 1.

20. The synthetic prosthesis, synthetic vascular graft, medical implant, heterograft tissue, or medical device of claim 19, wherein the antithrombotic liposomes comprise an antithrombotic protein selected from the group consisting of thrombomodulin, a truncated thrombomodulin, endogenous protein C, an endothelial protein C receptor, and an endogenous protein C activator protein.

21. The medical device of claim 19 which is a diagnostic medical device comprising a substrate of silicon or a substrate of silicon coated with metal.

* * * * *

UNITED STATES PATENT AND TRADEMARK OFFICE
CERTIFICATE OF CORRECTION

PATENT NO. : 6,936,298 B2
APPLICATION NO. : 10/257805
DATED : August 30, 2005
INVENTOR(S) : Chaikof et al.

It is certified that error appears in the above-identified patent and that said Letters Patent is hereby corrected as shown below:

Column 1,
Lines 15-18, under "Acknowledgment of Federal Research Support," replace the entire first paragraph with -- This invention was made with government support under NIH Contract No. HL56819 awarded by the National Institutes of Health. The government has certain rights in the invention. --.

Column 45,
Line 44, replace "orheterograft" with -- or heterograft --.

Column 46,
Line 63, replace "wherein the wherein the" with -- wherein the --.

Column 48,
Line 5, replace "urethaneurca" with -- urethaneurea --.

Signed and Sealed this

Twentieth Day of June, 2006

JON W. DUDAS
*Director of the United States Patent and Trademark Office*

SEQUENCE LISTING

<160> NUMBER OF SEQ ID NOS: 4

<210> SEQ ID NO 1
<211> LENGTH: 38
<212> TYPE: DNA
<213> ORGANISM: Artificial Sequence
<220> FEATURE:
<223> OTHER INFORMATION: oligonucleotide useful for cloning human
      thrombomodulin sequences

```
<400> SEQUENCE: 1
gagatatacc atatgtaccc taactacgac ctggtgga                    38

<210> SEQ ID NO 2
<211> LENGTH: 50
<212> TYPE: DNA
<213> ORGANISM: Artificial Sequence
<220> FEATURE:
<223> OTHER INFORMATION: oligonucleotide useful for cloning human
      thrombomodulin sequences

<400> SEQUENCE: 2
cgcgcctcga gttaattaat tagcaaccac ctatgagcaa gcccgaatgc        50

<210> SEQ ID NO 3
<211> LENGTH: 19
<212> TYPE: DNA
<213> ORGANISM: Artificial Sequence
<220> FEATURE:
<223> OTHER INFORMATION: oligonucleotide useful for cloning human
      thrombomodulin sequences

<400> SEQUENCE: 3
gctagttatt gctcagcgg                                         19

<210> SEQ ID NO 4
<211> LENGTH: 20
<212> TYPE: DNA
<213> ORGANISM: Artificial Sequence
<220> FEATURE:
<223> OTHER INFORMATION: oligonucleotide useful for cloning human
      thrombomodulin sequences

<400> SEQUENCE: 4
taatacgact cactataggg                                        20
```